(12) United States Patent
Hanson et al.

(10) Patent No.: US 8,173,628 B2
(45) Date of Patent: May 8, 2012

(54) STEROIDAL ANTIESTROGENS AND ANTIANDROGENS AND USES THEREOF

(75) Inventors: Robert N. Hanson, Newton, MA (US);
Carolyn Friel, Holden, MA (US);
Choon Young Lee, Mount Pleasant, MI (US)

(73) Assignee: Northeastern University, Boston, MA (US)

( * ) Notice: Subject to any disclaimer, the term of this patent is extended or adjusted under 35 U.S.C. 154(b) by 374 days.

(21) Appl. No.: 11/975,727

(22) Filed: Oct. 19, 2007

(65) Prior Publication Data

US 2008/0166301 A1    Jul. 10, 2008

Related U.S. Application Data

(63) Continuation-in-part of application No. 11/369,582, filed on Mar. 7, 2006, now abandoned, which is a continuation of application No. 10/297,310, filed as application No. PCT/US01/20142 on Jun. 22, 2001, now Pat. No. 7,041,839.

(60) Provisional application No. 60/213,282, filed on Jun. 22, 2000.

(51) Int. Cl.
*A61K 31/56* (2006.01)

(52) U.S. Cl. ...................................................... 514/182
(58) Field of Classification Search ................... 552/182; 514/182
See application file for complete search history.

(56) References Cited

U.S. PATENT DOCUMENTS

| 3,193,564 A | 7/1965 | Kilmstra et al. ............ 260/397.5 |
| 3,401,181 A | 9/1968 | Klimstra ..................... 260/397.5 |
| 4,705,783 A | 11/1987 | Crowe et al. .................... 514/180 |
| 4,725,426 A | 2/1988 | Hofmeister et al. ............ 424/1.1 |
| 6,677,329 B1 | 1/2004 | Loozen et al. ................. 514/182 |

*Primary Examiner* — Barbara P Badio
(74) *Attorney, Agent, or Firm* — Weingarten, Schurgin, Gagnebin & Lebovici LLP

(57) ABSTRACT

The present invention comprises the design, synthesis and development of a new class of chemotherapeutic agents for prophylactic and therapeutic treatments in a mammal, particularly a human, believed to be at risk of suffering from a hormone-responsive disorder. In an aspect of the invention, such treatments include therapeutic compositions comprising novel steroidal antiestrogen and antiandrogen compounds. In a preferred aspect, such a novel compound of the present invention has an address and a message component, which are made into a single composite entity for more aggressive intervention and effective treatment of hormone-responsive disorders, thereby prolonging the disease-free interval for the patient and reducing a number of side effects.

1 Claim, 12 Drawing Sheets

Examples of Address Units

Examples of Composite Address - Message Unit

Examples of Message Units

X = -OH, -NH$_2$

Antiestrogens
R = CH$_2$CH$_2$NR$_2$    RU 39411
R = (CH$_2$)$_3$SO$_2$(CH$_2$)$_3$CF$_2$CF$_3$   RU58568

Antiestrogens
R = N(CH$_3$)$_2$    RU34486
R = COCH$_3$    Onapristone

Antiestrogens

Our current work (unpublished)

Antiestrogens
R = (CH$_2$)$_{10}$CON(CH$_3$) C$_4$H$_9$   ICI 164384
R = (CH$_2$)$_9$SO(CH$_2$)$_3$ CF$_2$CF$_3$   ICI 182780

Hydroxy Flutamide

Casodex (Bicalutamide)

Nilutamide

LG 120907

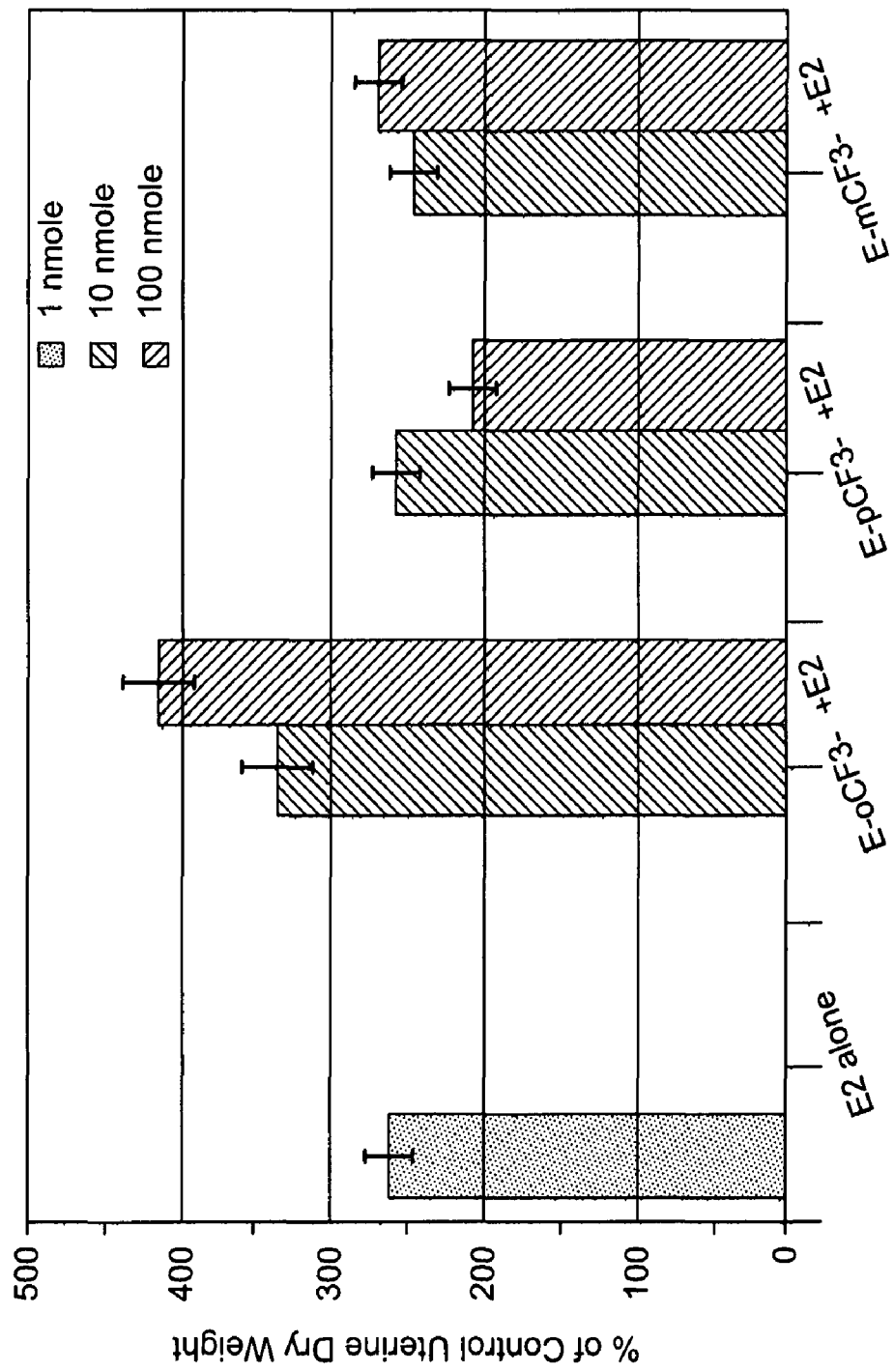

STEROIDAL ANTIESTROGENS AND ANTIANDROGENS AND USES THEREOF

CROSS REFERENCE TO RELATED APPLICATIONS

The present application is a continuation-in-part application of U.S. application Ser. No. 11/369,582, entitled NOVEL STEROIDAL ANTIESTROGENS AND ANTIANDROGENS AND USES THEREOF and filed Mar. 7, 2006, now abandoned, which is a continuation application of U.S. application Ser. No. 10/297,310, entitled STEROIDAL ANTIESTROGENS AND ANTIANDROGENS AND USES THEREOF and filed Dec. 4, 2002, now U.S. Pat. No. 7,041,839, which was a 35 U.S.C. §371 filing of International Application No. PCT/US01/20142, entitled NOVEL STEROIDAL ANTIESTROGENS AND ANTIANDROGENS AND USES THEREOF and filed Jun. 22, 2001, and further claims the priority benefit of provisional U.S. Application No. 60/213,282, entitled NOVEL STEROIDAL ANTIANDROGENS AND USES THEREOF and filed Jun. 22, 2000, the whole of which are each hereby incorporated by reference herein.

STATEMENT REGARDING FEDERALLY SPONSORED RESEARCH OR DEVELOPMENT

Part of the work leading to this invention was carried out with United States Government support provided under a grant from the National Institutes of Health, Contract Number 1R01CA81409. Therefore, the United States Government has certain rights in this invention.

BACKGROUND OF THE INVENTION

Antagonists to both estrogen and androgen receptors have been developed for the treatment of hormone-related conditions. For example, antiestrogenic agents are useful for the treatment of breast cancer and antiandrogenic agents are useful for the treatment of prostate cancer.

Breast cancer, at 182,000 cases per year, is the most common cancer diagnosis among women in the United States, accounting for over 40,000 deaths annually (Greenlee, 2000). It is estimated that one in eight women will develop breast cancer during their lifetime and one in three of those will die from the disease. Of those women diagnosed with breast cancer, approximately 60% have tumors that are classified as hormone-responsive, meaning that the tissue contains elevated levels of the estrogen receptor and the tumor cell proliferation is stimulated by circulating estrogens (Scott, 1991). Various available treatments include surgery (e.g., lumpectomy, mastectomy or modified radical mastectomy, which removes the breast and underlying muscle along with adjacent lymph nodes), radiation, chemotherapy or biological treatments.

Hormonal therapy characterized as either removal of estrogen producing tissues, inhibition of estrogen biosynthesis or blockade of estrogen receptors by antagonists (e.g., tamoxifen (Nolvadex®) and Faslodex®, raloxifene, and idoxifene), has been shown to produce a positive objective response (Beatson, 1896; Boyd 1900; Bhatanagar, 1999; Cole, 1971; and Lancet 351, 1998). Such interventions, however, are often accompanied by major side effects that are tolerated because of the particular risks associated with the primary disease. Over the past 10 years, studies with antiestrogens structurally related to tamoxifen have demonstrated that some of the side effects can be ameliorated, depending upon the features incorporated within the structure of the drug. Agents that may block cancer cell proliferation (antagonism) without eliminating the beneficial effects on bone density and cardioprotection have been termed Selective Estrogen Receptor Modulators (SERMs) (Grese; Levenson, 1999). Known non-steroidal antagonists that are tamoxifen-like and raloxifene-like display antiestrogen effects in some tissues and estrogen-like effects in others. These SERMs may be beneficial for the treatment of hormone responsive cancers (or potentially as prophylactic agents) without causing osteoporosis or increasing the risk for cardiovascular disease. However, their receptor affinity is generally less than that of estradiol, and because they have a non-steroidal structure, they often exhibit additional, non-hormonal effects. Additionally, hormone responsive cancers progress to a stage where they become hormone-independent, requiring a subsequent, more aggressive approach.

Prostate cancer is the most common cancer diagnosis among American men (29%) and the second leading cause of death due to cancer (13%) (Landis, 1999; Haas, 1997; Mettlin, 1997). Like breast cancer in women, most of the newly diagnosed cases are hormone responsive and patients experience a reduction in tumor growth or regression with antihormone (antiandrogen) therapy (Roach, 1999).

Hormonal therapy is often used in all phases of prostate cancer treatment to help block production or action of the male hormones that have been shown to fuel prostate cancer. Antiandrogens are divided into two groups: steroidal and non-steroidal. Among widely used approved hormone blockers, often used in combination, are Casodex (bicalutamide), Eulexin (flutamide), Anandron (nilutamide), LG 120907, which are nonsteroidal (see FIG. 9), Lupron (leuprolide acetate), and Zoladex (goserelin acetate implant), which are peptides that block GnRH release. The nonsteroidal antiandrogens can be displaced by endogenous ligands, i.e., dihydrotestosterone. Therefore, these antiandrogens have not been as successful in the treatment of prostate cancer due to their reversibility in binding to the androgen receptor. Some studies have suggested that dihydrotestosterone bromoacetate (DHT-BA) binds irreversibly to the androgen receptor (AR). However, other studies show that DHT-BA apparently binds to aldehyde dehydrogenase and not to the AR (McCammon, 1993). Therefore, DHT-BA is not as optimal in the treatment of prostate cancer.

Because the testicles produce male hormones, some men also undergo testicle removal to cut off the hormone supply. Advanced prostate cancer patients are usually treated with any number of chemotherapeutic drugs such as Novantrone (mitoxantrone), which do not cure the disease but often do ease pain and other symptoms. However, within one to three years of such therapy, there is often recurrence of disease in which the tumor has acquired hormone independence (Galbraith, 1997). At this point, antiandrogen therapy becomes much less effective and a more aggressive intervention is required (Ornstein, 1999). A second issue is that current antiandrogen therapy, even when effective, elicits a number of side effects (e.g., impotence, incontinence, loss of libido, gynecomastia, heat intolerance, or hot flashes) that compromise the patient's quality of life.

Therefore, the development of more therapeutically effective antiestrogenic and antiandrogenic agents that target hormone-dependent tumors would: (1) provide a substantial benefit for the initial reduction of disease, (2) provide a prolonged disease-free interval, (3) improve the long term prognosis, (4) reduce the incidence and severity of the side effects, and (5) could potentially be used for detection and/or imaging type applications or uses.

BRIEF SUMMARY OF THE INVENTION

The present invention encompasses both prophylactic and therapeutic treatments for a mammal, preferably a human, at risk for a hormone-responsive disorder. Generally, prophylactic or prophylaxis relates to a reduction in the likelihood of the patient developing a disorder or proceeding to a diagnosis state for the disorder. For example, the compounds, probes, compositions, methods, kits, uses and so forth of the invention can be used prophylacticly as a measure(s) designed to preserve health and prevent the spread of disease. Furthermore, the invention also provides compounds and probes thereof that allow for safe and specific methods of in vivo diagnosis and/or quantitation of a disease state. The compounds, probes, compositions, methods, kits, uses and so forth of the invention are directed to treatments for both existing estrogen and androgen mediated disorders and prevention thereof. Such disorders or disease states include, but are not limited to, prevention or treatment of osteoporosis, endometriosis, breast cancer, benign breast cancer, uterine cancer, ovarian cancer, polycystic ovarian disease, prostate cancer, benign prostatic hyperplasia (BPH), cardiac diseases, coronary artery disease, acne, seborrhea, alopecia, hirsutism, male pattern baldness, and infertility.

It is also appreciated that the various modes of treatment or prevention of a disease or condition can mean "substantial" treatment or prevention, which includes total but also less than total treatment or prevention, and in which some biologically or medically relevant result is achieved. Furthermore, treatment or treating as well as alleviating can refer to therapeutic treatment and prophylactic or preventative measures in which the object is to prevent, slow down (lessen) a disease state, condition or malady. For example, a subject can be successfully treated for a hormone-responsive disorder if, after receiving through administration an effective or therapeutic amount of one or more compounds of the invention, the subject shows observable and/or measurable reduction in or absence of one or more signs and symptoms of the particular disorder such as, but not limited to, reduced morbidity and mortality, or improvement in quality of life issues.

In one aspect, a compound or probe thereof according to the invention is an anti-estrogen compound having the structural formula, in the address/message construct described below:

a) an address unit having the structure:

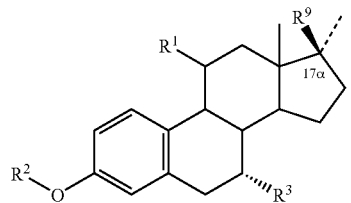

wherein:
$R^1$ is H, $CH_3$, $CH_2CH_3$, OH, $OCH_3$, $OCH_2CH_3$, $C_1$-$C_6$ alkyl, $CH=CH_2$, $CH=CHCH_3$, $CH_2$-aryl, detectable marker (exemplary detectable markers can comprise, but are not limited to, radionuclides, radioisotopes, Re, Tc, indium, La, terbium, yttrium, Cu or gallium) and $CH_3$, $CH_2CH_3$, OH, $OCH_3$, $OCH_2CH_3$, $C_1$-$C_6$ alkyl, $CH=CH_2$, $CH=CHCH_3$, $CH_2$-aryl can optionally and independently each comprise (e.g., as an alternative or additional substituent) at least one detectable marker;

$R^2$ is H, $CH_3$, $COCH_3$, $CO(CH_2)_nCH_3$, CO-aryl, alkyl, cycloalkyl (ether), ester, —$COCH_3$, detectable marker and $CH_3$, $COCH_3$, $CO(CH_2)_nCH_3$, CO-aryl, alkyl, cycloalkyl (ether), ester, —$COCH_3$ can optionally and independently each comprise (e.g., as an alternative or additional substituent) at least one detectable marker;

$R^3$ is H, $CH_3$, $CH_2CH_3$, aryl, heteroaryl, alkyl $C_1$-$C_6$, alkyl ($C_1$-$C_6$) amides, alkyl ($C_1$-$C_6$) sulfide, alkyl ($C_1$-$C_6$) sulfone, alkyl ($C_1$-$C_6$) sulfoxide, detectable marker and $CH_3$, $CH_2CH_3$, aryl, heteroaryl, alkyl $C_1$-$C_6$, alkyl ($C_1$-$C_6$) amides, alkyl ($C_1$-$C_6$) sulfide, alkyl ($C_1$-$C_6$) sulfone, alkyl ($C_1$-$C_6$) sulfoxide can optionally and independently each comprise (e.g., as an alternative or additional substituent) at least one detectable marker;

$R^9$ is H, OH, $NH_2$, wherein OH or $NH_2$ can optionally and independently comprise (e.g., as an alternative or additional substituent) at least one detectable marker; and, attached to the 17α-position of the address unit, b) a message unit having the structure:

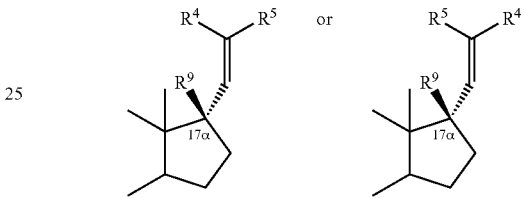

wherein:
$R^4$ is H, alkyl ($C_1$-$C_4$), detectable marker and alkyl ($C_1$-$C_4$) can optionally comprise (e.g., as an alternative or additional substituent) at least one detectable marker;

$R^5$ is aryl, heteroaryl, fused aryl, —CO-aryl, CO-fused aryl, —CO-heteroaryl, —CO-fused heteroaryl, biaryl, CO-biaryl, ether-linked aryls, ether-linked heteroaryls, amine-linked aryls, amine-linked heteroaryls, aminoalkoxy arene hybrid, detectable marker, peptidyl hybrid, wherein any aryl, heteroaryl, fused aryl, fused heteroaryl, —CO-aryl, CO-fused aryl, —CO-heteroaryl, —CO-fused heteroaryl, biaryl, CO-biaryl, ether-linked aryls, ether-linked heteroaryls, amine-linked aryls, amine-linked heteroaryls, aminoalkoxy arene hybrid, and peptidyl hybrid may optionally comprise (e.g., as an alternative or additional substituent), independently, at least one detectable marker, H, $CH_3$, OH, $OCH_3$, $OCF_3$, $N(CH_3)_2$, $NHCOCH_3$, aryl, $CO_2CH_3$, $CONH_2$, $C_1$-$C_4$ alkyl, $(CF_2)_nF$ wherein n=1-4, Cl, Br, I, F, $O(CH_2)_nH$ wherein n=1-4, $NO_2$, $NH_2$, $NHCOR^4$, $CO_2H$, $CO_2R^4$, $CONHR^4$, amyl, thioether, $SR^6$, $S(O)R^6$, $SO_2R^6$, $SO_2NR^6R^7$, and $CH_3$, OH, $OCH_3$, $OCF_3$, $N(CH_3)_2$, $NHCOCH_3$, aryl, $CO_2CH_3$, $CONH_2$, $C_1$-$C_4$ alkyl, $(CF_2)_nF$ wherein n=1-4, Cl, Br, I, F, $O(CH_2)_nH$ wherein n=1-4, $NO_2$, $NH_2$, $NHCOR^4$, $CO_2H$, $CO_2R^4$, $CONHR^4$, amyl, thioether, $SR^6$, $S(O)R^6$, $SO_2R^6$, $SO_2NR^6R^7$ can optionally and independently each comprise (e.g., as an alternative or additional substituent) at least one detectable marker; wherein $R^4$ has the definition given above; wherein $R^6$ is a detectable marker, H, $C_1$-$C_4$ alkyl or perfluoroalkyl, aryl, heteroaryl, or optionally substituted allyl, arylmethyl, alkynyl, alkenyl, wherein each of $C_1$-$C_4$ alkyl, perfluoroalkyl, aryl, heteroaryl, allyl, arylmethyl, alkynyl or alkenyl can optionally and independently comprise (e.g., as an alternative or additional substituent) at least one detectable marker; wherein $R^7$ is a detectable marker, H, $C_1$-$C_4$ alkyl, perfluoroalkyl, aryl, heteroaryl, optionally substituted allyl, arylmethyl, $OR^8$ or $NHR^8$, and wherein each of $C_1$-$C_4$ alkyl, perfluoroalkyl, aryl, heteroaryl, allyl, arylmethyl, $OR^8$ or $NHR^8$ can optionally and independently comprise (e.g., as an alternative or additional substituent) at least one detectable marker; and further wherein $R^8$ is a detectable marker, H, $C_1$-$C_6$ alkyl or perfluoroalkyl, aryl, heteroaryl, optionally substituted allyl or arylmethyl, $SO_2R^6$ or $S(O)R^6$, and $C_1$-$C_6$ alkyl, perfluoroalkyl, aryl, heteroaryl, allyl, arylmethyl, $SO_2R^6$ or $S(O)R^6$ can each optionally and independently comprise (e.g., as an alternative or additional substituent) at least one detectable marker, wherein $R^6$ has the definition given above; and wherein $R^5$ can be in either the E or Z configuration in relation to the 17α-position of the address unit.

In one aspect, a compound or probe thereof according to the invention is an antiestrogen compound having the structural formula, in the address/message construct described below:

a) an address unit having the structure:

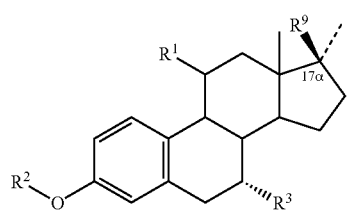

wherein:
$R^1$ is H, $CH_3$, $CH_2CH_3$, OH, $OCH_3$, $OCH_2CH_3$, $C_1$-$C_6$ alkyl, $CH=CH_2$, $CH=CHCH_3$, $CH_2$-aryl;
$R^2$ is H, $CH_3$, $COCH_3$, $CO(CH_2)_nCH_3$, CO-aryl, alkyl, cycloalkyl (ether), ester, —$COCH_3$;
$R^3$ is H, $CH_3$, $CH_2CH_3$, aryl, heteroaryl, alkyl $C_1$-$C_6$, alkyl ($C_1$-$C_6$) amides, alkyl ($C_1$-$C_6$) sulfide, alkyl ($C_1$-$C_6$) sulfone, alkyl ($C_1$-$C_6$) sulfoxide;
$R^9$ is H, OH, $NH_2$; and, attached to the 17α-position of the address unit, b) a message unit having the structure:

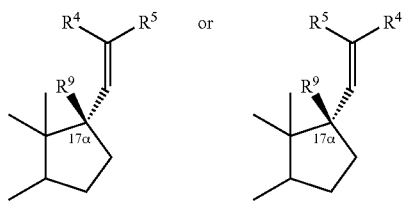

wherein:
$R^4$ is H, alkyl ($C_1$-$C_4$)
$R^5$ is aryl, heteroaryl, fused aryl, —CO-aryl, CO-fused aryl, —CO-heteroaryl, —CO-fused heteroaryl, biaryl, CO-biaryl, ether-linked aryls, ether-linked heteroaryls, amine-linked aryls, amine-linked heteroaryls, aminoalkoxy arene hybrid, peptidyl hybrid, wherein any aryl, heteroaryl, fused aryl, fused heteroaryl, —CO-aryl, CO-fused aryl, —CO-heteroaryl, —CO-fused heteroaryl, biaryl, CO-biaryl, ether-linked aryls, ether-linked heteroaryls, amine-linked aryls, amine-linked heteroaryls, aminoalkoxy arene hybrid, and peptidyl hybrid may optionally be substituted, independently, with H, $CH_3$, OH, $OCH_3$, $OCF_3$, $N(CH_3)_2$, $NHCOCH_3$, aryl, $CO_2CH_3$, $CONH_2$, $C_1$-$C_4$ alkyl, $(CF_2)_nF$ wherein n=1-4, Cl, Br, I, F, $O(CH_2)_nH$ wherein n=1-4, $NO_2$, $NH_2$, $NHCOR^4$, $CO_2H$, $CO_2R^4$, $CONHR^4$, amyl, thioether, $SR^6$, $S(O)R^6$, $SO_2R^6$, $SO_2NR^6R^7$; wherein $R^4$ has the definition given above; wherein $R^6$ is H, $C_1$-$C_4$ alkyl or perfluoroalkyl, aryl, heteroaryl, or optionally substituted allyl, arylmethyl, alkynyl, alkenyl; wherein $R^7$ is H, $C_1$-$C_4$ alkyl or perfluoroalkyl, aryl, heteroaryl, optionally substituted allyl, arylmethyl, $OR^8$ or $NHR^8$; wherein $R^8$ is H, $C_1$-$C_6$ alkyl or perfluoroalkyl, aryl, heteroaryl, optionally substituted allyl, arylmethyl, $SO_2R^6$ or $S(O)R^6$, wherein $R^6$ has the definition given above; and wherein $R^5$ can be in either the E or Z configuration in relation to the 17α-position of the address unit. In one aspect, a probe of a compound of the invention such as, for example, the antiestrogen compounds above, can comprise one or more substituents (e.g., additional or alternative) as a detectable marker (label, marker or tag). Preferably, a probe of the invention comprises one or more of $R^1$, $R^2$, $R^3$, $R^4$, $R^5$, R6, $R^7$, $R^8$ and $R^9$, each of which can independently comprise (for example, $R^1$ can be $^{131}I$ or $CH_2$—$CH_2$—$^{131}I$) $^{131}I$, $^{125}I$, $^3H$, $^{123}I$, $^{18}F$, $^{19}F$, $^{11}C$, $^{75}Br$, $^{13}C$, $^{13}N$, $^{15}O$, $^{76}Br$, $CH_2$—$CH_2$-label, O—$CH_2$—$CH_2$-label, $CH_2$—$CH_2$—$CH_2$-label, O—$CH_2$—$CH_2$—$CH_2$-label, —[$OCH_2$—$CH_2$]$_n$-label, O—$CH_2$—CH=CH-label, N—$CH_2$—CH=CH-label in which "label" can independently be $^{131}I$, $^{124}I$, $^{125}I$, $^3H$, $^{123}I$, $^{18}F$, $^{19}F$, $^{11}C$, $^{75}Br$, $^{13}C$, $^{13}N$, $^{15}O$, $^{76}Br$, $^{11}C$ or $^{13}C$, or $^{11}C$ or $^{13}C$ can be a label (mark or tag) as a substituent of a lower alkyl group, $(CH_2)_nOR$, $CL_3$, $CH_2$—$CH_2$-L, O—$CH_2$—$CH_2$-L, $CH_2$—$CH_2$—$CH_2$-L, O—$CH_2$—$CH_2$—$CH_2$-L, CN, (C=O)—R, (C=O)N(R)$_2$, O(CO)R, OR, COOR, aryl, CR=CR-aryl or $CR_2$—$CR_2$-aryl in which L can be a halogen (for example, $^{13}CH_2$—$CH_2$—F) and R can be H, F, Cl, Br, I or a lower alkyl group.

In another aspect, the present invention provides a compound that is an antiandrogen compound having the structural formula, in the address/message construct described below:

a) an address unit having one of the following different structures:

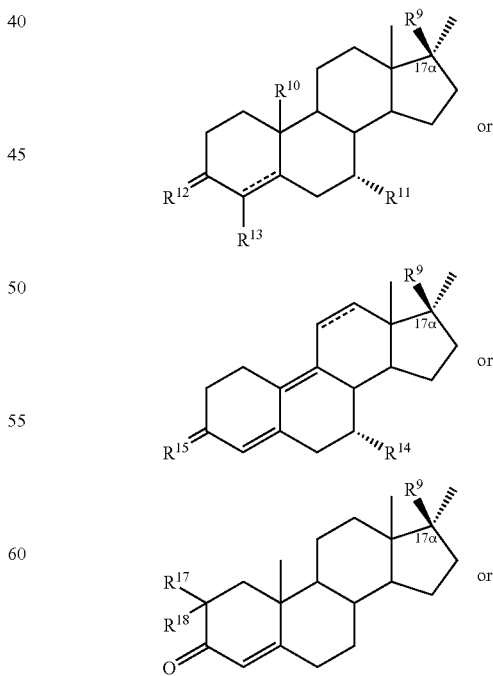

-continued

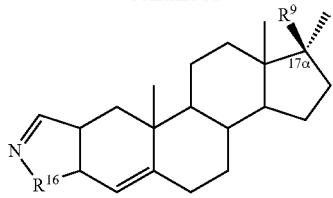

wherein:
$R^9$ is H, OH, $NH_2$;
$R^{10}$ is H, $CH_3$;
$R^{11}$ is H, $C_1$-$C_4$ alkyl;
$R^{12}$ is O, (H, OH);
$R^{13}$ is H, OH, Cl, Br, I, $CH_3$;
$R^{14}$ is H, $C_1$-$C_4$ alkyl;
$R^{15}$ is 0, (H, OH);
$R^{16}$ is O, NH;
$R^{17}$ through $R^{18}$ each independently is H, $CH_3$; and, attached to the 17α-position of the address unit,
and
b) a message unit having the structure:

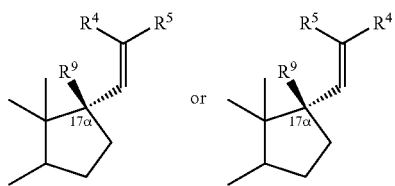

wherein:
$R^4$ is H, alkyl ($C_1$-$C_4$)
$R^5$ is aryl, heteroaryl, fused aryl, —CO-aryl, CO-fused aryl, —CO-heteroaryl, —CO-fused heteroaryl, biaryl, CO-biaryl, ether-linked aryls, ether-linked heteroaryls, amine-linked aryls, amine-linked heteroaryls, aminoalkoxy arene hybrid, peptidyl hybrid, wherein any aryl, heteroaryl, fused aryl, fused heteroaryl, —CO-aryl, CO-fused aryl, —CO-heteroaryl, —CO-fused heteroaryl, biaryl, CO-biaryl, ether-linked aryls, ether-linked heteroaryls, amine-linked aryls, amine-linked heteroaryls, aminoalkoxy arene hybrid, and peptidyl hybrid may optionally be substituted, independently, with H, $CH_3$, OH, $OCH_3$, $OCF_3$, $N(CH_3)_2$, $NHCOCH_3$, aryl, $CO_2CH_3$, $CONH_2$, $C_1$-$C_4$ alkyl, $(CF_2)_nF$ wherein n=1-4, Cl, Br, I, F, $O(CH_2)_nH$ wherein n=1-4, $NO_2$, $NH_2$, $NHCOR^4$, $CO_2H$, $CO_2R^4$, $CONHR^4$, amyl, thioether, $SR^6$, $S(O)R^6$, $SO_2R^6$, $SO_2NR^6R^7$; wherein $R^4$ has the definition given above; wherein $R^6$ is H, $C_1$-$C_4$ alkyl or perfluoroalkyl, aryl, heteroaryl, or optionally substituted allyl, arylmethyl, alkynyl, alkenyl; wherein $R^7$ is H, $C_1$-$C_4$ alkyl or perfluoroalkyl, aryl, heteroaryl, optionally substituted allyl, arylmethyl, $OR^8$ or $NHR^8$; wherein $R^8$ is H, $C_1$-$C_6$ alkyl or perfluoroalkyl, aryl, heteroaryl, optionally substituted allyl or arylmethyl, $SO_2R^6$ or $S(O)R^6$, wherein $R^6$ has the definition given above; and
wherein $R^5$ can be in either the E or Z configuration in relation to the 17α-position of the address unit. In one aspect, a probe of a compound of the invention such as, for example, the antiandrogen compounds above, can comprise one or more substituents (e.g., additional or alternative) as a detectable marker (label, marker or tag). Preferably, a probe of the invention comprises one or more of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$ and $R^{18}$, each of which can independently comprise (for example, $R^1$ can be $^{131}$I or $CH_2$—$CH_2$—$^{131}$I) $^{131}$I, $^{124}$I, $^{125}$I, $^3$H, $^{123}$I, $^{18}$F, $^{19}$F, $^{11}$C, $^{75}$Br, $^{13}$C, $^{13}$N, $^{15}$O, $^{76}$Br, $CH_2$—$CH_2$-label, O—$CH_2$—$CH_2$-label, $CH_2$—$CH_2$—$CH_2$-label, O—$CH_2$—$CH_2$—$CH_2$-label, —[$OCH_2$—$CH_2$]$_n$-label, O—$CH_2$—CH=CH— label, N—$CH_2$—CH=CH-label in which "label" can independently be $^{131}$I, $^{124}$I, $^{125}$I, $^3$H, $^{123}$I, $^{18}$F, $^{19}$F, $^{11}$C, $^{75}$Br, $^{13}$C, $^{13}$N, $^{15}$O, $^{76}$Br, $^{11}$C or $^{13}$C, can be a label (mark or tag) as a substituent of a lower alkyl group, $(CH_2)_nOR$, $CL_3$, $CH_2$—$CH_2$-L, O—$CH_2$—$CH_2$-L, $CH_2$—$CH_2$—$CH_2$-L, O—$CH_2$—$CH_2$—$CH_2$-L, CN, (C=O)—R, (C=O)N(R)$_2$, O(CO)R, OR, COOR, aryl, CR=CR-aryl or $CR_2$—$CR_2$-aryl in which L can be a halogen (for example, $^{13}CH_2$—$CH_2$—F) and R can be H, F, Cl, Br, I or a lower alkyl group.

A label, detectable label, radiolabel, tag, marker, detectable marker, tracer, radiotracer or equivalent term as generally understood by those of ordinary skill in the art can represent any substituent (group, moiety, position) suitable for imaging, detecting and/or assaying (for example, identifying, diagnosing, evaluating, detecting and/or quantitating) in vivo or in vitro. For example, a probe of the invention can comprise labels, radiolabels, tags, markers, detectable markers, tracers, radiotracers or equivalent terms suitable for in vivo or in vitro detection via radioscintigraphy, magnetic resonance imaging (MRI), assays, chemilumensence, near infrared luminescence, fluorescence, spectroscopy, gamma imaging, magnetic resonance imaging, magnetic resonance spectroscopy, fluorescence spectroscopy, SPECT, computed tomography (CT scan), positron emission tomography (PET). Suitable labels, radiolabels, tags, markers, detectable markers, tracers, radiotracers or equivalent terms are known by those skilled in the art and can include, for example, radioisotopes, radionuclides, isotopes, fluorescent groups, biotin (in conjunction with streptavidin complexation) or photoaffinity groups. Preferably, a label, detectable label, radiolabel, tag, marker, detectable marker, tracer, radiotracer of a probe of the invention can comprise $^{131}$I, $^{124}$I, $^{125}$I, $^3$H, $^{123}$I, $^{18}$F, $^{19}$F, $^{11}$C, $^{75}$Br, $^{13}$C, $^{13}$N, $^{15}$O, $^{76}$Br, $CH_2$—$CH_2$-Q, O—$CH_2$—$CH_2$-Q, $CH_2$—$CH_2$—$CH_2$-Q or O—$CH_2$—$CH_2$—$CH_2$-Q, —[$OCH_2$—$CH_2$]$_n$-Q, O—$CH_2$—CH=CH-Q, N—$CH_2$—CH=CH-Q in which "Q" can independently be $^{131}$I, $^{124}$I, $^{125}$I, $^3$H, $^{123}$I, $^{18}$F, $^{19}$F, $^{11}$C, $^{75}$Br, $^{13}$C, $^{13}$N, $^{15}$O, $^{76}$Br, $^{11}$C or $^{13}$C can be a label, detectable label, radiolabel, tag, marker, detectable marker, tracer, radiotracer as a substituent of a lower alkyl group, $(CH_2)_nOR$, $CL_3$, $CH_2$—$CH_2$-L, O—$CH_2$—$CH_2$-L, $CH_2$—$CH_2$—$CH_2$-L, O—$CH_2$—$CH_2$—$CH_2$-L, CN, (C=O)—R, (C=O)N(R)$_2$, O(CO)R, OR, COOR, aryl, CR=CR-aryl or $CR_2$—$CR_2$-aryl in which L can be a halogen (for example, $^{13}CH_2$—$CH_2$—F) and R can be H, F, Cl, Br, I or a lower alkyl group. "Photoaffinity group" or "photoaffinity labeled" can refer to a substituent on a compound or probe of the invention, which can be activated by photolysis at an appropriate wavelength to undergo a cross-linking photochemical reaction with a macromolecule associated therewith. An example of a photoaffinity group is a benzophenone substituent.

Suitable radioisotopes are known to those skilled in the art and include, for example, isotopes of halogens (such as chlorine, fluorine, bromine and iodine) and metals including technetium and indium. Exemplary labels, radiolabels, tags, markers, detectable markers, tracers, radiotracers can also include $^3$H, $^{11}$C, $^{14}$C, $^{18}$F, $^{32}$S, $^{35}$S, $^{123}$I, $^{125}$I, $^{131}$I, $^{124}$I, $^{19}$F, $^{75}$Br, $^{13}$C, $^{13}$N, $^{15}$O, $^{76}$Br. The probes of the invention may be labeled (radiolabeled, tagged, marked, detectably marked, traced or radiotraced) either directly (that is, by incorporating the label directly into a compound of the invention) or indirectly (that is, by incorporating the label into a compound of the invention through a chelating agent, where the chelating agent has been incorporated into the compound). Furthermore, a label for a probe can be included as an additional substituent (group, moiety, position) to a compound of the invention or as an alternative substituent for any substituents that are present. For example, a label included as an additional substituent to the group —$CH_2$—CH=$CH_2$ of a compound of the invention can be $CH_2$—$CH_2$—$CH_2$—$^{131}$I. Moreover, a label provided as an alternative substituent for one or more substituents present for a compound of the invention can, by way of example, include $CH_2$—$CH_2$—$CH_3$ to $CH_2$—$CH_2$—$CH_2$—$^{131}$I, or —$CH_2$—CH=CH—I to —$CH_2$—CH=CH—$^{123}$I. A label, detectable label, radiolabel, tag, marker, detectable marker, tracer or radiotracer may appear at any substituent (group, moiety, position) on a compound or probe of the invention.

In one aspect, labeling can be isotopic or nonisotopic. With isotopic labeling, one substituent (group, moiety, position) already present in a compound of the invention can be substituted with (exchanged for) a radioisotope or isotope. With nonisotopic labeling, a radioisotope or isotope can be added to a compound of the invention without substituting with (exchanging for) an already existing group. Direct and indirect labeled compounds as well as isotopic and nonisotopic labeled compounds are contemplated by a compound and/or probe of the invention comprising one or more labels, radiolabels, tags, markers, detectable markers, tracers or radiotracers and equivalents thereof. Preferably, a label, detectable label, radiolabel, tag, marker, detectable marker, tracer or radiotracer can be reasonably stable, both chemically and metabolically, applying recognized standards in the art. Moreover, although the compounds or probes of the invention may be labeled in any fashion (for example, via conventional techniques) with a variety of different substituents, as those skilled in the art can appreciate, such labeling may be performed in a manner so as to retain the affinity (binding affinity), for example, a high-affinity, and a specific or preferential nature of binding to a tissue or receptor (for example, an estrogen receptor and/or androgen receptor as well as estrogen-like and/or androgen-like receptors) or proteins, precursors, portions, fragments and/or peptides. In one aspect, a receptor can be present in a tissue with a subject. In one aspect, the affinity and specificity of a compound of the invention is not significantly affected by labeling to comprise a probe. By not significantly affected, affinity and specificity may not be affected by more than, for example, about 3 log units (preferably, not more than, for example, about 2 log units or, more preferably, not more than, for example, about 1 log unit). Furthermore, by not significantly affected, affinity and specificity may not be affected by more than, for example, about 500% (preferably, not more than, for example, about 250% or, more preferably, affinity and specificity may not be affected at all).

In one aspect, a compound of the invention, such as, for example, an antiestrogen compound, can also be substituted at any position of the message or address unit by a detectable marker to comprise a probe for detection and imaging type applications, preferably, in vivo.

In one aspect, the invention relates to an in vivo or in vitro method for detecting at least one receptor. For example, the receptor can be in tissue comprising estrogen receptors and/or androgen receptors as well as estrogen-like and/or androgen-like receptors. The invention also relates to an in vivo or in vitro method for detecting in a subject one or more tissues comprising one or more receptors. For example, a method of the invention can comprise administering to a subject thought to be of risk for or suffering from a hormone-responsive disorder (for example, estrogen and androgen mediated disorders), a detectable quantity or effective amount of a compound or probe thereof (or analogs, salts, pharmaceutical compositions, derivatives, prodrugs or racemic mixtures thereof) and detecting the binding of the compound or probe thereof in a tissue (for example, a tissue comprising at least one receptor including, but not limited to, an estrogen receptor and/or androgen receptor as well as estrogen-like and/or androgen-like receptors). The invention also relates to compounds and probes that can target estrogen receptors and/or androgen receptors (and/or estrogen-like and/or androgen-like receptors) in vivo or in vitro. The compounds and/or probes of the invention can be administered to a subject in effective amounts for therapeutic (for example, treating or preventing a hormone-responsive disorder) or imaging (for example, identifying, diagnosing, evaluating, detecting and/or quantitating estrogen receptors and/or androgen receptors or a hormone-responsive disorder) applications.

The invention also relates to an in vivo method for detecting estrogen receptors and/or androgen receptors (and/or estrogen-like and/or androgen-like receptors) in a subject. Preferably, the invention can comprise an in vivo method for detecting tissues. Exemplary tissues can comprise at least one receptor including, but not limited to, estrogen receptors and/or androgen receptors as well as estrogen-like and/or androgen-like receptors. For example, the method can comprise administering a detectable quantity (effective amount) of a labeled compound of the invention and detecting the binding of the compound to a tissue or receptor (for example, a hormone receptor or hormone-like receptor) thereof in the subject. In one aspect, the estrogen receptor and/or androgen receptor (and/or estrogen-like and/or androgen-like receptors) is located in the brain of a subject. The subject can be suffering from or suspected of suffering from a disease associated with a hormone-responsive disorder (for example, estrogen and androgen mediated disorders) such as, but are not limited to, osteoporosis, endometriosis, breast cancer, benign breast cancer, uterine cancer, ovarian cancer, polycystic ovarian disease, prostate cancer, benign prostatic hyperplasia (BPH), cardiac diseases, coronary artery disease, acne, seborrhea, alopecia, hirsutism, male pattern baldness, and infertility.

In one aspect, detection can be performed via a scintigraphic approach. For example, detection accomplished by gamma imaging, magnetic resonance imaging, magnetic resonance spectroscopy and/or fluorescence spectroscopy. Preferably, the scintigraphic approach for detecting a probe of the invention comprises either PET or SPECT imaging and standard protocols used in conjunction therewith. The compound or probe of the invention can also be administered as a pharmaceutical composition. Exemplary pharmaceutical compositions comprise a compound or probe of the invention and a pharmaceutically acceptable carrier. Preferably, administering a compound or probe of the invention to a subject in need thereof can be by intravenous injection or bolus intravenous injection. Other exemplary routes of administration can include oral, rectal, parenteral (intramuscular or subcutaneous), intracisternal, intravaginal, intraperitoneal, local (powders, ointments or drops) or as a buccal or nasal spray as well as ocular drops.

A method of the invention can also comprise determining a ratio (for example, a tissue or receptor uptake ratio). In one aspect, the ratio can be that of the radioactive uptake of a compound or probe of the invention to a brain area other than the cerebellum as compared to the radioactive uptake of the compound or probe to the cerebellum. In one aspect, the ratio can be that of the radioactive uptake of a compound or probe of the invention to a tissue or receptor (for example, a hormone receptor) comprising area (for example, breast or prostate tissue) as compared to another tissue or receptor comprising area (for example, a non-diseased area such as, but not limited to breast tissue, within the same subject or another non-diseased subject). The method can comprise comparing the ratio from a subject suffering from or thought to be at risk for a disease associated with a hormone-responsive disorder to that of a healthy (non-diseased) subject. In another aspect, the invention relates to a method of inhibiting cell proliferation in a patient. For example, the cell proliferation can be associated with a hormone-responsive disorder or malady. For example, the method comprises administering to a subject having, suspected of having and/or at risk for a disease or malady associated with a hormone-responsive disorder, a compound or probe of the invention in an effective amount.

Inhibition of cell proliferation can include compounds or probes of the invention (as well as analogs, salts, pharmaceutical compositions, derivatives, prodrugs or racemic mixtures thereof) that modulate or inhibit cell proliferation. Inhibitors of cell proliferation are compounds or probes that can, preferably, block cancer cell proliferation (for example, antagonism) without eliminating certain beneficial effects (for example, bone density). In one aspect, inhibitors of cell proliferation (for example, a compound or probe of the invention) can bind to a tissue or receptor of interest and, for example, partially or totally block stimulation, decrease, prevent, delay activation, inactivate, desensitize, or down regulate any activities thereof. Preferably, a compound or probe of the invention can be used to inhibit cell proliferation such that cell proliferation is modulated (for example, inhibited, decreased, slowed or prevented) to some extent. For example, cell proliferation can be inhibited by administration of a compound or probe of the invention to some biologically or medically relevant extent when compared to non-administration or non-use (non-therapy) of the compound or probe. By way of example, cell proliferation inhibition by administering a compound or probe to a patient suffering from or believed to be at risk of suffering from a hormone-responsive disorder, can mean inhibiting the extent of cell proliferation by less than 100%, for example, 90%, 80%, 70%, 60%, 50%, 40%, 30%, 20%, 10% or less, as compared to cell proliferation in a patient suffering from or believed to be at risk of suffering from a hormone-responsive disorder, without administration or a therapy protocol involving the compound or probe. Cell proliferation can be measured by conventional techniques routine to those of ordinary skill in the art. It is also appreciated that the various modes of inhibiting cell proliferation can mean "substantial" inhibition, which includes total but also less than total inhibition.

A method of the invention relates to inhibiting cell proliferation associated with a hormone-responsive disorder. Preferably, the method comprises administering to a subject in need thereof a compound or probe of the invention (or analogs, salts, pharmaceutical compositions, derivatives, prodrugs or racemic mixtures thereof) in an effective amount, for example, an amount capable of inhibiting cell proliferation associated with a hormone-responsive disorder.

In one aspect, the invention relates to a method for detecting a tissue or at least one receptor of interest in biopsy or post-mortem subject tissue (in vitro). The method comprises incubating formalin-fixed tissue with a solution of a compound or probe of the invention to allow for binding with the at least one tissue or receptor (for example, a hormone receptor) or formation of a labeled tissue or receptor and detecting the compound, probe or labeled tissue or receptor. In one aspect, a receptor can be a receptor rich area such as a tissue (for example, a diseased tissue from, but not limited to, a patient suffering from a hormone-responsive disorder). The solution can be composed of 25 to 100% ethanol (with the remainder being water) saturated with the compound or probe of the invention. Preferably, in vitro detection can be accomplished by microscopic techniques. Examples of microscopic techniques include bright field, fluorescence, laser confocal or cross-polarization microscopy.

A tissue (for example, tumor) can be considered hormone-responsive, which may mean, for example, the tissue contains elevated levels (rich) of a hormone receptor. In one aspect, a hormone-responsive disorder is characterized in a tissue that contains elevated levels of a hormone receptor and cell proliferation (for example, tumor cell proliferation) is stimulated by circulating hormones. For example, the hormone receptor can be an estrogen, androgen, estrogen-like and/or androgen-like receptor (or proteins, precursors, portions, fragments, tissues and/or peptides thereof). Preferably, a tissue that contains elevated levels of a hormone receptor can be considered as a "rich" tissue or receptor rich tissue. A rich tissue can be one that contains more (total percentage, ratio, count or the like) hormone receptors than a tissue without an elevated level of the receptor. For example, a rich tissue can contain more than 90%, 80%, 70%, 60%, 50%, 40%, 30%, 20%, 10% of the total receptor count for a non-elevated tissue. Determining the level of receptors in a tissue is routine to those of ordinary skill in the art using conventional techniques. In one aspect, a tissue containing elevated levels of a hormone receptor can be a tissue indicative or a disease state, for example, a hormone-responsive disease state. For example, a hormone receptor rich tissue can be a found in a patient suffering from a hormone-responsive disorder. Exemplary hormone-responsive disorders include osteoporosis, endometriosis, breast cancer, benign breast cancer, uterine cancer, ovarian cancer, polycystic ovarian disease, prostate cancer, benign prostatic hyperplasia (BPH), cardiac diseases, coronary artery disease, acne, seborrhea, alopecia, hirsutism, male pattern baldness, and infertility. In one aspect, osteoporosis, endometriosis, breast cancer, benign breast cancer, uterine cancer, ovarian cancer, polycystic ovarian disease, prostate cancer, benign prostatic hyperplasia (BPH), cardiac diseases, coronary artery disease, acne, seborrhea, alopecia, hirsutism, male pattern baldness, and infertility can be characterized by tissues in a patient that contain elevated levels of a hormone receptor and/or and cell proliferation is stimulated by circulating hormones.

The invention also relates to a method of distinguishing a tissue indicative of a hormone-responsive disorder from normal tissue. For example, the tissue can comprise brain tissue. Preferably, the method comprises incubating (separately) weighed tissue from a diseased or thought to be disease tissue and another (preferably non-diseased) area of the same subject, suspected of having a hormone-responsive disorder, with a compound or probe of the invention so that binding with receptors in the tissues (areas) occurs. The method also comprises quantifying the amount of receptors bound to the compound or probe by separating the tissue-bound from the tissue-unbound, quantifying the tissue-bound and converting the units of tissue-bound (labeled tissue) to units of micrograms of receptor per 100 mg of tissue by comparison with a standard. The method can also comprise calculating a ratio of the amount of receptors in the non-disease area to the amount of receptors in the diseased area. Optionally, an amount of receptors in tissue from the subject suspected of having a hormone-responsive disorder can be compared to the amount of receptors in the tissue from normal subjects. By way of example only, the above approaches can also be used to characterize a tissue with an elevated level (rich) of a hormone receptor. For example, a rich tissue can contain an amount of receptors more than 90%, 80%, 70%, 60%, 50%, 40%, 30%, 20%, 10% of that for a non-elevated tissue type from, for example, a non-diseased subject.

The invention also relates to a method of distinguishing brain tissue indicative of a hormone-responsive disorder from normal tissue comprising incubating (separately) homogenates of weighed tissue from the cerebellum and another area of the same brain other than the cerebellum, from a subject suspected of having a hormone responsive disorder, with a compound or probe of the invention so that binding with receptors of interest in the tissues occurs. The method also comprises quantifying the amount of receptors bound to the compound or probe by separating the tissue-bound from the tissue-unbound, quantifying the tissue-bound and converting the units of tissue-bound (labeled deposit) to units of micrograms of receptors per 100 mg of tissue by comparison with a standard. The method can also comprise calculating a ratio of the amount of receptors in the area of the brain other than the cerebellum to the amount of receptors in the cerebellum and comparing the ratio of the amount of receptors in tissue from the subject suspected of having hormone-responsive disorder with ratios for the amount of receptors in the tissue from normal subjects. In one aspect, the method comprises determining the presence of a hormone responsive disorder if the ratio from the brain of a subject suspected of having the disease state is above about 40%, 50%, 60%, 70%, 80% or 90% (preferably, for example, above 50% and, more preferably, for example, above 90%) of the ratios obtained from the brains of normal subjects.

The invention also relates to methods for preparing compounds of the invention. In one aspect, one or more of the compounds can be modified to be a probe of the invention. The probes of the invention are particularly useful for the in vivo or in vitro diagnosis and/or study of the progression or regression of disease states or maladies in a patient. Exemplary disease states or maladies include, for example, osteoporosis, endometriosis, breast cancer, benign breast cancer, uterine cancer, ovarian cancer, polycystic ovarian disease, prostate cancer, benign prostatic hyperplasia (BPH), cardiac diseases, coronary artery disease, acne, seborrhea, alopecia, hirsutism, male pattern baldness, and infertility. A probe may also comprise one or more compounds of the invention and at least one detectable marker, tag or label such as, for example, a radionuclide, radioisotope or isotope. The selection of detectable markers, tags or labels for a probe of the invention can vary depending on the particular modality chosen for in vivo or in vitro imaging, the disease state or malady being diagnosed or studied or the route of administration of the probe.

The invention relates to an in vivo or in vitro method for detecting in a subject one or more receptors. In one aspect, the receptors can comprise one or more estrogen and/or the androgen receptors and/or estrogen-like and/or androgen-like receptors. The method comprises administering to a subject suffering from a disease associated with a hormone-responsive disorder, a detectable quantity (effective amount) of a compound or probe of the invention (or analogs, salts, pharmaceutical compositions, derivatives, prodrugs or racemic mixtures thereof). For example, a probe of the invention can comprise one or more substituents as a label (radiolabel, marker or tag). Preferably, a probe of the invention comprises one or more radionuclides, radioisotopes or isotopes (labels). Examples of labels for a probe of the invention include, but are not limited to $^{131}I$, $^{124}I$, $^{125}I$, $^{3}H$, $^{123}I$, $^{18}F$, $^{19}F$, $^{11}C$, $^{75}Br$, $^{13}C$, $^{13}N$, $^{15}O$, $^{76}Br$. The method also comprises detecting the binding of the compound or probe to (with or in) one or more tissue such as, for example, tissues comprising estrogen or the androgen receptors and/or estrogen-like and/or androgen-like receptors (preferably, tissues rich in estrogen or the androgen receptors or estrogen-like and/or androgen-like receptors). A tissue can comprise receptors or proteins, precursors, portions, fragments and peptides thereof.

Moreover, the invention relates to an in vivo method for detecting at least one tissue or receptor (for example, a hormone receptor). For example, the method can comprise administering to a subject suffering from or thought to be at risk of suffering from a disease associated with a hormone responsive disorder, a detectable quantity (effective amount) of a compound or probe of the invention (or analogs, salts, pharmaceutical compositions, derivatives, prodrugs or racemic mixtures thereof). In one aspect, the compound or probe binds to the tissue or receptor (for example, a hormone receptor). The method also comprises irradiating the subject and collecting imaging data emitted by the compound or probe. Optionally, the method comprises processing the imaging data in order to diagnose and/or study of the progression or regression (when accompanied by a therapy protocol) of disease states or maladies in a subject.

The invention also relates to the use of a compound or probe of the invention for detecting tissues or receptors in a subject suffering from a disease associated with a hormone-responsive disorder. The invention further relates to the use of a compound or probe of the invention in the preparation of a medicament for use in the detection of tissues or receptors in a subject. In one aspect, one or more tissue or receptors are located in the brain, breasts or prostate. For example, a subject can be suffering from a hormone-responsive disorder characterized by receptor rich areas in regions of the brain, breasts or prostate. Other organs or tissues that can comprise estrogen or the androgen receptors (and/or estrogen-like and/or androgen-like receptors) and are able to be studied, detected or imaged using the compounds or probes of the invention as well as methods, kits, assays or uses thereof. Preferably, a compound or probe of the invention can be detected via approaches that include gamma imaging, magnetic resonance imaging, magnetic resonance spectroscopy or fluorescence spectroscopy.

In one aspect, the invention relates to a method of diagnosing a hormone-responsive disorder such as, for example, an estrogen or androgen mediated disorder. In another aspect, detection can be by quasi-elastic light scattering or spectroscopic techniques (for example, Raman), although radioscintigraphy, magnetic resonance imaging (MRI), assays, chemilumensence, near infrared luminescence, fluorescence, gamma imaging, magnetic resonance imaging, magnetic resonance spectroscopy, fluorescence spectroscopy, SPECT, computed tomography (CT scan) and/or positron emission tomography (PET) can also be used.

In one aspect, the invention relates to an in vivo method for detecting hormone receptors in a subject comprising administering an effective amount of a probe or composition or the invention (or analogs, salts, derivatives, prodrugs or racemic mixtures thereof) to the subject and detecting the binding of the probe or composition to at least one hormone receptor in the subject. In another aspect, the invention provides an in vivo method for detecting hormone receptor in a subject comprising administering an effective amount of a probe or composition or the invention (or analogs, salts, derivatives, prodrugs or racemic mixtures thereof) to the subject having or suspected of having a hormone-responsive disorder and detecting the binding of the probe or composition to at least one hormone receptor in the subject.

For example, the hormone receptor is located in the brain, breast or prostate tissue of the subject. The hormone-responsive disorder can also be osteoporosis, endometriosis, breast cancer, benign breast cancer, uterine cancer, ovarian cancer, polycystic ovarian disease, prostate cancer, benign prostatic hyperplasia, coronary artery disease, acne, seborrhea, alopecia, hirsutism, male pattern baldness, or infertility. Detection for a method of the invention can also be by gamma imaging, magnetic resonance imaging, magnetic resonance spectroscopy or fluorescence spectroscopy. Preferably, detection by gamma imaging is PET or SPECT.

Examples of the combined structural formula for the compounds of the present invention that includes both the address and the message units are as follows:

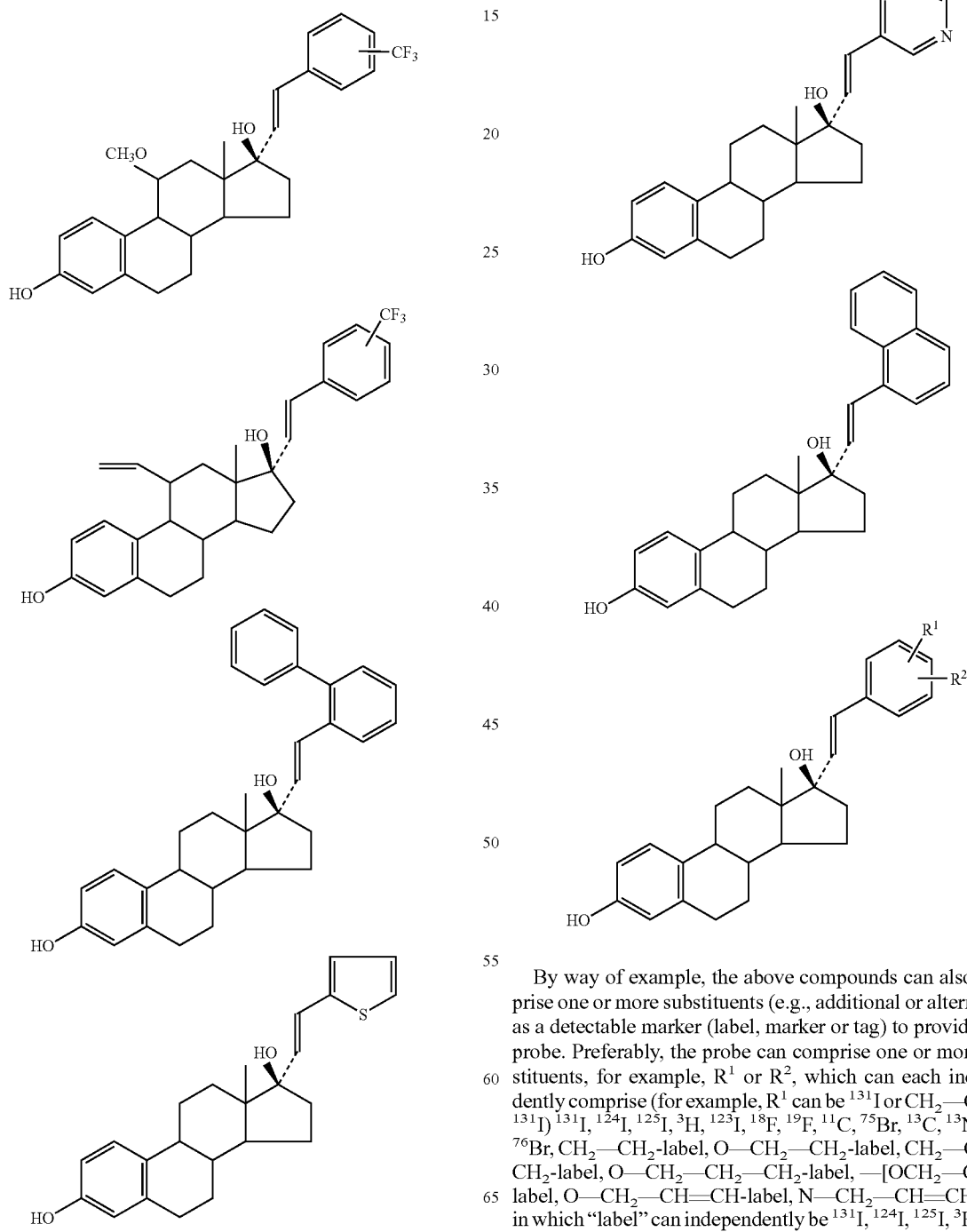

By way of example, the above compounds can also comprise one or more substituents (e.g., additional or alternative) as a detectable marker (label, marker or tag) to provide for a probe. Preferably, the probe can comprise one or more substituents, for example, $R^1$ or $R^2$, which can each independently comprise (for example, $R^1$ can be $^{131}$I or $CH_2$—$CH_2$—$^{131}$I) $^{131}$I, $^{124}$I, $^{125}$I, $^3$H, $^{123}$I, $^{18}$F, $^{19}$F, $^{11}$C, $^{75}$Br, $^{13}$C, $^{13}$N, $^{15}$O, $^{76}$Br, $CH_2$—$CH_2$-label, O—$CH_2$—$CH_2$-label, $CH_2$—$CH_2$—$CH_2$-label, O—$CH_2$—$CH_2$—$CH_2$-label, —[$OCH_2$—$CH_2$]$_n$-label, O—$CH_2$—CH=CH-label, N—$CH_2$—CH=CH-label in which "label" can independently be $^{131}$I, $^{124}$I, $^{125}$I, $^3$H, $^{123}$I, $^{18}$F, $^{19}$F, $^{11}$C, $^{75}$Br, $^{13}$C, $^{13}$N, $^{15}$O, $^{76}$Br, $^{11}$C or $^{13}$C, or $^{11}$C or $^{13}$C can be a label (mark or tag) as a substituent of a lower alkyl group, $(CH_2)_nOR$, $CL_3$, $CH_2$—$CH_2$-L, O—$CH_2$—$CH_2$-L, $CH_2$—$CH_2$—$CH_2$-L, O—$CH_2$—$CH_2$—$CH_2$-L, CN, (C=O)—R, (C=O)N(R)$_2$, O(CO)R, OR, COOR, aryl, CR=CR-aryl or $CR_2$—$CR_2$-aryl in which L can be a halogen (for example, $^{13}CH_2$—$CH_2$—F) and R can be H, F, Cl, Br, I or a lower alkyl group.

In another aspect, the present invention provides a compound that is an antiandrogen compound having the structural formula, in the address/message construct described below:

a) an address unit having one of the following different structures:

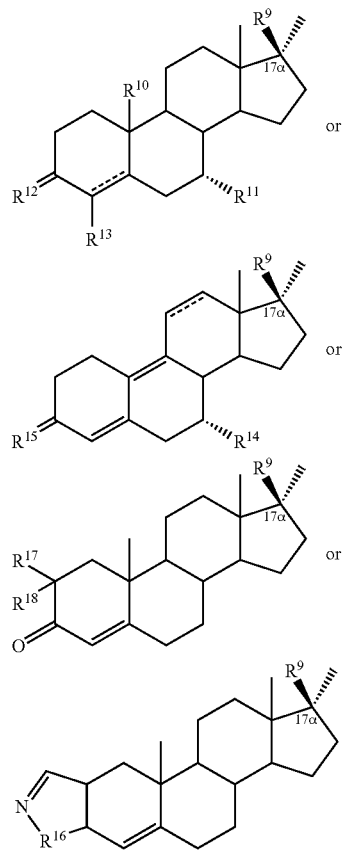

wherein:

$R^9$ is H, OH, NH$_2$, detectable marker and OH or NH$_2$ can optionally and independently each comprise (e.g., as an alternative or additional substituent) at least one detectable marker;

$R^{10}$ is H, CH$_3$, detectable marker and CH$_3$ can optionally comprise (e.g., as an alternative or additional substituent) at least one detectable marker;

$R^{11}$ is H, C$_1$-C$_4$ alkyl, detectable marker and C$_1$-C$_4$ alkyl can optionally comprise (e.g., as an alternative or additional substituent) at least one detectable marker;

$R^{12}$ is O, (H, OH), detectable marker and OH can optionally comprise (e.g., as an alternative or additional substituent) at least one detectable marker;

$R^{13}$ is H, OH, Cl, Br, I, CH$_3$, detectable marker and OH or CH$_3$ can optionally and independently each comprise (e.g., as an alternative or additional substituent) at least one detectable marker;

$R^{14}$ is H, C$_1$-C$_4$ alkyl, detectable marker and C$_1$-C$_4$ alkyl can optionally comprise (e.g., as an alternative or additional substituent) at least one detectable marker;

$R^{15}$ is O, (H, OH), detectable marker and OH can optionally comprise (e.g., as an alternative or additional substituent) at least one detectable marker;

$R^{16}$ is O, NH, detectable marker and NH can optionally comprise (e.g., as an alternative or additional substituent) at least one detectable marker;

$R^{17}$ through $R^{18}$ each independently is H, CH$_3$, detectable marker and CH$_3$ for $R^{17}$ or $R^{18}$ can optionally and independently each comprise (e.g., as an alternative or additional substituent) at least one detectable marker; and, attached to the 17α-position of the address unit, and b) a message unit having the structure:

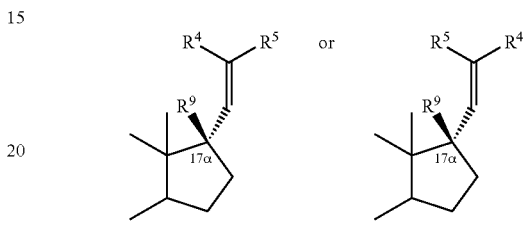

wherein:

$R^4$ is H, alkyl (C$_1$-C$_4$), detectable marker and alkyl (C$_1$-C$_4$) can optionally comprise (e.g., as an alternative or additional substituent) at least one detectable marker;

$R^5$ is aryl, heteroaryl, fused aryl, —CO-aryl, CO-fused aryl, —CO-heteroaryl, —CO-fused heteroaryl, biaryl, CO-biaryl, ether-linked aryls, ether-linked heteroaryls, amine-linked aryls, amine-linked heteroaryls, aminoalkoxy arene hybrid, detectable marker, peptidyl hybrid, wherein any aryl, heteroaryl, fused aryl, fused heteroaryl, —CO-aryl, CO-fused aryl, —CO-heteroaryl, —CO-fused heteroaryl, biaryl, CO-biaryl, ether-linked aryls, ether-linked heteroaryls, amine-linked aryls, amine-linked heteroaryls, aminoalkoxy arene hybrid, and peptidyl hybrid may optionally comprise (e.g., as an alternative or additional substituent), independently, at least one detectable marker, H, CH$_3$, OH, OCH$_3$, OCF$_3$, N(CH$_3$)$_2$, NHCOCH$_3$, aryl, CO$_2$CH$_3$, CONH$_2$, C$_1$-C$_4$ alkyl, (CF$_2$)$_n$F wherein n=1-4, Cl, Br, I, F, O(CH$_2$)$_n$H wherein n=1-4, NO$_2$, NH$_2$, NHCOR$^4$, CO$_2$H, CO$_2$R$^4$, CONHR$^4$, amyl, thioether, SR$^6$, S(O)R$^6$, SO$_2$R$^6$, SO$_2$NR$^6$R$^7$, and CH$_3$, OH, OCH$_3$, OCF$_3$, N(CH$_3$)$_2$, NHCOCH$_3$, aryl, CO$_2$CH$_3$, CONH$_2$, C$_1$-C$_4$ alkyl, (CF$_2$)$_n$F wherein n=1-4, Cl, Br, I, F, O(CH$_2$)$_n$H wherein n=1-4, NO$_2$, NH$_2$, NHCOR$^4$, CO$_2$H, CO$_2$R$^4$, CONHR$^4$, amyl, thioether, SR$^6$, S(O)R$^6$, SO$_2$R$^6$, SO$_2$NR$^6$R$^7$ can optionally and independently each comprise (e.g., as an alternative or additional substituent) at least one detectable marker; wherein $R^4$ has the definition given above; wherein $R^6$ is a detectable marker, H, C$_1$-C$_4$ alkyl or perfluoroalkyl, aryl, heteroaryl, or optionally substituted allyl, arylmethyl, alkynyl, alkenyl, wherein each of C$_1$-C$_4$ alkyl, perfluoroalkyl, aryl, heteroaryl, allyl, arylmethyl, alkynyl or alkenyl can optionally and independently comprise (e.g., as an alternative or additional substituent) at least one detectable marker; wherein $R^7$ is a detectable marker, H, C$_1$-C$_4$ alkyl, perfluoroalkyl, aryl, heteroaryl, optionally substituted allyl, arylmethyl, OR$^8$ or NHR$^8$, and wherein each of C$_1$-C$_4$ alkyl, perfluoroalkyl, aryl, heteroaryl, allyl, arylmethyl, OR$^8$ or NHR$^8$ can optionally and independently comprise (e.g., as an alternative or additional substituent) at least one detectable marker; and further wherein $R^8$ is a detectable marker, H, C$_1$-C$_6$ alkyl or perfluoroalkyl, aryl, heteroaryl, optionally substituted allyl or arylmethyl, SO$_2$R$^6$ or S(O)R$^6$, and C$_1$-C$_6$ alkyl, perfluoroalkyl, aryl, heteroaryl, allyl, arylmethyl, SO$_2$R$^6$ or S(O)R$^6$ can each optionally and independently comprise (e.g., as an alternative or additional substituent) at least one detectable marker, wherein $R^6$ has the definition given above; and wherein $R^5$ can be in either the E or Z configuration in relation to the 17α-position of the address unit. In one aspect, a compound of the invention, such as, for example, an anti-androgen compound, can also be substituted at any position of the message or address unit by a detectable marker to comprise a probe for detection and imaging type applications, preferably, in vivo.

Exemplary compounds containing both the address and the message units are as follows:

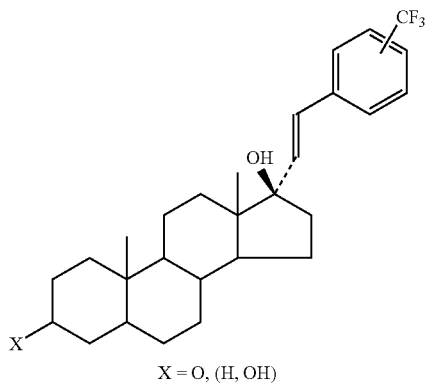

X = O, (H, OH)

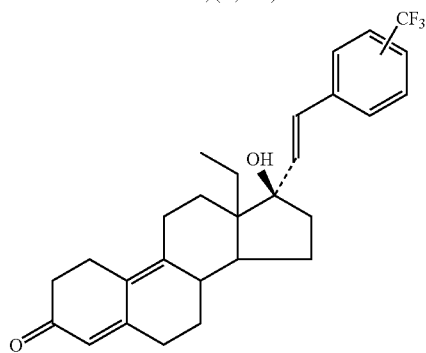

-continued

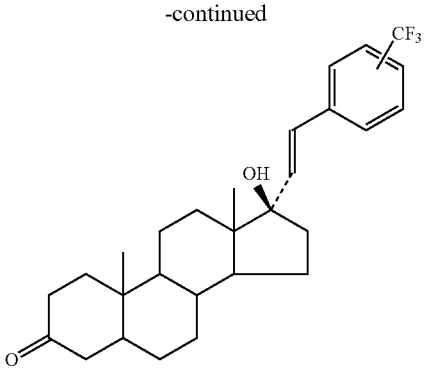

By way of example, the above compounds can also comprise one or more substituents (e.g., additional or alternative) as a detectable marker (label, marker or tag) to provide for a probe. Preferably, the probe can comprise one or more substituents, which can each independently comprise $^{131}I$, $^{124}I$, $^{125}I$, $^{3}H$, $^{123}I$, $^{18}F$, $^{19}F$, $^{11}C$, $^{75}Br$, $^{13}C$, $^{13}N$, $^{15}O$, $^{76}Br$, $CH_2$—$CH_2$-label, O—$CH_2$—$CH_2$-label, $CH_2$—$CH_2$—$CH_2$-label, O—$CH_2$—$CH_2$—$CH_2$-label, —[$OCH_2$—$CH_2$]$_n$-label, O—$CH_2$—CH=CH-label, N—$CH_2$—CH=CH-label in which "label" can independently be $^{131}I$, $^{124}I$, $^{125}I$, $^{3}H$, $^{123}I$, $^{18}F$, $^{19}F$, $^{11}C$, $^{75}Br$, $^{13}C$, $^{13}N$, $^{15}O$, $^{76}Br$, $^{11}C$ or $^{13}C$, or $^{11}C$ or $^{13}C$ can be a label (mark or tag) as a substituent of a lower alkyl group, $(CH_2)_n$OR, $CL_3$, $CH_2$—$CH_2$-L, O—$CH_2$—$CH_2$-L, $CH_2$—$CH_2$—$CH_2$-L, O—$CH_2$—$CH_2$—$CH_2$-L, CN, (C=O)—R, (C=O)N(R)$_2$, O(CO)R, OR, COOR, aryl, CR=CR-aryl or $CR_2$—$CR_2$-aryl in which L can be a halogen (for example, $^{13}CH_2$—$CH_2$—F) and R can be H, F, Cl, Br, I or a lower alkyl group. A probe of the invention can be used in imaging a subject suspected of having, having or at risk of having a disease including, but not limited to, a hormone responsive disorder. The disorder or disease state can also be symptomatic or asymptomatic.

Exemplary $R^5$ groups of the present invention are as follows:

TABLE 1

EXEMPLARY $R^5$ GROUPS

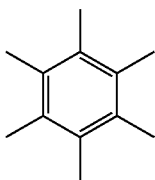 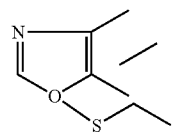

 

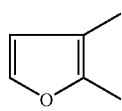 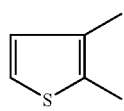

TABLE 1-continued
EXEMPLARY R⁵ GROUPS
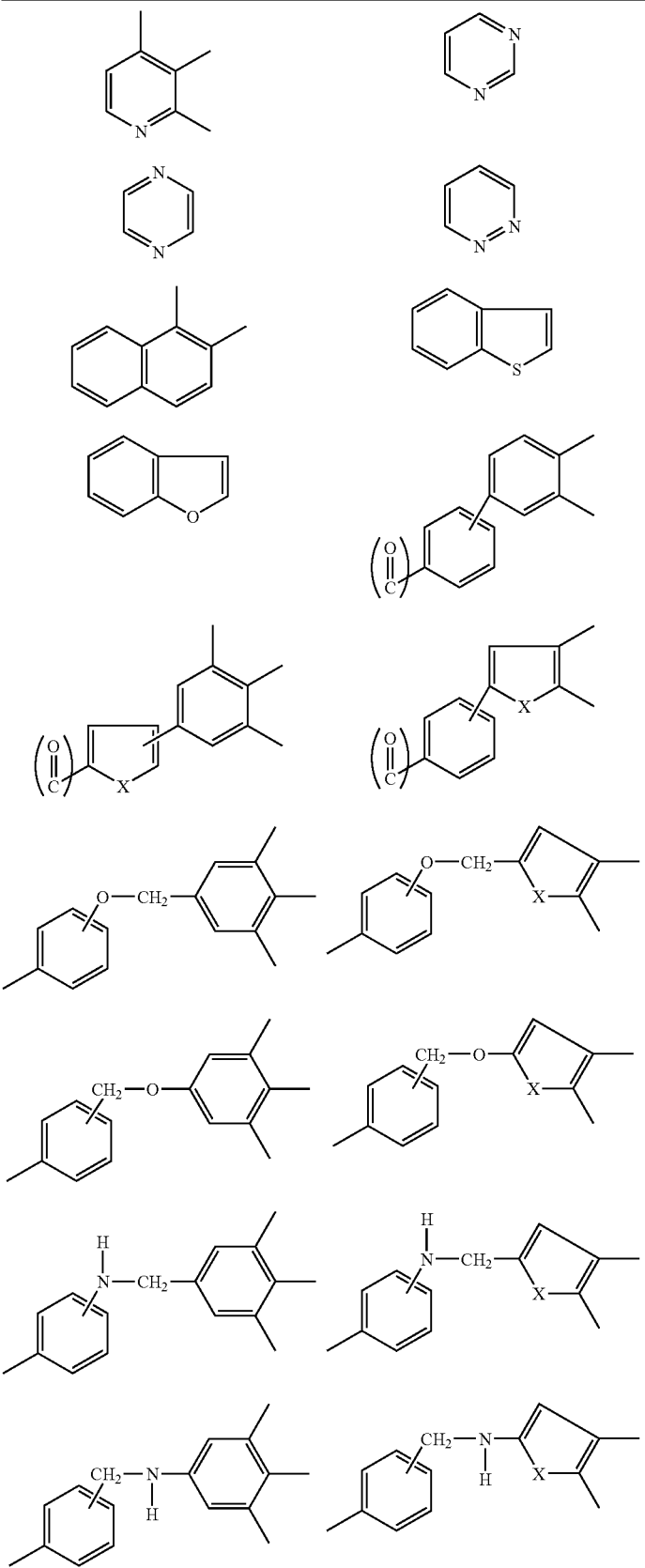

TABLE 1-continued

EXEMPLARY R⁵ GROUPS

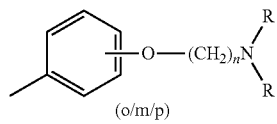

(o/m/p)
n = 2-6
R = alkyl or cycloalkyl ($C_4$-$C_8$)

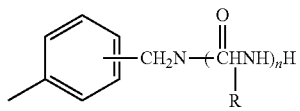

(o/m/p)
amide bond L or D
n = 1-4
R = alkyl or cycloalkyl ($C_4$-$C_8$)

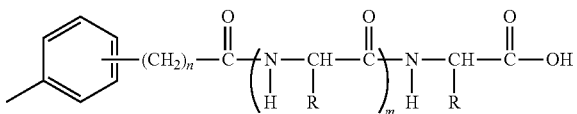

(o/m/p)
amide bond L or D
n = 0-2
m = 0-3
R = alkyl or cycloalkyl ($C_4$-$C_8$)

The above exemplary structures can be substituted at the indicated positions with substituents as described above. Any aryl and heteroaryl groups can also be substituted with one to five substituent groups, preferably one to three substituent groups. These substituent groups may include, independently, a detectable marker, H, $CH_3$, OH, $OCH_3$, $OCF_3$, $N(CH_3)_2$, $NHCOCH_3$, aryl, $CO_2CH_3$, $CONH_2$, $C_1$-$C_4$ alkyl, $(CF_2)_nF$ wherein n=1-4, Cl, Br, I, F, $O(CH_2)_nH$ wherein n=1-4, $NO_2$, $NH_2$, $NHCOR^4$, $CO_2H$, $CO_2R^4$, $CONHR^4$, amyl, thioether, $SR^6$, $S(O)R^6$, $SO_2R^6$, $SO_2NR^6R^7$, and $CH_3$, OH, $OCH_3$, $OCF_3$, $N(CH_3)_2$, $NHCOCH_3$, aryl, $CO_2CH_3$, $CONH_2$, $C_1$-$C_4$ alkyl, $(CF_2)_nF$ wherein n=1-4, Cl, Br, I, F, $O(CH_2)_nH$ wherein n=1-4, $NO_2$, $NH_2$, $NHCOR^4$, $CO_2H$, $CO_2R^4$, $CONHR^4$, amyl, thioether, $SR^6$, $S(O)R^6$, $SO_2R^6$, $SO_2NR^6R^7$ can optionally and independently each comprise (e.g., as an alternative or additional substituent) at least one detectable marker; wherein $R^4$ has the definition given above; wherein $R^6$ is H, $C_1$-$C_4$ alkyl or perfluoroalkyl, aryl, heteroaryl, or optionally substituted allyl, arylmethyl, alkynyl, alkenyl, wherein each of $C_1$-$C_4$ alkyl, perfluoroalkyl, aryl, heteroaryl, allyl, arylmethyl, alkynyl or alkenyl can optionally and independently comprise (e.g., as an alternative or additional substituent) at least one detectable marker; wherein $R^7$ is H, $C_1$-$C_4$ alkyl or perfluoroalkyl, aryl, heteroaryl, optionally substituted allyl, arylmethyl, $OR^8$ or $NHR^8$, and wherein each of $C_1$-$C_4$ alkyl, perfluoroalkyl, aryl, heteroaryl, allyl, arylmethyl, $OR^8$ or $NHR^8$ can optionally and independently comprise (e.g., as an alternative or additional substituent) at least one detectable marker; wherein $R^8$ is H, $C_1$-$C_6$ alkyl or perfluoroalkyl, aryl, heteroaryl, optionally substituted allyl or arylmethyl, $SO_2R^6$ or $S(O)R^6$, and $C_1$-$C_6$ alkyl, perfluoroalkyl, aryl, heteroaryl, allyl, arylmethyl, $SO_2R^6$ or $S(O)R^6$ can each optionally and independently comprise (e.g., as an alternative or additional substituent) at least one detectable marker, and further wherein $R^6$ has the definition given above; and $R^5$ can be in either the E or Z configuration.

Any aryl and heteroaryl groups with any combinations thereof for the compounds of the present invention can be substituted as elsewhere described, with one to five substituent groups. In a preferred aspect, any aryl and heteroaryl groups with any combinations thereof can be substituted as elsewhere described with one to three substituent groups, where the preferred substituent positions are indicated elsewhere herein.

These compounds are capable of effectively binding to the estrogen or the androgen receptor as well as estrogen-like or androgen-like receptors, accordingly, to inhibit or modulate the actions of estrogens or androgens as well as androgen-like or estrogen-like molecules.

In another aspect, the present invention is directed to a composition for prophylaxis or treatment of a hormone-responsive disorder containing the compounds of the invention. Preferably, the composition comprises a pharmaceutically acceptable carrier. For example, the composition can also be incorporated or contained in a pharmaceutically acceptable carrier substance, which can be inert, that is formulated for, without limitation, oral, topical, intravenous, intramuscular, subcutaneous, intra-vaginal, suppository, sublingual, intracisternal, intraperitoneal, parenteral or local administration via powders, ointments or drops, as well as for buccal or nasal spray administration. For detection and/or imaging type applications, a probe of the invention can comprise a pharmaceutically acceptable carrier substance, which can be inert, that is formulated for, without limitation, oral, topical, intravenous, intramuscular, subcutaneous, intra-vaginal, suppository, sublingual, intracisternal, intraperitoneal, parenteral or local administration via powders, ointments or drops, as well as for buccal or nasal spray administration. Compounds and probes thereof of the invention can also be used or administered in combination with radiation and/or surgery and/or other conventional drugs such as, for example, any antineoplastic or chemotherapeutic agents including, but not limited to, Lupron (leuprolide acetate), Zoladex (goserelin acetate implant), aromatase inhibitors (such as, for example, Arimidex®, Aromasin, Femara), herceptin, doxorubicin, and paclitaxol. Preferably, for detection and/or imaging type applications, administration of a probe of the invention comprising a detectable marker occurs via intravenous administration. Similarly, in one aspect, therapeutic applications of a compound of the invention can include oral administration to a patient.

Pharmaceutically acceptable carriers can include, for example, aqueous solutions, water, non-toxic excipients, including salts, preservatives, buffers, emulsions, liposomes, targeted liposomes, micelles, targeted micelles, nanoparticles and the like, as described, for instance, in REMINGTON'S PHARMACEUTICAL SCIENCES, 15th Ed. Easton: Mack Publishing Co. pp. 1405-1412 and 1461-1487 (1975) and THE NATIONAL FORMULARY XIV., 14th Ed. Washington: American Pharmaceutical Association (1975). The invention also contemplates salts, pharmaceutical compositions, derivatives, prodrugs, solvates, racemic mixtures or tautomeric forms of the compounds or probes of the invention.

In another aspect, the present invention is directed to a method of treating a patient suffering from or believed to be at risk of suffering from a hormone-responsive disorder by administering to the patient an effective amount of any of the compositions or compounds described herein for prophylaxis or treatment of hormone-responsive disorders.

In a further aspect, the compounds or probes of the invention can be administered to a subject as a composition in a dosage of about 0.1 μg/kg (body weight) per day to 10 μg/kg/day, preferably 0.5 μg/kg/day to 5 μg/kg/day, and preferably 1 μg to 100 μg for local administration. An exemplary preferred high dosage amount may be in the range of about 0.10 mg/kg/day to about 40 mg/kg/day, more preferably of about 0.50 mg/kg/day to about 20 mg/kg/day, and more preferably of about 1.0 mg/kg/day to about 10 mg/kg/day. Optimal dosage and modes of administration can readily be determined by those of ordinary skill in the art and conventional protocols. The amount of administration is also dependent on the disease-state, on the patient being treated, the patient's body weight and the type of administration.

In a further aspect, the present invention is directed to a kit comprising a composition of the invention and instructions for use thereof. For example, said instructions can be for therapeutic and/or detection or imaging type applications.

In a particular aspect, the present invention is directed to a method for the prophylaxis or treatment of prostate disorders in a patient by administering a compound of the invention (e.g., an antiandrogenic compound) in an effective amount. While not being bound by any theory, it is believed that in particular, an antiandrogenic compound of the invention can change the structural conformation in the helix-12 of the androgen receptor to inhibit transcriptional response.

In another aspect, the present invention is directed to an article of manufacture comprising a packaging material and a composition of the present invention contained within the packaging material. The composition can be (a) therapeutically effective for the prophylaxis or treatment of hormone-responsive disorders and/or (b) useful for detection or imaging type applications. The packing material also comprises a label with instructions for use, which indicates that the composition can be used for prophylaxis or treatment of hormone-responsive disorders and/or detection or quantitation of a disease state via, for example, in vivo imaging.

In another aspect, an address and message unit of a compound or probe thereof of the invention have the structure

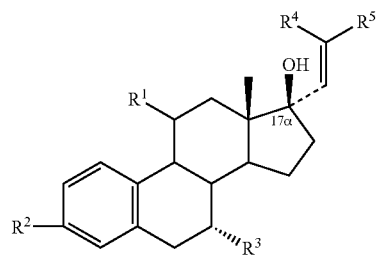

wherein $R^1$ (11 beta) and/or $R^3$ (7 alpha) can be essentially degenerate (pseudo degenerate). Moreover, with, for example, slightly different chemistry, essentially the same substituent can be introduced at both positions $R^1$ and $R^3$. $R^1$ and $R^3$ can also be any of the following, either alone or in combination:

—H, —OH, —OCH$_3$, -alkyl with 7 to 10 carbons (linear, branched, cycloalkyl) with 1 or more carbons replaced singly, multiply or in combination with up to n−1 carbons of N, S, and O and with hydrogen replaced singly or multiply up to replacement of all hydrogen with fluorine, or -alkenyl with 4 to 10 carbons (linear, branched, cycloalkenyl) with 1 or more carbons replaced singly, multiply or in combination with up to n−1 carbons of N, S, and O and with hydrogen replaced singly or multiply up to replacement of all hydrogen with fluorine;

aralkyl, where alkyl is 0, 2 to 10 carbons (linear, branched, cycloalkyl) with 1 or more carbons replaced singly, multiply or a combination of N, S, and O and with hydrogen replaced singly or multiply up to replacement of all hydrogen with fluorine;

aralkenyl, where alkene is 2 to 10 carbons (linear, branched, cycloalkyl) and the alkyl portion of the alkene being 0 to 8 carbons with 1 or more carbons of the alkyl portion replaced singly, multiply or a combination of N, S, and O and with hydrogen replaced singly or multiply up to replacement of all hydrogen with fluorine and configuration is cis or trans; or aralkynyl, where alkynyl is 2 to 10 carbons (linear, branched, cycloalkyl) and the alkyl portion of the alkyne being 0 to 8 carbons with 1 or more carbons of the alkyl portion replaced singly, multiply or a combination of N, S, and O and with hydrogen replaced singly or multiply up to replacement of all hydrogen with fluorine. In addition, $R^1$ and/or $R^3$ can optionally and independently comprise at least one detectable marker. For example, $R^1$ and/or $R^3$ can independently be any of the substituents (groups or moieties) above except for H and another detectable marker, which can each optionally and independently comprise one or more detectable markers including, for example, radionuclides, isotopes, radioisotopes, Re, Tc, indium, La, terbium, yttrium, Cu or gallium.

Furthermore, $R^2$ can be any of the following, either alone or in combination: hydroxyl, carboxyaryl, carboxyalkyl, alkoxy or OR$^P$, wherein $R^P$ is H, CH$_3$, COCH$_3$, CO(CH$_2$)$_n$CH$_3$, CO-aryl, alkyl, cycloalkyl (ether), ester, —COCH$_3$, a detectable marker, and any of these substituents for $R^2$ (except for H and another detectable marker) can also optionally and independently comprise at least one detectable marker.

In one aspect, $R^4$ and $R^5$ represent groups that can be equivalent or different using, for example, slightly different chemistry. For example, any substitution at $R^4$ or $R^5$ can be mono or di-substituted and equivalent or non-equivalent. Preferably, if $R^4$ is hydrogen or alkyl then $R^5$ can be a detectable marker, alkyl, aryl, or substituted aryl, heteroaryl, alkyl alcohol where alkyl is 1 to 10 carbons (linear, branched, cycloalkyl) and where hydroxyl group(s) is on any carbon(s) in the alkyl portion, alkyl carbonyl or where alkyl is 1 to 10 carbons (linear, branched, cycloalkyl) and where carbonyl group(s) is on any carbon(s) in the alkyl portion, or fused aromatics (any of these substituents, except for hydrogen or another detectable marker, can also optionally and independently comprise one or more detectable markers). Similarly, for example, if $R^5$ is hydrogen or alkyl then $R^4$ can be a detectable marker, alkyl where $R^5$ is not hydrogen, aryl, or substituted aryl; heteroaryl, alkyl alcohol and where hydroxyl group(s) is on any carbon(s) in the alkyl portion; alkyl carbonyl and further where carbonyl group(s) is on any carbon(s) in the alkyl portion; or fused aromatics (any of these substituents, except for hydrogen or another detectable marker, can also optionally and independently comprise one or more detectable markers). Moreover, $R^4$ or $R^5$ can be in either the E or Z configuration in relation to the 17α-position of the address unit.

Moreover, $R^4$ and $R^5$ groups can be any suitable detectable marker, or substituents as disclosed herein that optionally can include a detectable marker. For example, a detectable marker can include radionuclides, isotopes or radioisotopes. Exemplary detectable markers can also be isotopic or radioisotopic halogens. Similarly, as indicated, any detectable marker can be a substituent to any of the groups disclosed herein as exemplary substituents of $R^4$ and/or $R^5$ including, for example, aryl, heteroaryl, fused aryl, —CO-aryl, CO-fused aryl, —CO-heteroaryl, —CO-fused heteroaryl, biaryl, CO-biaryl, ether-linked aryls, ether-linked heteroaryls, amine-linked aryls, amine-linked heteroaryls, aminoalkoxy arene hybrid or peptidyl hybrid. Any substituents (except for H or another detectable marker) for $R^4$ and/or $R^5$ can also each be optionally substituted, independently, for example, with at least one detectable marker, H, $CH_3$, OH, $OCH_3$, $OCF_3$, $N(CH_3)_2$, $NHCOCH_3$, aryl, $CO_2CH_3$, $CONH_2$, $C_1$-$C_4$ alkyl, $(CF_2)_nF$ wherein n=1-4, Cl, Br, I, F, $O(CH_2)_nH$ wherein n=1-4, $NO_2$, $NH_2$, $NHCOR^4$, $CO_2H$, $CO_2R^4$, $CONHR^4$, amyl, thioether, $SR^6$, $S(O)R^6$, $SO_2R^6$, $SO_2NR^6R^7$, and $CH_3$, OH, $OCH_3$, $OCF_3$, $N(CH_3)_2$, $NHCOCH_3$, aryl, $CO_2CH_3$, $CONH_2$, $C_1$-$C_4$ alkyl, $(CF_2)_nF$ wherein n=1-4, Cl, Br, I, F, $O(CH_2)_nH$ wherein n=1-4, $NO_2$, $NH_2$, $NHCOR^4$, $CO_2H$, $CO_2R^4$, $CONHR^4$, amyl, thioether, $SR^6$, $S(O)R^6$, $SO_2R^6$, $SO_2NR^6R^7$ can optionally and independently each comprise (e.g., as an alternative or additional substituent) at least one detectable marker; wherein $R^4$ has the definition given above; wherein $R^6$ is H, $C_1$-$C_4$ alkyl or perfluoroalkyl, aryl, heteroaryl, or optionally substituted allyl, arylmethyl, alkynyl, alkenyl, wherein each of $C_1$-$C_4$ alkyl, perfluoroalkyl, aryl, heteroaryl, allyl, arylmethyl, alkynyl or alkenyl can optionally and independently comprise (e.g., as an alternative or additional substituent) at least one detectable marker; wherein $R^7$ is a detectable marker, H, $C_1$-$C_4$ alkyl, perfluoroalkyl, aryl, heteroaryl, optionally substituted allyl, arylmethyl, $OR^8$ or $NHR^8$, and wherein each of $C_1$-$C_4$ alkyl, perfluoroalkyl, aryl, heteroaryl, allyl, arylmethyl, $OR^8$ or $NHR^8$ can optionally and independently comprise (e.g., as an alternative or additional substituent) at least one detectable marker; and further wherein $R^8$ is a detectable marker, H, $C_1$-$C_6$ alkyl or perfluoroalkyl, aryl, heteroaryl, optionally substituted allyl or arylmethyl, $SO_2R^6$ or $S(O)R^6$, and $C_1$-$C_6$ alkyl, perfluoroalkyl, aryl, heteroaryl, allyl, arylmethyl, $SO_2R^6$ or $S(O)R^6$ can each optionally and independently comprise (e.g., as an alternative or additional substituent) at least one detectable marker, wherein $R^6$ has the definition given above.

Moreover, such exemplary substituents as, for example, $CH_3$, OH, $OCH_3$, $OCF_3$, $N(CH_3)_2$, $NHCOCH_3$, aryl, $CO_2CH_3$, $CONH_2$, $C_1$-$C_4$ alkyl, $(CF_2)_nF$ wherein n=1-4, Cl, Br, I, F, $O(CH_2)_nH$ wherein n=1-4, $NO_2$, $NH_2$, $NHCOR^4$, $CO_2H$, $CO_2R^4$, $CONHR^4$, amyl, thioether, $SR^6$, $S(O)R^6$, $SO_2R^6$, $SO_2NR^6R^7$; wherein $R^4$ has the definition given above; wherein $R^6$ is H, $C_1$-$C_4$ alkyl or perfluoroalkyl, aryl, heteroaryl, or optionally substituted allyl, arylmethyl, alkynyl, alkenyl; wherein $R^7$ is H, $C_1$-$C_4$ alkyl or perfluoroalkyl, aryl, heteroaryl, optionally substituted allyl, arylmethyl, $OR^8$ or $NHR^8$; wherein $R^8$ is H, $C_1$-$C_6$ alkyl or perfluoroalkyl, aryl, heteroaryl, optionally substituted allyl or arylmethyl, $SO_2R^6$ or $S(O)R^6$, wherein $R^6$ has the definition given above, can each optionally and independently comprise at least one detectable marker as a substituent thereto or replacement for, without limitation, a hydrogen, halogen, nitrogen, carbon, sulfur, or oxygen.

In one aspect, agents such as gold nanoparticles or nanorods, rhenium tricarbonyl or iron nanoparticles and gadolinium complexes can be used as or comprise at least one detectable marker substituents to any position of a compound or probe thereof of the invention. A marker substituent can also be an optional substituent to any of the groups disclosed herein as exemplary groups such as, for example, aryl, heteroaryl, fused aryl, —CO-aryl, CO-fused aryl, —CO-heteroaryl, —CO-fused heteroaryl, biaryl, CO-biaryl, ether-linked aryls, ether-linked heteroaryls, amine-linked aryls, amine-linked heteroaryls, aminoalkoxy arene hybrid, detectable marker, peptidyl hybrid. Gold nanorods, rhenium tricarbonyl and iron or gadolinium nanoparticles can be used therapeutically or for detection or imaging type applications including, without limitation, near infrared luminescence, receptor mapping and/or MRI.

In one aspect, the invention relates to a method for detecting hormone receptors in a subject. For example, the method can comprise administering an effective amount of a compound or probe of the invention to a subject and detecting the binding of the compound or probe (or analogs, salts, pharmaceutical compositions, derivatives, prodrugs or racemic mixtures thereof) to at least one receptor in the subject. Preferably, the receptor is a receptor of interest such as, for example, a hormone receptor. Exemplary receptors of interest can include, but not limited to, those found in tissues as well as estrogen receptors and/or androgen receptors as well as estrogen-like and/or androgen-like receptors. Binding (association or interaction) of a compound or probe of the invention with and/or to tissues or receptors of interest, including receptors from tissues comprising proteins, precursors, portions, fragments and peptides of the receptors of interest, can be of high-affinity and a specific or preferential nature as would be understood by one of ordinary skill in the art and evaluated by conventional techniques related to binding (for example, dissociation constants).

Preferably, a compound or probe of the invention can bind to estrogen receptors and/or androgen receptors (and/or estrogen-like and/or androgen-like receptors). For example, a compound or probe of the invention can bind to tissue, which can comprise one or more receptors of interest. A compound or probe of the invention can preferentially bind to hormone receptors that are present with disease states or maladies characterized by or associated with a hormone-responsive disorder.

A compound or probe of the invention can bind to one or more tissues or receptors of interest, for example, hormone receptors with a dissociation constant (for example, an equilibrium dissociation constant, $K_d$) from, for example, about 0.0001 to 10 μM (or from 0.0001 to 7 μM, 0.0001 to 5 μM, 0.0001 to 1 μM, 0.001 to 5 μM, 0.01 to 5 μM and/or 0.1 to 5 μM) as measured by any suitable techniques routine to those of ordinary skill in the art. The invention contemplates measurement of a dissociation constant (for example, $K_d$ and $K_i$) or performing competition, saturation and kinetics experiments by conventional techniques routine to one of ordinary skill in the art. Moreover, a compound or probe of the invention can compete with a reference compound for binding to and/or with tissues or receptors of interest with a dissociation constant of inhibition (for example, $K_i$) from, for example, about 0.01 nM to >10,000 nM (or from 0.001 to 7,000 nM, 0.001 to 5,000 nM, 0.001 to 1,000 nM, 0.01 to 5,000 nM, 0.01 to 2,000 nM and/or 0.1 to 5,000 nM).

The invention also contemplates the use of conjugates as substituents to the compounds or probes of the invention. A conjugate can be a substituent to any position of the address or message unit. In one aspect, a conjugate can be a substituent to $R^1$ of

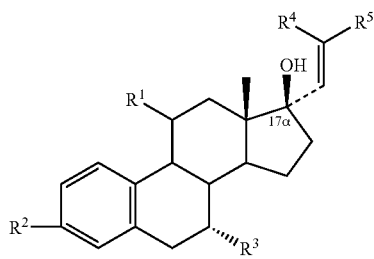

A conjugate to a compound or probe of the invention can also be a substituent to any suitable groups (for example, those not comprising only H or a detectable marker) disclosed herein as exemplary substituents such as, for example, aryl, heteroaryl, fused aryl, —CO-aryl, CO-fused aryl, —CO-heteroaryl, —CO-fused heteroaryl, biaryl, CO-biaryl, ether-linked aryls, ether-linked heteroaryls, amine-linked aryls, amine-linked heteroaryls, aminoalkoxy arene hybrid, or peptidyl hybrid. Any suitable substituents (for example, those not comprising only H or a detectable marker) can also optionally and independently comprise one or more detectable markers, H, $CH_3$, OH, $OCH_3$, $OCF_3$, $N(CH_3)_2$, $NHCOCH_3$, aryl, $CO_2CH_3$, $CONH_2$, $C_1$-$C_4$ alkyl, $(CF_2)_n F$ wherein n=1-4, Cl, Br, I, F, $O(CH_2)_n H$ wherein n=1-4, $NO_2$, $NH_2$, $NHCOR^4$, $CO_2H$, $CO_2R^4$, $CONHR^4$, amyl, thioether, $SR^6$, $S(O)R^6$, $SO_2R^6$, $SO_2NR^6R^7$; wherein $R^4$ has the definition given above; wherein $R^6$ is H, $C_1$-$C_4$ alkyl or perfluoroalkyl, aryl, heteroaryl, or optionally substituted allyl, arylmethyl, alkynyl, alkenyl; wherein $R^7$ is H, $C_1$-$C_4$ alkyl or perfluoroalkyl, aryl, heteroaryl, optionally substituted allyl, arylmethyl, $OR^8$ or $NHR^8$; wherein $R^8$ is H, $C_1$-$C_6$ alkyl or perfluoroalkyl, aryl, heteroaryl, optionally substituted allyl or arylmethyl, $SO_2R^6$ or $S(O)R^6$, wherein $R^6$ has the definition given above, and these exemplary substituents can be linked to or comprise a conjugate as disclosed herein.

Conjugates for use with a compound or probe of the invention can also serve as linkers to, for example, any suitable substituents or groups, detectable markers, halogens, proteins, enzymes, polypeptides, drugs, dyes, nucleosides, oligonucleotides, lipids, phospholipids and/or liposomes. Exemplary conjugates can include polyethylene amine (PEI), polyglycine, hybrids of PEI and polyglycine, polyethylene glycol (PEG) or methoxypolyethylene glycol (mPEG). In one aspect, such a conjugate can link a compound of the invention to, without limitation, a detectable marker (such as, for example, a radionuclide, isotope, radioisotope and/or therapeutic label) to comprise a probe of the invention. A conjugate for use with a compound or probe of the invention can, in one application, improve the in vivo half-life of both. Other exemplary applications and conjugates for use with a compound or probe of the invention include those generally disclosed in U.S. Pat. No. 5,672,662, which is hereby incorporated by reference herein. In one aspect, a conjugate of a compound of the invention provides a linkage to a detectable maker to comprise a probe thereof. For example, an exemplary conjugate of PEG can be used to "pegylate" or link a compound of the invention to an isotopic or radioisotopic halogen to yield a probe for detection and/or imaging type applications.

In one aspect, $R^1$ of

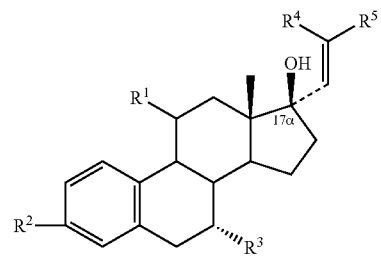

can be substituted with an exemplary conjugate such as that generally disclosed in U.S. Pat. No. 5,672,662. Such a conjugate can be used to link a compound of the invention to any suitable detectable marker.

In another aspect, an address and message unit of a compound or probe of the invention have the structure

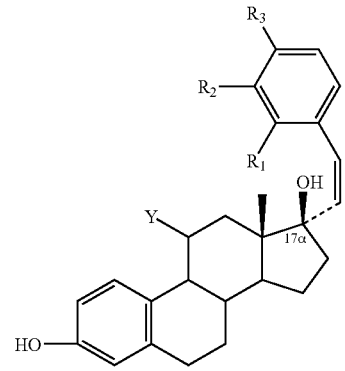

wherein exemplary substituents for Y, $R_1$, $R_2$ and $R_3$ above as well as E/Z conformations thereof are provided in Table 1a below. The above compound or probe, by way of example, can also comprise one or more substituents (e.g., additional or alternative) as a detectable marker (label, marker or tag). Preferably, the compound or probe can comprise one or more substituents, which can each independently comprise $^{131}I$, $^{124}I$, $^{125}I$, $^{3}H$, $^{123}I$, $^{18}F$, $^{19}F$, $^{11}C$, $^{75}Br$, $^{13}C$, $^{13}N$, $^{15}O$, $^{76}Br$, $CH_2$—$CH_2$-label O—$CH_2$—$CH_2$-label, $CH_2$—$CH_2$—$CH_2$-label, O—$CH_2$—$CH_2$—$CH_2$-label, —[$OCH_2$—$CH_2$]$_n$-label, O—$CH_2$—CH=CH-label, N—$CH_2$—CH=CH-label in which "label" can independently be $^{131}I$, $^{124}I$, $^{125}I$, $^{3}H$, $^{123}I$, $^{18}F$, $^{19}F$, $^{11}C$, $^{75}Br$, $^{13}C$, $^{13}N$, $^{15}O$, $^{76}Br$, $^{11}C$ or $^{13}C$ can be a label (mark or tag) as a substituent of a lower alkyl group, $(CH_2)_n OR$, $CL_3$, $CH_2$—$CH_2$-L, O—$CH_2$—$CH_2$-L, $CH_2$—$CH_2$—$CH_2$-L, O—$CH_2$—$CH_2$—$CH_2$-L, CN, (C=O)—R, (C=O)N(R)$_2$, O(CO)R, OR, COOR, aryl, CR=CR-aryl or $CR_2$—$CR_2$-aryl in which L can be a halogen (for example, $^{13}CH_2$—$CH_2$—F) and R can be H, F, Cl, Br, I or a lower alkyl group.

Any compound of the invention can also be administered to a subject, such as, for example, a human, for the inhibition of cell proliferation as well as the prophylaxis and/or treatment of its related diseases. Examples of such diseases can include androgen or estrogen mediated disorders or disease states. An androgen or estrogen disorder can, for example, include osteoporosis, endometriosis, breast cancer, benign breast cancer, uterine cancer, ovarian cancer, polycystic ovarian disease, prostate cancer, benign prostatic hyperplasia, cardiac diseases, coronary artery disease, acne, seborrhea, alopecia, hirsutism, male pattern baldness, or infertility.

For example, a compound of the invention can be used for a method of treating a patient believed to be at risk of suffering from an estrogen or androgen mediated disorder. Such a method can comprise the steps of providing said patient and administering to the patient an effective amount of the compound, wherein said amount of the compound is effective in treating said estrogen or androgen mediated disorder. The compound can also be administered to a patient as a therapeutic composition. Exemplary compositions of the invention can comprise a compound or probe of the invention and any type of pharmaceutically acceptable carrier thereof.

TABLE 1a

| Y Substituents | $R_1$ Substituents | $R_2$ Substituents | $R_3$ Substituents | E/Z Conformation |
|---|---|---|---|---|
| H | $NO_2$ | H | H | E |
| H | H | $CH_3$ | H | E |
| H | H | H | F | E |
| H | H | H | $NH_3$ | Z |
| H | H | H | $CF_3$ | E |
| H | H | $CF_3$ | H | E |
| H | $CF_3$ | H | H | E |
| H | $CH_2F$ | H | H | E |

In one aspect, substituents Y, $R_1$, $R_2$ and $R_3$ in Table 1a can comprise H, $CH_2F$, H and H, respectively. The invention also contemplates that $R_1$, $R_2$ and $R_3$ in Table 1a can optionally and independently each comprise, by way of example, one or more substituents (e.g., additional or alternative) as a detectable marker (label, marker or tag). For example, one or more substituents for $R_1$, $R_2$ and $R_3$ can each independently comprise $^{131}I$, $^{124}I$, $^{125}I$, $^3H$, $^{123}I$, $^{18}F$, $^{19}F$, $^{11}C$, $^{75}Br$, $^{13}C$, $^{13}N$, $^{15}O$, $^{76}Br$, $CH_2$—$CH_2$-label, O—$CH_2$—$CH_2$-label, $CH_2$—$CH_2$—$CH_2$-label, O—$CH_2$—$CH_2$—$CH_2$-label, —[$OCH_2$—$CH_2$]$_n$- label, O—$CH_2$—CH=CH-label, N—$CH_2$—CH=CH-label in which "label" can independently be $^{131}I$, $^{124}I$, $^{125}I$, $^3H$, $^{123}I$, $^{18}F$, $^{19}F$, $^{11}C$, $^{75}Br$, $^{13}C$, $^{13}N$, $^{15}O$, $^{76}Br$, $^{11}C$ or $^{13}C$ can be a label (mark or tag) as a substituent of a lower alkyl group, $(CH_2)_n OR$, $CL_3$, $CH_2$—$CH_2$-L, O—$CH_2$—$CH_2$-L, $CH_2$—$CH_2$—$CH_2$-L, O—$CH_2$—$CH_2$—$CH_2$-L, CN, (C=O)—R, (C=O)N(R)$_2$, O(CO)R, OR, COOR, aryl, CR=CR-aryl or $CR_2$—$CR_2$-aryl in which L can be a halogen (for example, $^{13}CH_2$—$CH_2$—F) and R can be H, F, Cl, Br, I or a lower alkyl group. For example, $CH_2F$ for $R_1$ can, without limitation, comprise an $^{18}F$ or $^{19}F$ substituent as a detectable marker. Exemplary detectable markers can be used to, for example, study receptor distributions via radioscintigraphy, magnetic resonance imaging (MRI), chemilumensence, near infrared luminescence, fluorescence, SPECT, computed tomography (CT scan), positron emission tomography (PET) or combinations thereof. The invention also contemplates the use of any conventional imaging means, devices or systems for carrying out radioscintigraphy, magnetic resonance imaging (MRI), chemilumensence, near infrared luminescence, fluorescence, SPECT, computed tomography (CT scan), positron emission tomography (PET) or combinations thereof. Exemplary imaging means, devices or systems include those generally disclosed in U.S. Pat. Nos. 6,072,177, 6,803,580, 5,900,636, 6,271,524, 5,532,489, 5,272,343, 5,241,181, 5,512,755, 5,345,082, 5,023,895, 4,864,140, 5,323,006, 4,675,526 and 4,395,635, each of which are incorporated by reference herein.

In one aspect, the probes of the invention can be used in conjunction with non-invasive imaging techniques such as, for example, magnetic resonance spectroscopy (MRS) or imaging (MRI), positron emission tomography (PET), and single-photon emission computed tomography (SPECT). For example, a compound of the invention can be labeled with a detectable marker such as $^{19}F$ or $^{13}C$ for MRS/MRI by general organic chemistry techniques known to the art, yielding a probe of the invention. See, e.g., March, J. ADVANCED ORGANIC CHEMISTRY: I REACTIONS, MECHANISMS, AND STRUCTURE (3rd Edition, 1985).

For example, a compound of the invention can be radiolabeled with $^{18}F$, $^{18}C$, $^{18}Br$, or $^{18}Br$, to provide for a probe for PET, by techniques well known in the art and described by Fowler, J. and Wolf, A. in POSITRON EMISSION TOMOGRAPHY AND AUTORADIOGRAPHY (Phelps, M., Mazziota, J., and Schelbert, H. eds.) 391-450 (Raven Press, NY 1986). The compounds of the invention also may be radiolabeled with $^{123}I$, to provide a probe for SPECT, by any of several techniques known to the art. See, e.g. Kulkarni, Int. J. Rad. Appl. & Inst. (Part B) 18: 647 (1991); Mankoff, David A. et al., [$^{18}F$] Fluoroestradiol radiation dosimetry in human PET studies, Journal of Nuclear Medicine (2001), 42(4), 679-684; Mortimer, Joanne E. et al., Positron emission tomography with 2-[$^{18}F$]fluoro-2-deoxy-D-glucose and 16α-[$^{18}F$] fluoro-17β-estradiol in breast cancer: Correlation with estrogen receptor status and response to systemic therapy, Clinical Cancer Research (1996), 2(6), 933-939; and Mintun et al., Breast cancer: PET imaging of estrogen receptors, Radiology (1988), 169(1), 45-8.

In addition, a probe of the invention can comprise any suitable detectable marker such as a radioactive iodine isotope including, but not limited to, $^{131}I$, $^{125}I$, or $^{123}I$. Typically, labeling of a compound of the invention to yield a probe thereof can be performed by conventional techniques as will be appreciated by those of ordinary skill in the art. A probe of the invention may also comprise a metal radiolabel such as, for example, Technetium-99m ($^{99m}Tc$). Modification of substituents of a compound of the invention to introduce ligands that bind such metal ions can be effected without undue experimentation by one of ordinary skill in the radiolabeling art. Preparing radiolabeled derivatives of $^{99m}Tc$ is well known in the art. See, for example, Zhuang et al., "Neutral and stereospecific Tc-99m complexes: [$^{99m}Tc$]N-benzyl-3,4-di-(N-2-mercaptoethyl)-amino-pyrrolidines (P-BAT)" Nuclear Medicine & Biology 26(2):217-24, (1999); Oya et al., "Small and neutral Tc(v) O BAT, bisaminoethanethiol (N2S2) complexes for developing new brain imaging agents" Nuclear Medicine & Biology 25(2):135-40, (1998); and Hom et al., "Technetium 99m-labeled receptor-specific small-molecule radiopharmaceuticals: recent developments and encouraging results" Nuclear Medicine & Biology 24(6):485-98, (1997).

The probes of the invention may also use detectable markers that are isotopes detectable by nuclear magnetic resonance spectroscopy for purposes of in vivo imaging and spectroscopy. Substituents particularly useful in magnetic resonance spectroscopy include $^3F$ and $^{13}C$. Suitable radioisotopes for a probe of the invention include beta-emitters, gamma-emitters, positron-emitters, and x-ray emitters. These radioisotopes include, for example, $^{131}I$, $^{123}I$, $^OF$, $^{11}C$, $^{75}Br$, $^{125}I$, $^{14}C$, $^3H$ and $^{76}Br$. Suitable stable isotopes for use in MRI and/or Spectroscopy (MRS) can include, for example, $^{19}$F and $^{13}$C. Preferably, $^{11}$C or $^{18}$F can be used for PET in vivo imaging, $^{123}$I can be used in SPECT imaging, $^{19}$F can be used in MRS/MRI, and $^{3}$H or $^{14}$C can be used for in vitro studies. Any conventional method for visualizing a probe can be utilized in accordance with the invention.

In one aspect, a detectable marker for a probe of the invention is a radiolabel, although other labels such as enzymes, chemiluminescent and immunofluorescent compounds are well known to skilled artisans. When the compounds of the invention are to be used as a probe, they must be labeled with a detectable marker such as, for example, suitable radioactive halogen isotopes. Although $^{125}$I-isotopes are useful for laboratory testing, they will generally not be useful for actual diagnostic purposes because of the relatively long half-life (60 days) and low gamma-emission (30-65 Kev) of $^{125}$I. The isotope $^{123}$I has a half life of thirteen hours and gamma energy of 159 KeV such that this isotope may be preferable for in vivo detection and/or imaging type applications using a probe of the invention.

The invention also provides for kits that can be used to prepare probes from the compounds of the invention. Kits for preparing a probe of the invention can contain, for example, a vial containing a physiologically suitable solution of an intermediate of a compound of the invention in a concentration and at a pH suitable for optimal complexing conditions. For example, the user would add to the vial an appropriate quantity of the radioisotope, e.g., Na$^{123}$I, and an oxidant, such as, without limitation, hydrogen peroxide. The resulting probe labeled with a detectable marker may then be administered, for example, intravenously to a patient and imaged by can mean of measuring the gamma ray or photo emissions therefrom.

In one aspect, the invention provides a kit comprising as materials therefor a non-radiolabeled compound of the invention. Optionally, the compound can be in a dry condition and, also optionally, one or more inert, pharmaceutically acceptable carriers and/or auxiliary substances may be added thereto. A kit of the invention can also include materials such as a reducing agent and, optionally, a chelator. These materials may also be combined. Moreover, the kit can comprise instructions for carrying out a method that involves reacting the materials with a detectable marker including, without limitation, $^{123}$I, $^{125}$I, $^{124}$I, $^{131}$I, $^{18}$F, $^{75}$Br, $^{76}$Br or $^{99m}$Tc. An exemplary $^{99m}$Tc detectable marker can be in the form of a pertechnetate solution that is, optionally, included with a kit of the invention. Similarly, the detectable marker can also be included with the kit. The kit can also include instructions for performing an in vivo imaging protocol with a probe prepared therefrom.

In one aspect, a pertechnetate solution for a kit of the invention can be obtained from a molybdenum-technetium-generator. Such generators are available in a number of institutions that perform radiodiagnostic procedures. As indicated, the materials for a kit of the invention may be combined, provided they are compatible. Such a monocomponent kit, in which the combined materials are preferably lyophilized, is suitable to be reacted by the user with the pertechnetate solution in a simple manner that will be appreciated by those of ordinary skill in the art. When desired, a kit of the invention may also include any additive such as, for example, pH controlling agents (e.g., acids, bases, buffers), stabilizers (e.g., ascorbic acid) or isotonizing agents (e.g., sodium chloride).

The present invention also provides for halogenated estradiol analogs to the compounds of the invention. Any of the family of halogen atoms may be used in conjunction with the compounds or probes of the invention. By way of example, the halogen atoms include fluorine, bromine, iodine, chlorine and astatine and detectable markers thereof. For example, radiolabeling of the compounds of the invention can be carried out using detectable markers such as $^{18}$F, $^{131}$I, $^{123}$I, $^{77}$Br or $^{11}$I for SPECT, or $^{75}$Br for PET. In one aspect, salts, pharmaceutical compositions, derivatives, prodrugs, solvates, racemic mixtures or tautomeric forms of the compounds of the invention can include a detectable marker, for example, $^{18}$F or $^{75}$Br (for positron) and $^{131}$I, $^{123}$I or $^{77}$Br atom (for SPECT), to comprise a probe of the invention. As indicated, a detectable marker can be located at any position of the address or message unit of a probe of the invention. Exemplary detectable markers can also include any of those generally disclosed in U.S. Pat. Nos. 5,192,525, 6,114,175, 6,274,119 and 6,096,874, each of which are incorporated by reference herein. The invention also contemplates methods, uses, devices and systems for imaging such as, for example, those generally disclosed in U.S. Pat. Nos. 5,192,525, 6,096, 874, 6,072,177, 6,803,580, 5,900,636, 6,271,524, 5,532,489, 5,272,343, 5,241,181, 5,512,755, 5,345,082, 5,023,895, 4,864,140, 5,323,006, 4,675,526 and 4,395,635, each of which are incorporated by reference herein.

One object of the present invention can be to provide an estrogen or androgen receptor (or estrogen-like and/or androgen-like receptor) imaging probe which has high affinity for the estrogen or androgen receptor (or estrogen-like and/or androgen-like receptor) and high enough specific activity such as, for example, >1 Ci/µmol, to be suitable for use in positron emission tomography. Another object of the invention can be to provide a probe which, as a result of the foregoing characteristics, has superior target tissue selectivity in vivo. Another object of the present invention can be to provide a method for monitoring the effectiveness of endocrine therapy in treating solid tumors, such as, for example, those of the breast or prostate. A further object of the present invention can be to achieve a substituted estradiol derivative which, as a compound or probe, has both high receptor binding affinity and/or high specific radioactivity.

Another object of the invention can be to provide a probe, useful in radioscintigraphy, magnetic resonance imaging (MRI), chemilumensence, near infrared luminescence, fluorescence, SPECT, computed tomography (CT scan), positron emission tomography (PET) or combinations thereof, which can have a high specific activity (e.g., radioactivity) and high target tissue selectivity by virtue of its high affinity for the estrogen or androgen receptor (or estrogen-like and/or androgen-like receptor). Such tissue selectivity can be capable of further enhancement by coupling this highly selective probe with targeting labels such as, for example, nano/microparticles.

The invention also provides a method for imaging receptor distributions in a sample or patient, the method comprising: (a) contacting a sample or administering to a patient, in an effective amount, a labeled compound or probe according to the invention (or salts, pharmaceutical compositions, derivatives, prodrugs, solvates, racemic mixtures or tautomeric forms of the compounds or probes of the invention); (b) detecting the spatial distribution and amount of the labeled compound or probe according to the invention bound to receptors of interest in the sample or patient using an imaging means to obtain an image; and (c) displaying an image of the spatial distribution and amount of the labeled compound or probe according to the invention bound to the receptors of interest. In another aspect of the invention, the imaging means is selected from, for example, radioscintigraphy, magnetic resonance imaging (MRI), chemilumensence, near infrared luminescence, fluorescence, SPECT, computed tomography (CT scan), positron emission tomography (PET) type devices or systems or combinations thereof.

The invention also provides for methods of imaging receptors in estrogen receptor and/or androgen receptor-rich tissues (and/or estrogen-like and/or androgen-like receptor rich tissues). The term "tissue" as used herein can mean any part of a patient's body (e.g., organs, tissues, cells). Examples of tissues can include brain, heart, liver, bone, breast and prostate tissues. In one aspect, a method of the invention comprises administering an effective amount of a compound or probe of the invention, which has been labeled with a detectable marker, to an estrogen receptor and/or androgen receptor (or estrogen-like and/or androgen-like receptor) rich tissue of a patient. The method also comprises suitably positioning the patient in an imaging means, device, system or portion thereof. In one aspect, the method also comprises performing a scan such as, for example, an emission scan of the estrogen receptor and/or androgen receptor (or estrogen-like and/or androgen-like receptor) rich tissue and obtaining an image such as, for example, a PET image of the tissue and evaluating the image for the presence or absence of focally increased uptake of the labeled compound or probe of the invention in the tissue. By way of example, a detectable marker of a labeled compound or probe of the invention can be $^{18}F$, $^{77}Br$, $^{75}Br$, $^{131}I$, $^{121}I$ or $^{11}CH_3I$. The method of the invention may be used to image hormone receptors in virtually any estrogen receptor and/or androgen receptor and/or estrogen-like and/or androgen-like receptors rich tissue. By way of example, such estrogen receptor and/or androgen receptor (or estrogen-like and/or androgen-like receptor) rich tissues include breast tissue, heart, bone, prostate or uterine tissue. Particular estrogen receptor and/or androgen receptor (or estrogen-like and/or androgen-like receptor) rich tissues with which the methods of the invention may be useful in imaging include, without limitation, breast, prostate or uterine tissue.

Any of the compounds of the invention can be used, without limitation, to inhibit cell proliferation in a subject and/or prophylaxis and/or treatment of its related diseases or disorders. The compounds of the invention can be used, for example, as agents that may block cancer cell proliferation. Moreover, the compounds of the invention can be administered to a subject in a composition to inhibit cell proliferation. Exemplary compositions of the invention can comprise a compound of the invention and a pharmaceutically acceptable carrier substance therefor.

In one aspect, the invention provides a method of inhibiting cell proliferation in a patient. For example, the method comprises the steps of providing said patient and administering to said patient an effective amount of a compound of the invention, wherein the amount of the compound is effective for inhibition of cell proliferation in said patient. In another aspect, the compound of the invention can be administered to the patient as a composition comprising a compound of the invention and a pharmaceutically acceptable carrier substance therefor.

BRIEF DESCRIPTION OF THE FIGURES

Other features and advantages of the invention may also be apparent from the following detailed description thereof, taken in conjunction with the accompanying drawings, which may depict preferred aspects by way of example, not by way of limitations.

Figure 2:
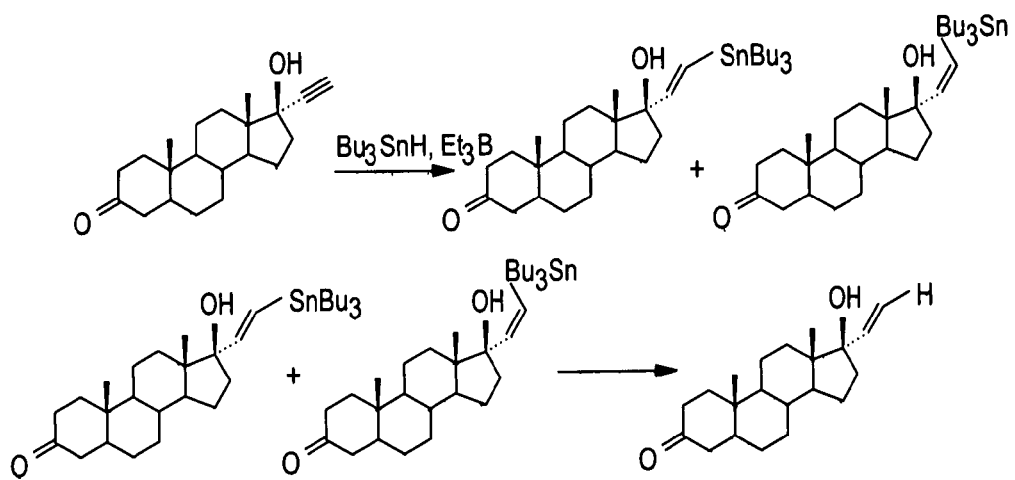
Figure 3:
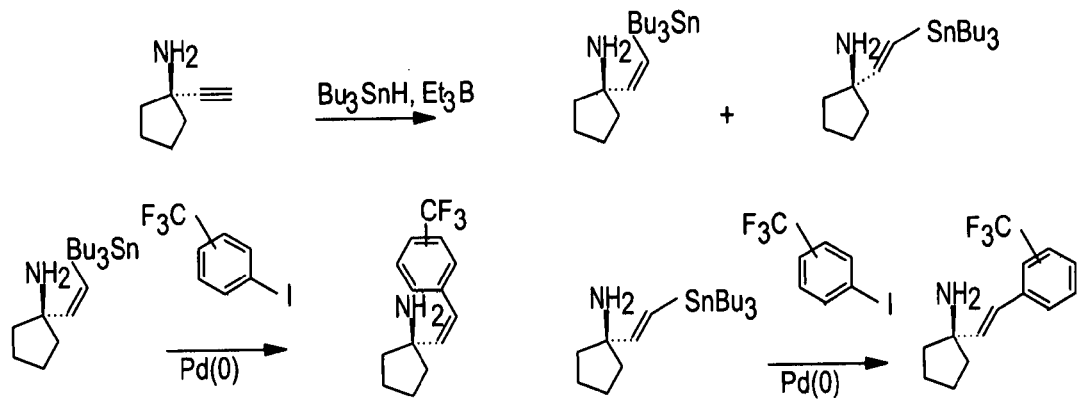
Figure 4:
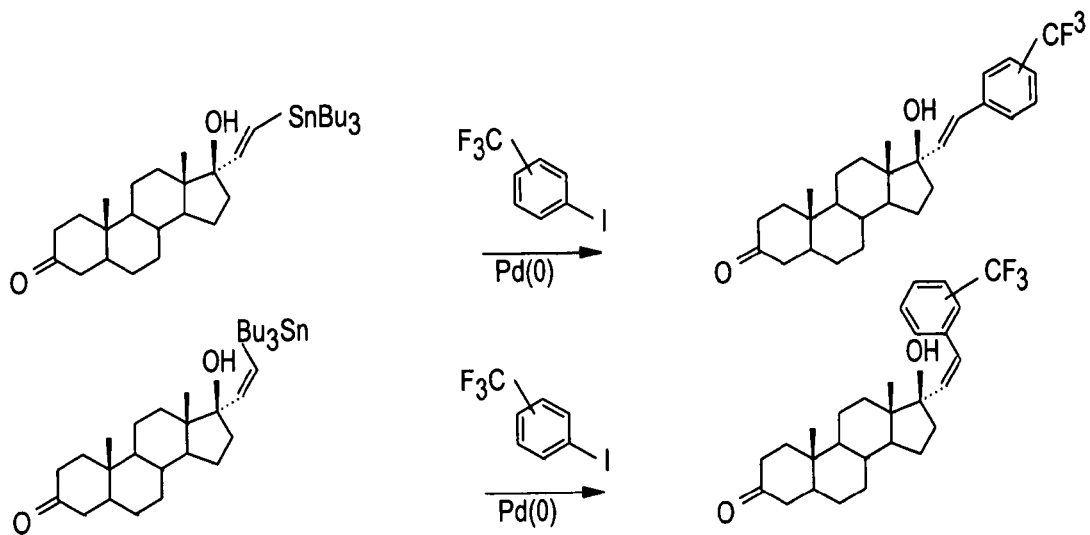
Figure 5:
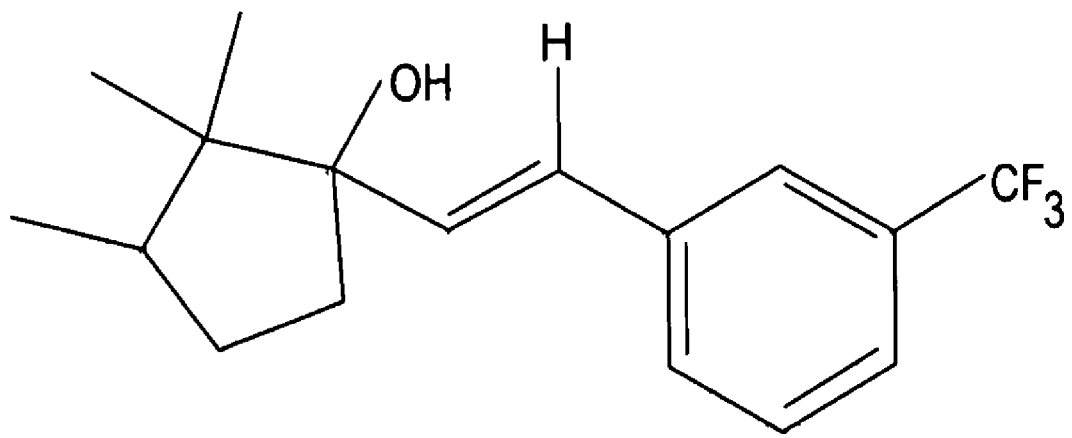
Figure 5:
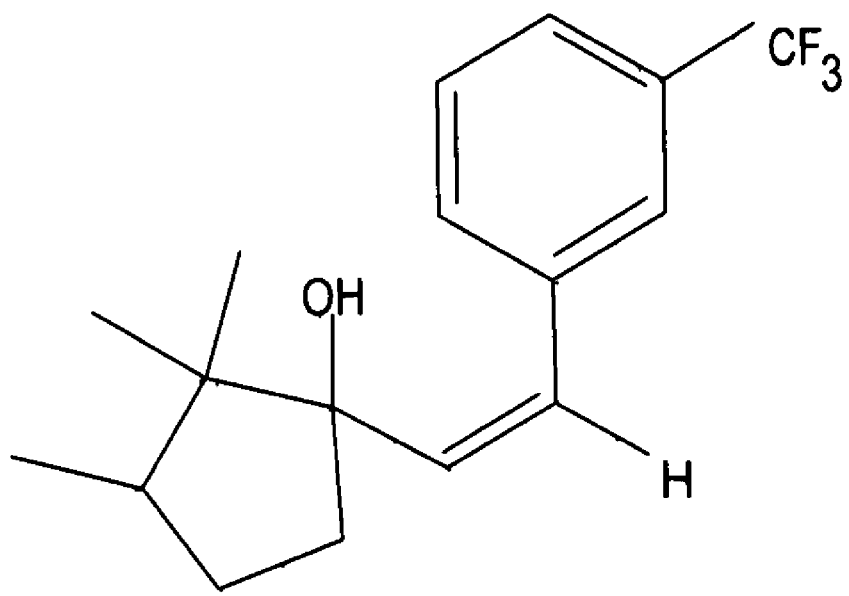
Figure 6:
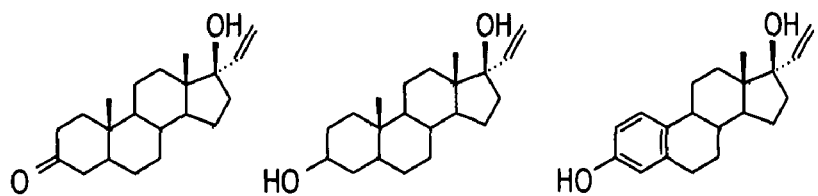
Figure 6:
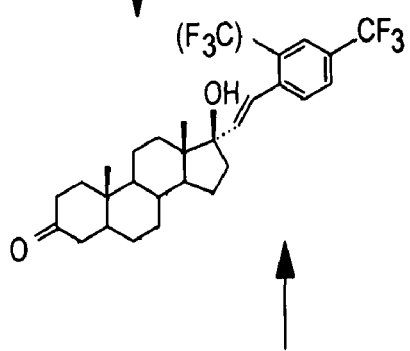
Figure 6:
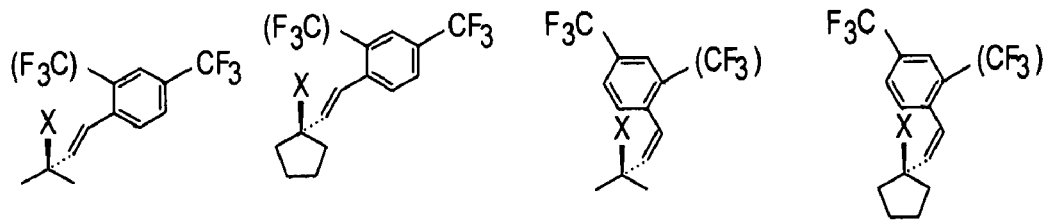
Figure 7:
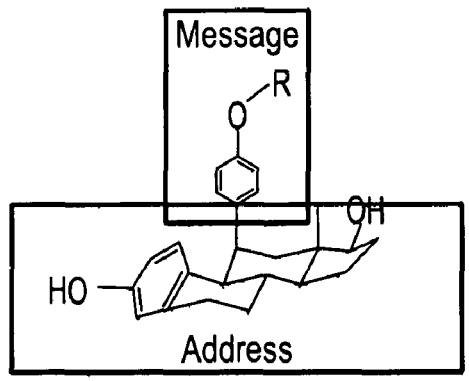
Figure 7:
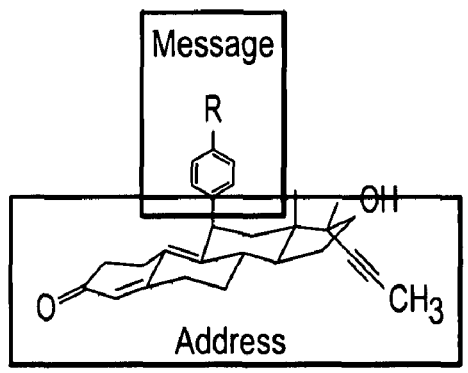
Figure 7:
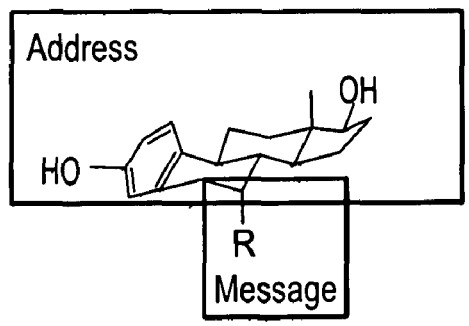
Figure 7:
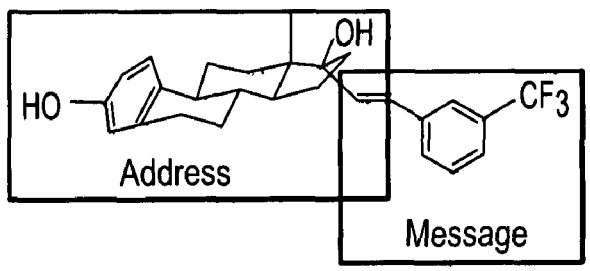
Figure 8:
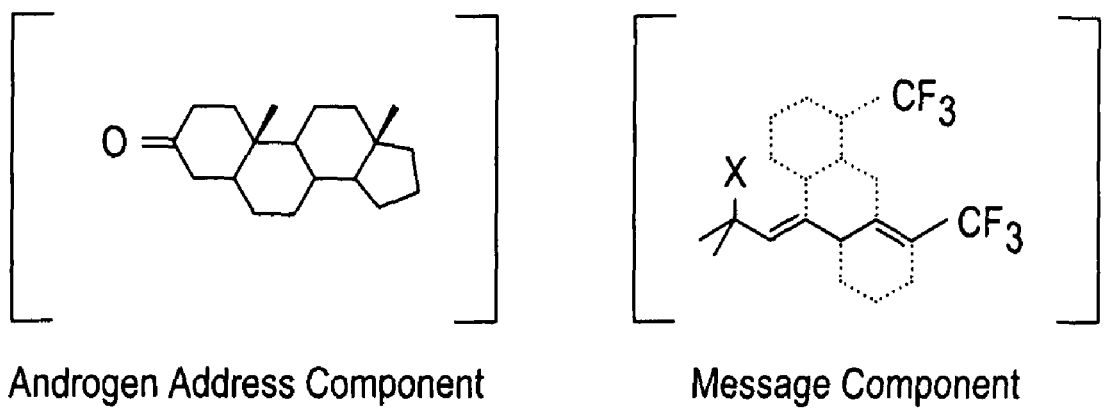
Figure 9:
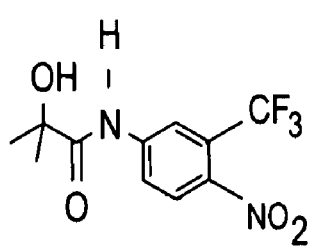
Figure 9:
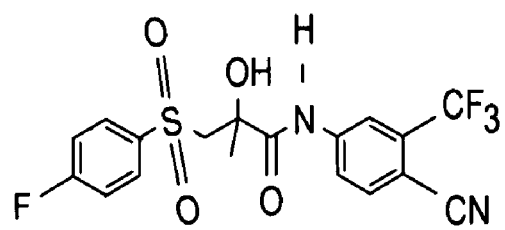
Figure 9:
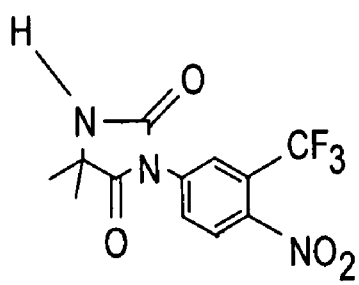
Figure 9:
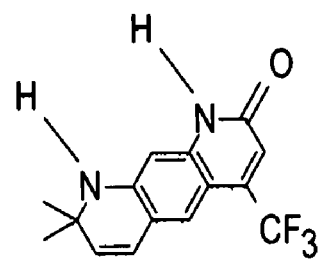
Figure 10:
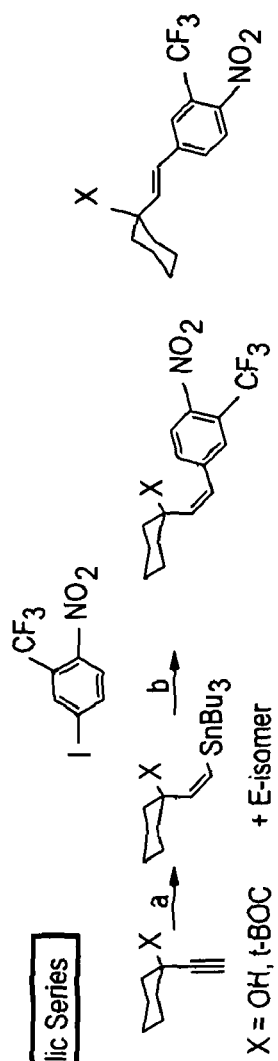
Figure 10:
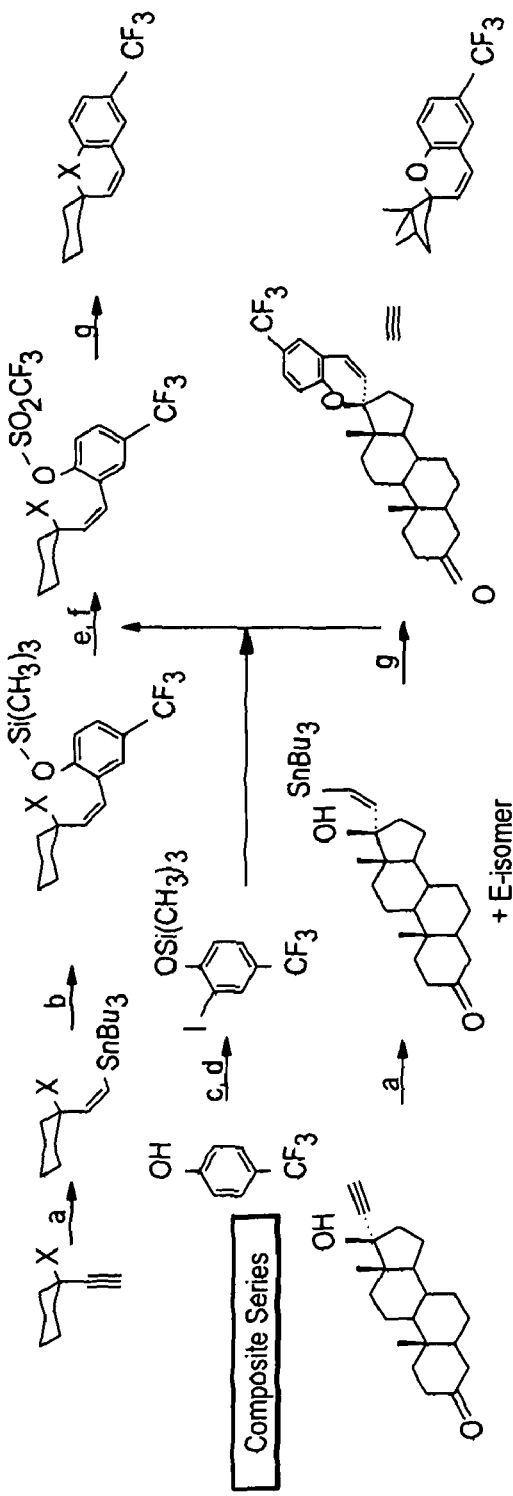
Figure 11A:
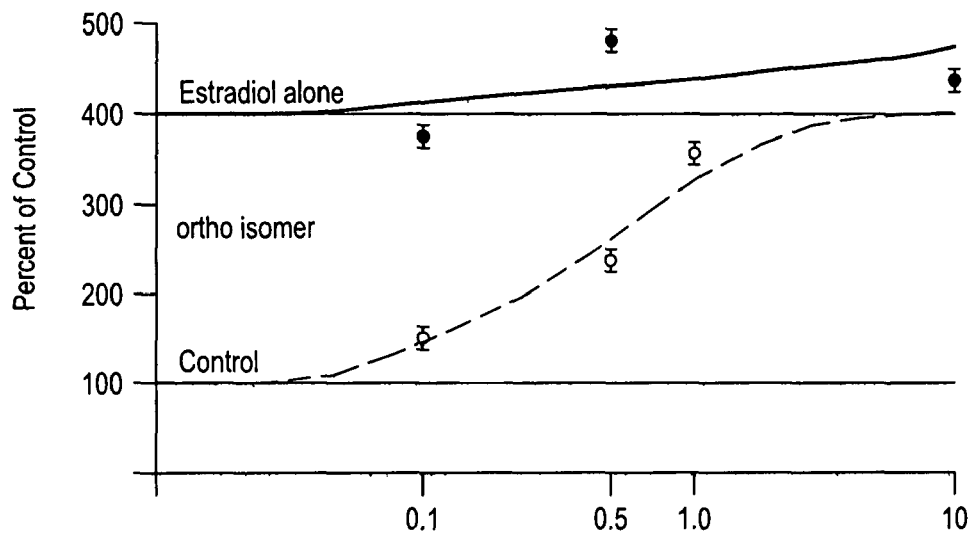
Figure 11B:
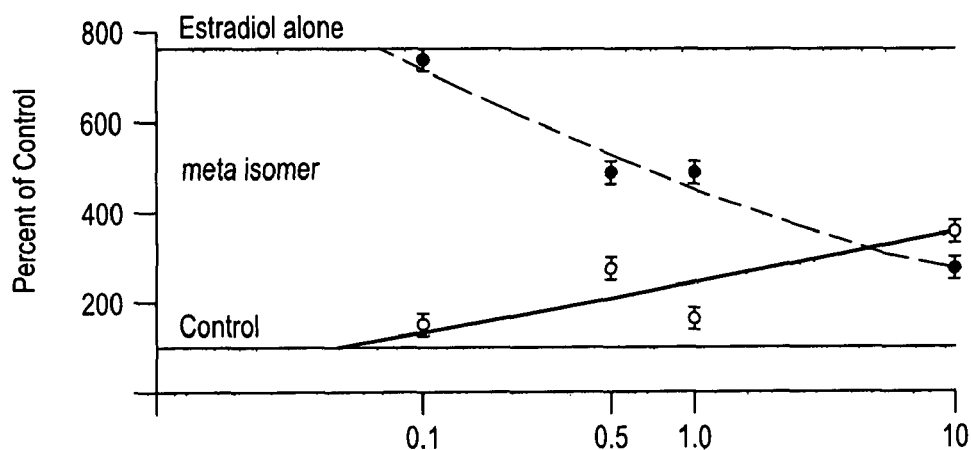
Figure 11C:
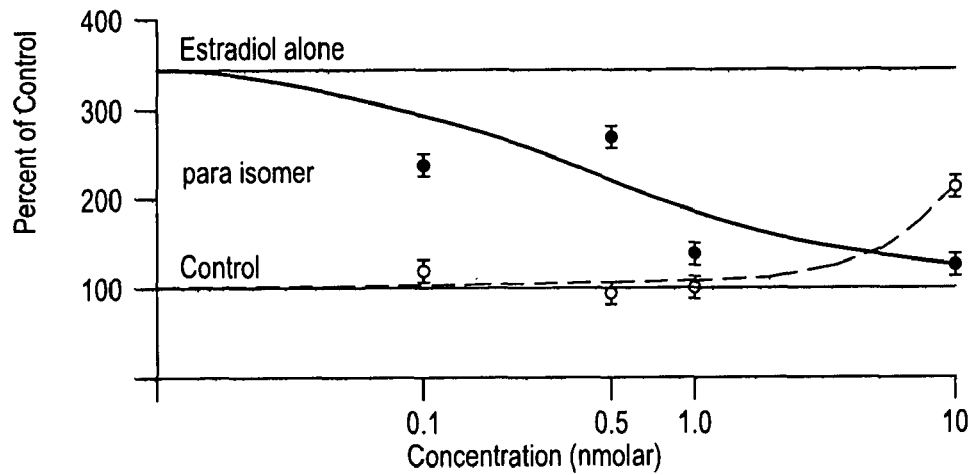
Figure 12:
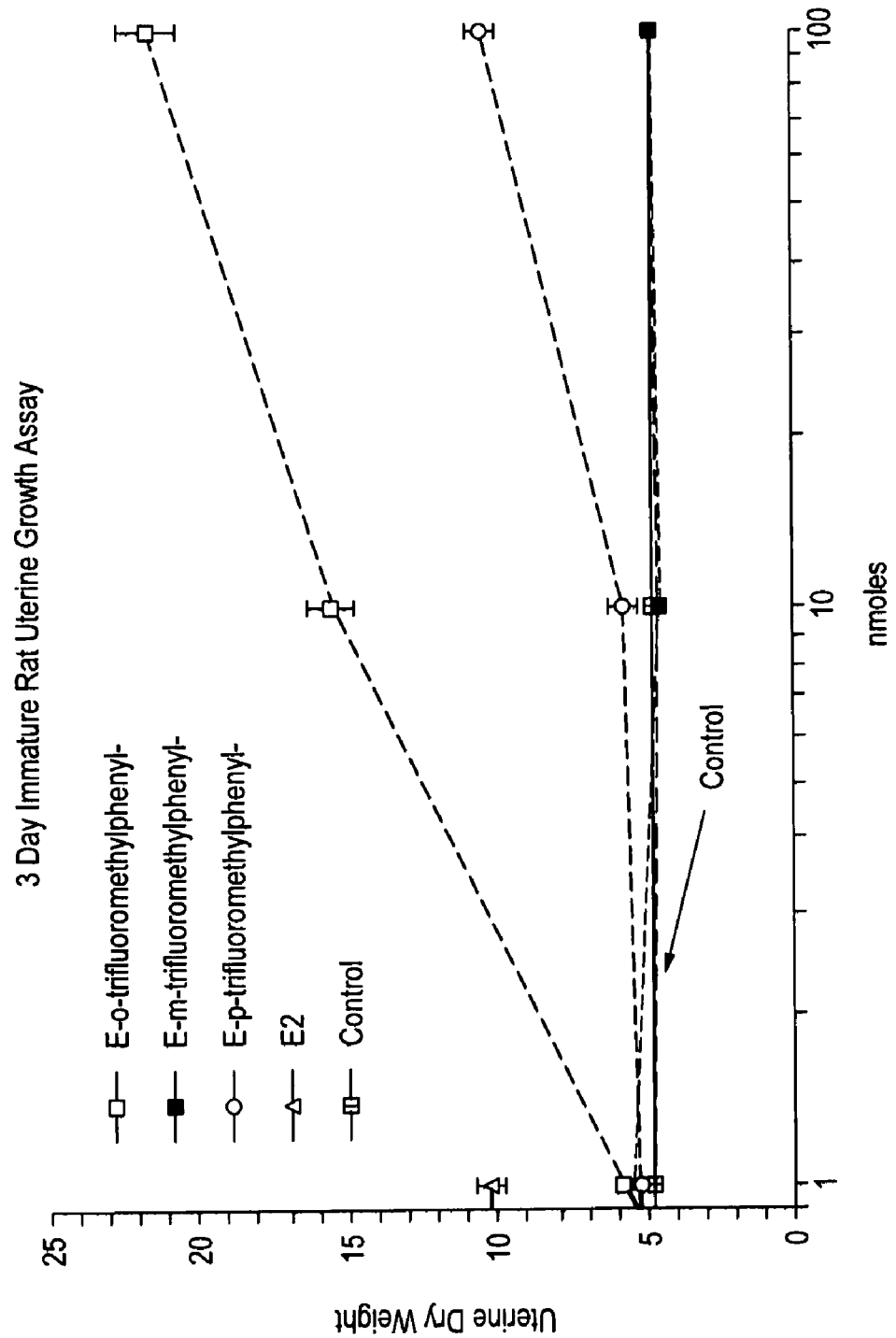
Figure 13:
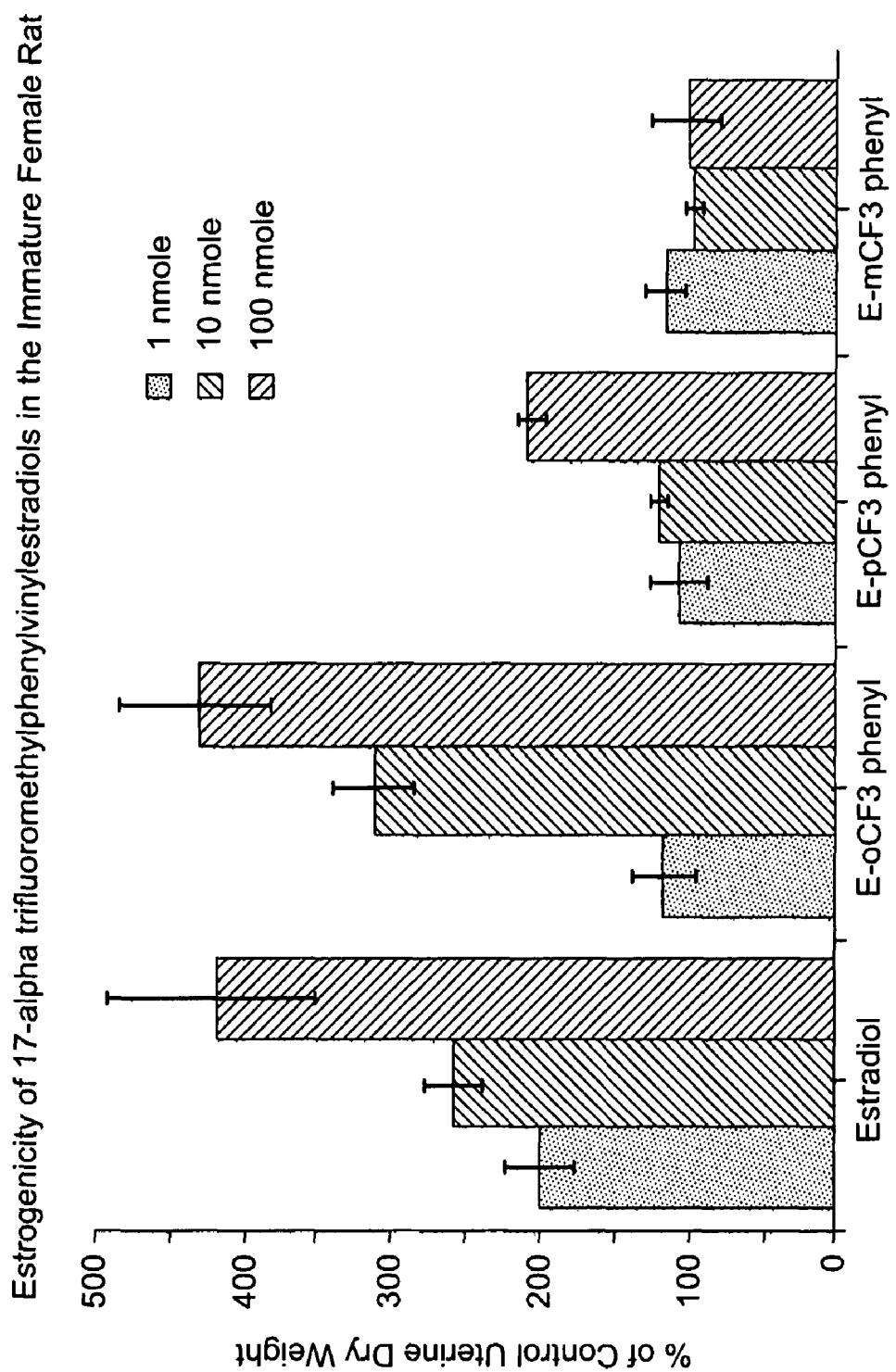

a—Jones reagent ($H_2Cr_2O_4$, $H_2SO_4$, acetone)
b—n-BuLi, TMEDA, cyclohexane, 50° C.;
c—Dry ice, THF;
d—17α-Ethynyl estradiol, DCC, DMAP, $CH_2Cl_2$;
e—$HSnBu_3$, $Et_3B$, THF, 50-60° C.;
f—17α-Ethynyl estradiol, $HSnBu_3$, $Et_3B$, THF, 50-60° C.;
g—DCC, DMAP, $CH_2Cl_2$;
h—R-Aryl-X, $Pd(PPh_3)_4$, BHT, toluene, $N_2$, reflux;
i—5 N—NaOH in $CH_3OH$-Dioxane (1:3);
j—5%-$CH_3COOH$;
k—10%-$NaHCO_3$;

FIG. 2 depicts the synthesis of an exemplary address unit;

FIG. 3 depicts the synthesis of an exemplary message unit;

FIG. 4 depicts the synthesis of an address-message combination;

FIG. 5 depicts the E and Z isomers of 3-(trifluoromethyl)phenylvinyl estradiol;

FIG. 6 depicts the exemplary composite of both the address and message units;

FIG. 7 depicts prior art antihormones that incorporate functional groups at the 11β- or 7α-position of the steroid nucleus;

FIG. 8 depicts an exemplary steroid nucleus (address component) and the nonsteroidal antagonist pharmacophore (message component);

FIG. 9 depicts prior art nonsteroidal ligands with an antiandrogen message component (Helix-12 modulators);

FIG. 10 depicts the synthesis of message components using a modified combination of organotin chemistry and palladium-catalyzed coupling reactions;

FIG. 11a-11c are graphs depicting the results of proliferation assays of MCF-7 cells with (ortho, meta, or para) 3-(trifluoromethyl)phenylvinyl estradiol;

FIG. 12 is a graph depicting the results of a three-day immature female rat uterotrophic growth assay with (ortho, meta, or para) 3-(trifluoromethyl)phenylvinyl estradiol;

FIG. 13 is a graph depicting the results of the estrogenicity of 17α-(ortho, meta, or para) 3-(trifluoromethyl)phenylvinyl estradiols in the immature female rat; and FIG. 14 is a graph depicting the results of an antiestrogen assay of 17α-(ortho, meta, or para) 3-(trifluoromethyl)phenylvinyl estradiols in the immature female rat.

DETAILED DESCRIPTION OF THE INVENTION

The term "alkyl" used herein can refer to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like. Preferred alkyl groups herein contain 1 to 12 carbon atoms. The term "lower alkyl" intends an alkyl group of one to six carbon atoms, preferably one to four carbon atoms. The term "cycloalkyl" intends a cyclic alkyl group, typically of 3 to 6 carbon atoms, more preferably 4 to 5 carbon atoms. The term "cyclooxyalkyl" intends a cyclic alkyl group containing a single ether linkage, again, typically containing 3 to 6 carbon atoms, more preferably 4 to 5 carbon atoms. By way of example, alkyl can include, but is not limited to, 1 to 10 carbons (linear, branched, cycloalkyl) with 1 or more carbons replaced singly, multiply or a combination of N, S, and O and with hydrogen replaced singly or multiply up to replacement of all hydrogen with fluorine.

The term "aryl" as used herein can refer to a monocyclic aromatic species of 5 to 7 carbon atoms, and is typically phenyl. Optionally, these groups are substituted with one to five, more preferably one to three, lower alkyl, lower fluoroalkyl, lower alkoxy, halo, nitro, amino, amide, carboxy, thioether, sulfide, sulfoxide, sulfamino, and/or sulfamide substituents. The aryl group may also comprise di-, tri-, hexa-, penta-substituted phenyl with all positional (ortho, meta, para) variations. The term "lower fluoroalkyl" intends an alkyl group of one to six carbon atoms, preferably one to four carbon atoms. By way of example, aryl can include, but is not limited to, benzene, substituted benzene, heteroarene (5- or 6-membered ring) with 1 or more carbons replaced singly, multiply or in combination with up to n−1 carbons of N, S, and O, or fused aromatics.

The term "lower alkoxy" intends an alkoxy group with one to six carbon atoms, preferably one to four carbon atoms. The term "carboxy aryl" as used herein can refer to a carboxy group attached to the aryl group.

The term "halo" or "halogen" can refer to fluoro, chloro, bromo or iodo, and usually relates to halo substitution for a hydrogen atom in an organic compound.

The term "optional" or "optionally" can mean that the subsequently described event or circumstance may or may not occur, and that the description includes instances where said event or circumstance occurs and instances where it does not.

The term "heteroaryl" as used herein can refer to monocyclic aromatic species of three to seven carbon atoms, and is preferably one to six carbon atoms, and is more preferably one to five carbon atoms, and is typically phenyl. In particular, the heteroaryl comprises, for example, oxazole, thiazole, or isoxazole, where these heteroaryls have nitrogen, oxygen, or sulfur atoms in the monocyclic ring. Optionally, these groups are substituted with one to five, more preferably one to three, lower alkyl, lower fluoroalkyl, lower alkoxy, halo, nitro, amino, amide, carboxy, thioether, sulfide, sulfoxide, sulfamino, and/or sulfamide substituents. The aryl group of a heteroaryl may also comprise di-, tri-, hexa- or penta-substituted phenyl with all positional (ortho, meta, para) variations. The term "carboxy-heteroaryl" as used herein can refer to a carboxy group attached to a heteroaryl group. By way of example, heteroaryl can be a 5- or 6-membered ring with 1 or more carbons replaced singly, multiply or in combination with up to n−1 carbons of N, S, and O, and where the aryl group thereof is substituted singly or multiply with substituents being halogens, nitro, amines, substituted amines (primary, secondary or tertiary with substituents such as alkyl, aryl, acyl, sulfonyl, alkylsulfonyl, and arylsulfonyl), cyano, carboxylic acids, esters, amides, substituted amides (primary, secondary or tertiary), ethers, aminoethers, thioethers, ketones, aldehydes, oximes, sulfonamides, substituted sulfonamides (primary, secondary or tertiary substituents such as alkyl, aryl, acyl, sulfonyl, alkylsulfonyl, and arylsulfonyl), sulfoxides, sulfones, alcohols, sulfonates, alkylsulfonates, arylsulfonates, fluoroalkanes with 1 to 10 carbons and with hydrogens replaced singly or multiply up to replacement of all hydrogen with fluorine, and aryl.

The term "fused aryl" as used herein can refer to bicyclic aromatic species of three to seven carbon atoms, and is typically phenyl. In particular, the fused aryl may comprise naphthyl, benzothienyl, or benzofuryl. Optionally, these groups are substituted with one to five, more preferably one to three, lower alkyl, lower fluoroalkyl, lower alkoxy, halo, nitro, amino, amide, carboxy, thioether, sulfide, sulfoxide, sulfamino, and/or sulfamide substituents. The aryl group of a fused aryl may also comprise di-, tri-, hexa- or penta-substituted phenyl with all positional (ortho, meta, para) variations. The term "carboxy-fused aryl" as used herein can refer to a carboxy group attached to a fused-aryl group. By way of example, fused aromatics or fused aryl can include naphthalene, indene and fluorene, with 1 or more carbons to up to n−1 carbons replaced singly, multiply or a combination of N, S, and O and with the rings substituted with substituents being halogens, nitro, amines, substituted amines (primary, secondary or tertiary), cyano, carboxylic acids, esters, amides, substituted amides (primary, secondary or tertiary with substituents such as alkyl, aryl, acyl, sulfonyl, alkylsulfonyl, and arylsulfonyl), ethers, aminoethers, thioethers, ketones, aldehydes, oximes, sulfonamides, substituted sulfonamides (primary, secondary or tertiary with substituents such as alkyl, aryl, acyl, sulfonyl, alkylsulfonyl, and arylsulfonyl), sulfoxides, sulfones, alcohols, sulfonates, alkylsulfonates, arylsulfonates and fluoroalkanes with 1 to 10 carbons and with hydrogens replaced singly or multiply up to replacement of all hydrogen with fluorine, and aryl.

The term "biaryl" as used herein can refer to two monocyclic aromatic species of four to seven carbon atoms, and is typically different configurations of a combination of a phenyl and a heteroaryl. Optionally, these groups are substituted with one to five, more preferably one to three, lower alkyl, lower fluoroalkyl, lower alkoxy, halo, nitro, amino, amide, carboxy, thioether, sulfide, sulfoxide, sulfamino, and/or sulfamide substituents. The aryl group of a biaryl may also comprise di-, tri-, hexa- or penta-substituted phenyl with all positional (ortho, meta, para) variations. The term "carboxy-biaryl" as used herein can refer to a biaryl attached to a carboxy group.

The terms "ether-linked aryls" and "ether-linked heteroaryls" as used herein refer to two aryls/heteroaryls as defined above that are linked by an ether group. Optionally, these groups are substituted with one to five, more preferably one to three, lower alkyl, lower fluoroalkyl, lower alkoxy, halo, nitro, amino, amide, carboxy, thioether, sulfide, sulfoxide, sulfamino, and/or sulfamide substituents. The aryl group of an ether-linked aryl may also comprise di-, tri-, hexa- or penta-substituted phenyl with all positional (ortho, meta, para) variations.

The terms "amine-linked aryls" and "amine-linked heteroaryls" as used herein refer to two aryls/heteroaryls as defined above that are linked by an amine group. The terms aminoalkoxy arene hybrids and peptidyl hybrids as used herein refer to the groups exemplified in Table 1. Optionally, these groups are substituted with one to five, more preferably one to three, lower alkyl, lower fluoroalkyl, lower alkoxy, halo, nitro, amino, amide, carboxy, thioether, sulfide, sulfoxide, sulfamino, and/or sulfamide substituents. The aryl group of an amine-linked aryl may also comprise di-, tri-, hexa- or penta-substituted phenyl with all positional (ortho, meta, para) variations.

The invention also relates to compounds or probes that can be characterized as hormone binding compounds, for example, estrogen receptor and/or androgen receptor as well as estrogen-like and/or androgen-like receptor binding compounds (including analogs, salts, pharmaceutical compositions, derivatives, prodrugs or racemic mixtures thereof). In one aspect, a compound or probe of the invention can be a water-soluble, non-toxic salt thereof. Preferably, a compound or probe of the invention binds to estrogen receptors and/or androgen receptors and/or estrogen-like and/or androgen-like receptors. For example, a compound or probe of the invention can bind to (with or in) tissue, which can comprise one or more estrogen receptors and/or androgen receptors (or estrogen-like and/or androgen-like receptors). A compound or probe of the invention can preferentially bind to estrogen receptors and/or androgen receptors and/or or estrogen-like and/or androgen-like receptors that are present in disease states or maladies characterized by or associated with a hormone-responsive disorder.

A receptor of interest or tissue of interest (including proteins, precursors, portions, fragments and peptides of both) can refer to any receptor or tissue. For example, a receptor or tissue of interest can refer to any hormone related receptor or tissue. In one aspect, a receptor or tissue of interest can refer to any receptor or tissue that may bind (associate or interact with) a compound or probe of the invention. Preferably, a receptor or tissue of interest can refer to any receptor or tissue that may be desired to be detected by an in vivo or in vitro method of the invention. For example, a receptor or tissue of interest can refer to any receptor or tissue or their properties or characteristics (for example, density, type, in vivo location, population, cell type) that may be desired to be detected by an in vivo or in vitro method of the invention. A receptor or tissue of interest can refer to any receptor or tissue or their properties or characteristics that one of ordinary skill in the art would understand as being correlated with or indicative of a disease state, disorder or malady such as, for example, a hormone-responsive disorder. A receptor or tissue of interest can refer to any receptor or tissue of interest or their properties or characteristics that one of ordinary skill in the art would understand as being correlated with or indicative of a disease state, disorder or malady and may bind to a compound or probe of the invention. A receptor or tissue of interest can refer to any receptor or tissue of interest or their properties or characteristics that one of ordinary skill in the art would understand as being correlated with or indicative of a disease state, disorder or malady and may be desired to be detected by an in vivo or in vitro method of the invention. A receptor or tissue of interest can refer to any receptor or tissue of interest or their properties or characteristics that one of ordinary skill in the art would understand as being correlated with or indicative of a disease state, disorder or malady, capable of binding to a compound or probe of the invention and may be desired to be detected by an in vivo or in vitro method of the invention. Each of the compounds, probes, methods, kits, assays, uses and so forth of the invention or related thereto can involve or include a receptor and/or tissue of interest.

A compound or probe of the invention can bind to one or more hormone receptors, for example, estrogen receptors and/or androgen receptors as well as estrogen-like and/or androgen-like receptors of tissues with a dissociation constant (for example, an equilibrium dissociation constant, $K_d$) from, for example, about 0.0001 to 10 μM as measured by binding to a synthetic peptide or tissue associated with a hormone-responsive disorder. The invention contemplates measurement of a dissociation constant (for example, $K_d$ and $K_i$) or performing competition, saturation and kinetics experiments by conventional techniques routine to one of ordinary skill in the art. Moreover, a compound or probe of the invention can compete with a reference compound for binding to estrogen receptors and/or androgen receptors (or estrogen-like and/or androgen-like receptors) with a dissociation constant of inhibition (for example, $K_i$) from, for example, about 0.01 nM to >10,000 nM.

"Effective amount" can refer to the amount required to produce a desired effect. One example of an effective amount includes amounts or dosages that enable detecting, quantitation and imaging of estrogen receptors and/or androgen receptors (or estrogen-like and/or androgen-like receptors) in vivo or in vitro. In one aspect, the estrogen receptors and/or androgen receptors as well as estrogen-like and/or androgen-like receptors can be found in tissues. Another example of an effective amount includes amounts or dosages that yield acceptable toxicity and bioavailability levels for imaging or therapeutic (pharmaceutical) use including, but not limited to, the treatment or prophylaxis of a hormone-responsive disorder. Another example of an effective amount includes amounts or dosages that are capable of preventing or inhibiting cell proliferation and toxicity associated with a hormone-responsive disorder. The terms "effective amount", "sufficient quantity", "sufficient amount", "effective quantity" and the like as used herein can mean a nontoxic but sufficient amount of a compound, probe or composition of the invention to provide the desired effect such as, for example, the prophylaxis or treatment of a disease state or the in vivo detection or quantitation of the disease state. The exact amount required will vary from patient to patient, depending on the species, age, and general condition of the patient, the severity of the condition being treated, and the particular compound, probe or composition and its mode of administration. Thus, it is not possible to specify an exact "effective amount, "sufficient quantity", "sufficient amount", "effective quantity", "detectable amount" or "detectable quantity". However, appropriate amounts or quantities may be determined by one of ordinary skill in the art using only routine experimentation. "Effective amount", "sufficient quantity", "sufficient amount", "effective quantity", "detectable amount" or "detectable quantity" also refer to the amount required to produce a desired effect. One example of such amounts or quantities includes amounts or dosages that enable detection or quantitation through in vivo imaging techniques. Effective amount or sufficient quantity can be a quantity of a probe or labeled compound of the invention necessary to be detected by the detection method chosen. For example, a detectable quantity can be administered in an amount sufficient to enable detection of binding of the probe or labeled compound to one or more receptor or receptor types. The amount of a probe or labeled compound to be introduced into a patient in order to provide for detection can readily be determined by those skilled in the art. For example, increasing amounts of a probe can be given to a patient until the probe is detected by the detection method of choice. A detectable marker is introduced to the compounds of the invention to provide for a probe that can be detected by suitable imaging modalities. In one aspect, a method of the invention determines the presence and location of estrogen, androgen or estrogen-like or androgen like receptors in an organ, tissue or body area, preferably, in a patient. The method comprises administration of a detectable quantity of a probe or pharmaceutical composition thereof. Another example of an effective amount includes amounts or dosages that yield acceptable toxicity and bioavailability levels for therapeutic use as well as detection and imaging type applications.

A "subject" or "patient" is a mammal, preferably, a human, and, most preferably, a human suspected of having a disease associated with a hormone-responsive disorder. The term "subject" and "patient" can be used interchangeably. Moreover, any substituents for the compounds and probes of the invention are generally understood to be described herein in the alternative or, as appropriate, in a conjunctive manner. For example, a compound or probe of the invention can comprise substituents such as F, Cl, Br, I in the alternative or, as appropriate, in a conjunctive manner.

For brain imaging, preferably, the amount (total or specific uptake) of a bound probe of the invention (such as a probe that is radioactively labeled with a detectable marker) is measured and compared (as a ratio) with the uptake of a labeled compound of the invention, which may be a probe, bound to the cerebellum of the patient. This ratio is then compared to the same ratio in one or more age-matched normal brains. Preferably, a probe of the invention is administered intravenously to a patient in an amount or dosage appropriate for in vivo imaging of estrogen receptors and/or androgen receptors. The compounds and probes of the invention can also be administered via a pharmaceutically acceptable carrier. In one aspect, a compound of the invention can be administered for the treatment or prophylaxis of a disease. For example, a compound of the invention can be included in a composition comprising a pharmaceutically acceptable carrier. An exemplary composition contains human serum albumin and a compound of the invention.

Probes can comprise labeled (marked or tagged) compounds for imaging or detection (for example, identifying, diagnosing, evaluating and/or quantitating in vivo or in vitro) at least one estrogen receptor and/or androgen receptor or a hormone-responsive disorder. Probes can bind (associated or interact) to a receptor of interest including a receptor (for example, hormone receptor) from tissues comprising proteins, precursors, portions, fragments and peptides of the receptor of interest. The binding of probes to tissues or receptors of interest (as well as any proteins, precursors, portions, fragments and peptides thereof) can be of high-affinity and a specific or preferential nature as would be understood by one of ordinary skill in the art and evaluated by conventional techniques related to binding (for example, dissociation constants). The probes of the invention can include analogs, salts, pharmaceutical compositions, derivatives, prodrugs or racemic mixtures thereof.

Compounds of the invention can comprise tissue or receptor (for example, a hormone receptor) binding compounds. A binding compound of the invention can be labeled with any suitable marker (radiolabel or tag) to provide or comprise a probe for imaging or detection (for example, identifying, diagnosing, evaluating and/or quantitating in vivo or in vitro) at least one estrogen receptor and/or androgen receptor (or estrogen-like and/or androgen-like receptor) or a hormone-responsive disorder. The compounds of the invention can bind (associated or interact) to a receptor of interest including a receptor from tissues comprising proteins, precursors, portions, fragments and peptides of the receptor of interest. The binding of compounds to tissues or receptors of interest (as well as any proteins, precursors, portions, fragments and peptides thereof) can be of high-affinity and a specific or preferential nature as would be understood by one of ordinary skill in the art and evaluated by conventional techniques related to binding (for example, dissociation constants). The compounds of the invention can include analogs, salts, pharmaceutical compositions, derivatives, prodrugs or racemic mixtures thereof.

The term "in vivo" or "in vitro" in the context of detection or imaging can refer to any method that permits the detection of a probe of the invention or labeled compound. Similarly, an "in vivo method for detecting" or "in vitro method for detecting" as well as "use in detection" can comprise any type of detection for a compound or probe of the invention. Exemplary techniques for detection for a compound or probe of the invention include scintigraphy, radioscintigraphy, magnetic resonance imaging (MRI), chemilumensence, near infrared luminescence, fluorescence, SPECT, computed tomography (CT scan), positron emission tomography (PET) or combinations thereof and detection and related techniques are understood by those of ordinary skill in the art. Moreover, detection can include any future developed techniques related to the field of imaging. For gamma-based imaging, the radiation emitted from the organ or area being examined is measured and expressed either as total uptake or as a ratio in which total uptake in one tissue is normalized to (for example, divided by) the total uptake in another tissue of the same subject during the same in vivo imaging procedure. Total uptake in vivo is defined as the entire signal detected in a tissue by an in vivo imaging technique without the need for correction by a second administration of an identical quantity of a probe or labeled compound along with a large excess of unlabeled, but otherwise chemically identical, compound. Similarly, in vitro methods can involve obtaining a fresh or frozen tissue specimen and incubating a section of the tissue or a homogenate of the tissue with a labeled compound of the invention and then separating bound and free radiolabel by washing the tissue section or filtering and washing the tissue homogenate. The bound radioactivity can be measured by standard autoradiographic techniques or by liquid scintillation or gamma counting and compared to controls from the same tissue to which an excess of unlabeled compounds has been added.

The ability of a compound or probe of the invention to preferentially (or specifically) bind to (with or in) tissues or receptors of interest may vary depending on concentration, although the determination of specific concentrations to achieve binding that can be effective for therapy and/or imaging (for example, identifying, diagnosing, evaluating, detecting and/or quantitating techniques) would be routine to the skilled artisan. For example, the probes or labeled compounds may be specific for tissues or receptors at concentrations less than 50 nM. These low concentrations are also detectable with imaging studies including PET. The use of the probes or labeled compounds of the invention also permits detection of estrogen receptors and/or androgen receptors (or estrogen-like and/or androgen-like receptors) such as those found in tissues including, but not limited to, the brain.

In one aspect, a compound or probe of the invention is administered to a patient in an amount or dosage suitable for therapeutic use or in vivo imaging. Generally, a unit dosage comprising a compound or probe of the invention will vary depending on patient considerations. Such considerations include, for example, age, protocol, condition, sex, extent of disease, contraindications, concomitant therapies and the like. An exemplary unit dosage based on these considerations can also be adjusted or modified by a physician skilled in the art. For example, a unit dosage for a patient comprising a probe can vary from $1 \times 10^{-15}$ g/kg to 10 g/kg, preferably, $1 \times 10^{-15}$ g/kg to 1.0 g/kg. Moreover, a unit dosage comprising a probe can also be from 1 µCi/kg to 10 mCi/kg and, preferably, 0.1 mCi/kg. Dosage of a compound or probe of the invention can also vary from 0.001 µg/kg to 10 µg/kg or, preferably, from 0.01 µg/kg to 1.0 µg/kg.

The term "pharmaceutically acceptable" as used herein can mean a material which is not biologically or otherwise undesirable, i.e., the material may be administered to a patient along with the selected compound or probe without causing any undesirable biological effects or interacting in a deleterious manner with any of the other components of the pharmaceutical composition in which it is contained.

The present invention also comprises the design, synthesis and development of a new class of chemotherapeutic agents for the treatment of hormone-responsive disorders. In the new class of chemotherapeutic agents, two components—a message subunit or pharmacophore, present in the nonsteroidal antagonists (e.g., antiandrogens, antiestrogens) and the address subunit found in the steroidal agonists (e.g., androgens, estrogens)—are combined into a single composite entity. In particular, specific compounds in this new class of chemotherapeutic agents target the estrogen and/or the androgen receptors (or estrogen-like and/or androgen-like receptors). The general formula for the agents of the invention was determined based on the discovery that the interaction between androgen/estrogen with the receptor involves a two step process. There is an initial association of the hormone (address component) with a specific part of the receptor, called the hormone binding domain, followed by the induction of a conformational change in the receptor (message component) that generates the observed biological response.

Accordingly, the present invention incorporates the "address-message" concept to generate, for example, prostate cancer tissue affinity, selectivity, and efficacy, and employs transition metal catalysts/reagents to prepare the novel compounds or probes thereof of the invention. In one aspect, the present invention uses modified palladium catalysts for carbon-carbon (Stille, Suzuki reactions) and carbon-nitrogen/oxygen (Buchwald, Hartwig) coupling reactions. In another aspect of the present invention, the use of 1D/2D-NMR (Nuclear Magnetic Resonance) and the molecular modeling in the evaluation of the conformational analysis of a target compound provides the capability for biological and structural data.

In the methods of the invention, data collection using conventional and developing technologies can be conducted according to standard clinical imaging protocols involving whole body imaging techniques such as repeatedly moving the subject through the scanner over the course of the scanning period. In one aspect, data collection may be achieved by imaging selectively over one or more regions of interest in the body, for example, by emphasizing the brain, lungs, liver, heart or kidneys using a limited range of patient body coverage in an imaging scanner. Following the administration of a compound or probe of the invention, imaging data collection can begin immediately and proceed for several hours post administration using a dynamic imaging protocol. Late-time snapshots of about 30 minutes could also be taken following the in vivo distribution of the compound or probe using standard static late time imaging protocols. Imaging data can then be collected and stored electronically in an automated and routine fashion, for later processing and analysis. Data processing and analysis can make use of commercially available software packages, which are typically installed by the manufacturer on the single photon, positron emission or magnetic resonance scanners' operating system computers.

Examples of these processes and methods for detecting, collecting and processing imaging data are established in the art for positron emission methodologies. Price et al., J. Cereb. Blood Flow Metab., 25: 1528 (2005) and Lopresti et al., Nuclear Medicine, 46: 1959 (2005). Analogous data collection and processing of single photon, positron and magnetic resonance species are similarly conducted for systemic estrogen or androgen receptors using standard, commercially available scanners, data collection methodologies and data processing techniques in body regions including the brain.

As indicated, the specific method of detection of a compound or probe of the invention can vary, depending upon the chemical and physical nature of the species utilized and detected. For gamma-emitting species, standard, commercially available single photon and positron detection methods can be utilized. For magnetic nuclear spin detection, standard, commercially available magnetic resonance imaging and spectroscopy techniques can be utilized.

The invention also provides a method for the treatment or prophylaxis of a disease characterized by hormone-responsive disorder comprising administering to a patient in need thereof an effective amount of a compound of the invention. In one aspect, the method can include providing a patient suffering from or believed to be at risk of suffering from a disease characterized by, for example, a hormone-responsive disorder. The method may also comprise administering to the patient an effective amount of a compound of the invention. The compound of the invention can also be administered as part of a composition comprising a pharmaceutically acceptable carrier.

The novel compounds and probes thereof constitute a structurally unique class of steroidal derivatives, e.g., derivatives of, for example, 17α-(substituted)phenylvinyl-17β-estradiols as estrogens and antiestrogens, and corresponding (nor)testosterones and dihydro-derivatives. In particular, identification of the most potent and selective antagonists for prophylaxis and treatment provides for a more effective treatment of hormone-responsive disorders and thereby prolong the disease-free interval. The present invention provides for a more potent and effective agent which increases the initial response coupled with a slower progression to hormone independence. Additionally, the compound of the present invention targets specifically and more selectively thereby reducing the incidence and/or severity of the side effects of anti-estrogen or anti-androgen therapy.

In one aspect, a method is provided for administering an effective amount of one or more compounds of the invention to a patient suffering from or believed to be at risk of suffering from a disease or disease state such as, for example, those identified herein including osteoporosis, endometriosis, breast cancer, benign breast cancer, uterine cancer, ovarian cancer, polycystic ovarian disease, prostate cancer, benign prostatic hyperplasia (BPH), cardiac diseases, coronary artery disease, acne, seborrhea, alopecia, hirsutism, male pattern baldness, and infertility. The method also comprises administering, either sequentially or in combination with one or more compounds or probes of the invention, a conventional therapeutic agent in a sufficient amount that can potentially be effective for the treatment or prophylaxis of a disease state. Exemplary conventional therapeutic agents include Lupron (leuprolide acetate), Zoladex (goserelin acetate implant), aromatase inhibitors (such as, for example, Arimidex®, Aromasin, Femara), herceptin, doxorubicin, and paclitaxol.

The invention also provides a method of distinguishing a normal tissue (for example, brain) from one indicative of a disease state or malady. In one aspect, the method comprises obtaining tissue samples from the cerebellum and another area of the brain of a normal subject. Furthermore, the method includes obtaining comparable tissue samples from subjects suffering from or suspected of suffering from a disease such as, for example, a hormone-responsive disorder. These tissue samples are made into separate homogenates using methods well known to the skilled artisan and are then incubated with a probe of the invention. The amount of tissue that binds to the probe is calculated for each tissue sample type, for example, cerebellum, non-cerebellum, normal or abnormal and a ratio for the binding of non-cerebellum to cerebellum tissue is calculated. These ratios are may also be compared to each other. In one aspect, if the ratio from the brain suspected of having a disease is above about 40%, 50%, 60%, 70%, 80% or 90% (preferably, for example, above 50% and, more preferably, for example, above 90%) of the ratios obtained from normal brains, the diagnosis of a disease state is made. The normal ratios can be obtained from previously obtained data or, alternatively, they may be recalculated at the same time the suspected brain tissue is studied via a method of the invention.

The compounds and probes of the invention also include analogs, salts, pharmaceutical compositions, derivatives, prodrugs, racemic mixtures or tautomeric forms thereof. Moreover, any methods, kits or uses (including, for example, those herein) for a compound or probe of the invention can be performed with or employ one or more such analogs, salts, pharmaceutical compositions, derivatives, prodrugs, racemic mixtures or tautomeric forms.

The invention also provides methods for preparing compounds or probes of the invention. In one aspect, one or more of the compounds can be modified to be a probe of the invention. The probes of the invention are particularly useful for the in vivo diagnosis and study of the progression or regression of disease states or maladies in a patient. Exemplary disease states or maladies include, without limitation, osteoporosis, endometriosis, breast cancer, benign breast cancer, uterine cancer, ovarian cancer, polycystic ovarian disease, prostate cancer, benign prostatic hyperplasia (BPH), cardiac diseases, coronary artery disease, acne, seborrhea, alopecia, hirsutism, male pattern baldness, and infertility.

A compound or amyloid probe of the invention can also be modified, for example, by the covalent attachment of an organic moiety or conjugate to improve pharmacokinetic properties, toxicity or bioavailability (e.g., increased in vivo half-life). The conjugate can be a linear or branched hydrophilic polymeric group, fatty acid group or fatty acid ester group. A polymeric group can comprise a molecular weight that can be adjusted by one of ordinary skill in the art to improve, for example, pharmacokinetic properties, toxicity or bioavailability. Exemplary conjugates can include a polyalkane glycol (e.g., polyethylene glycol (PEG), polypropylene glycol (PPG)), carbohydrate polymer, amino acid polymer or polyvinyl pyrolidone and a fatty acid or fatty acid ester group, each of which can independently comprise from about eight to about seventy carbon atoms. Conjugates for use with a compound or amyloid probe of the invention can also serve as linkers to, for example, any suitable substituents or groups, radiolabels (marker or tags), halogens, proteins, enzymes, polypeptides, other therapeutic agents (for example, a pharmaceutical or drug), nucleosides, dyes, oligonucleotides, lipids, phospholipids and/or liposomes. In one aspect, conjugates can include polyethylene amine (PEI), polyglycine, hybrids of PEI and polyglycine, polyethylene glycol (PEG) or methoxypolyethylene glycol (mPEG). A conjugate can also link a compound of the invention to, for example, a label or marker (radionuclide, radioisotope and/or isotope) to comprise a probe of the invention. Conjugates for use with a compound or probe of the invention can, in one aspect, improve in vivo half-life. Other exemplary conjugates for use with a compound or probe of the invention as well as applications thereof and related techniques include those generally described by U.S. Pat. No. 5,672,662, which is hereby incorporated by reference herein.

Lipids can include synthetic or naturally-occurring compounds, which are generally amphipathic and biocompatible. The lipids typically comprise a hydrophilic component and a hydrophobic component. Exemplary lipids include fatty acids, neutral fats, phosphatides, glycolipids, aliphatic alcohols, waxes, terpenes, steroids and surfactants. "Lipid composition" can refer to a composition which comprises a lipid compound, typically in an aqueous medium. Exemplary lipid compositions include suspensions, emulsions and vesicle compositions. Similarly, liposome can refer to a generally spherical cluster or aggregate of amphipathic compounds (including lipid compounds) typically in the form of one or more concentric layers, for example, bilayers. They may also be referred to herein as lipid vesicles. The liposomes may be formulated, for example, from ionic lipids and/or non-ionic lipids.

The terms "tissue" or "organ" can mean a part of a patient's body. Examples of tissues or organs include the brain, heart, liver, blood vessels, arteries and so forth. A tissue can also be a tumor or cell. A detectable or imaging effective quantity is a quantity of a probe or labeled compound of the invention necessary to be detected by the detection method chosen. For example, a detectable quantity can be an administered amount sufficient to enable detection of binding of the probe to tissues or receptors of interest. The amount of a probe to be introduced into a patient in order to provide for detection can readily be determined by those skilled in the art. For example, increasing amounts of the probe can be given to a patient until the probe is detected by the detection method of choice. A detectable marker is introduced to the compounds of the invention to provide for a probe that can be detected by suitable imaging modalities. In one aspect, a method of the invention determines the presence and location of estrogen or androgen receptors in an organ or body area, preferably, the brain of a patient. The method comprises administration of a detectable quantity of a probe or pharmaceutical composition thereof. The tissue or organ can also be a receptor rich tissue such as, for example, an estrogen and/or androgen receptor rich tissue, which can include tissues comprising one or more receptors.

Those skilled in the art are also familiar with determining the amount of time sufficient for a compound or probe to become associated with tissues or receptors. The amount of time necessary can easily be determined by introducing a detectable amount of a probe of the invention into a patient and then detecting the probe at various times after administration.

The terms "associated" and/or "binding" and forms thereof can mean a chemical or physical interaction between a compound or probe of the invention and a tissue or receptor (for example, a hormone receptor). In one aspect, a tissue or receptor thereof can comprise proteins or precursors, portions, fragments and peptides. Preferably, the compounds of the invention and probes thereof are binding compounds. Examples of associations or interactions include covalent bonds, ionic bonds, hydrophilic-hydrophilic interactions, hydrophobic-hydrophobic interactions and complexes. Associated can also refer generally to "binding" or "affinity" as each can be used to describe various chemical or physical interactions. Measuring binding or affinity is also routine to those skilled in the art. For example, compounds or probes of the invention can bind to or interact with tissues, receptors or proteins, precursors, portions, fragments and peptides thereof. Those skilled in the art are familiar with the various ways to detect labeled compounds. For example, MRI, PET or SPECT can be used to detect probes of the invention. The label that is introduced to a compound of the invention to yield a probe can depend on the detection method desired. As indicated, if PET is selected as a detection method, the probe must possess a positron-emitting atom such as $^{11}C$ or $^{18}F$.

In one aspect, binding, interaction or association with can mean the contact between a compound or probe (or analogs, salts, pharmaceutical compositions, derivatives, prodrugs or racemic mixtures thereof) and a tissue or receptor of interest (e.g., a hormone receptor such as, but not limited to, a receptor rich tissue and/or an estrogen, androgen, estrogen-like, androgen-like receptor) with a binding affinity of at least $10^{-6}$ M, preferably, at least about $10^{-7}$ M, and more preferably $10^{-8}$ M to $10^{-9}$ M, $_{10}$ M, $10^{-11}$ M, or $10^{12}$ M. In one aspect, binding affinities include those with a dissociation constant or $K_d$ less than, but not limited to, $5\times10^{-6}$M, $10^{-6}$M, $5\times10^{-7}$M, $10^{-7}$M, $5\times10^{-8}$M, $10^{-8}$M, $5\times10^{-9}$M, $10^{-9}$M, $5\times10^{-10}$M, $10^{-10}$M, $5\times10^{-11}$M, $10^{-11}$M, $5\times10^{-12}$M, $10^{-12}$M, $5\times10^{-13}$M, $10^{-13}$M, $5\times10^{-14}$M, $10^{-14}$M, $5\times10^{-15}$M, and $10^{-15}$M.

In one aspect, the probe should also have sufficient radioactivity and radioactivity concentration to assure reliable diagnosis. Without limitation, for $^{99m}$Tc, the probe may be included usually in an amount from 0.1 to 10 mCi in about 0.5 to 5.0 ml at the time of administration. The amount of a compound of the invention may be such as is sufficient to form a stable chelate compound or probe with the radioactive metal.

The imaging of tissue can also be carried out quantitatively so that the amount of receptors thereof can be determined. In one aspect, probes for imaging include a radioisotope such as $^{123}$I, $^{125}$I, $^{124}$I, $^{131}$I, $^{18}$F, $^{75}$Br or $^{76}$Br. The invention also provides a method of imaging receptors. One of the prerequisites for an in vivo imaging agent of the brain is the ability to cross the intact blood-brain barrier after, for example, a bolus intravenous injection.

In another aspect, a method of inhibiting cell proliferation is provided. For example, the invention provides a method of inhibiting cell proliferation as associated with a hormone-responsive disorder. by administering to a patient an effective amount of a compound of the invention.

Those skilled in the art are readily able to determine an effective amount by simply administering a compound of the invention to a patient in increasing amounts until cell proliferation slows or stops. The rate of proliferation can be assessed using in vivo imaging, as described, or by taking a tissue sample from a patient and observing the extent of proliferation therein. The compounds of the invention can be administered to a patient at dosage levels in the range of about 0.1 to about 1,000 mg per day. For a normal human adult having a body weight of about 70 kg, a dosage in the range of about 0.01 to about 100 mg per kilogram of body weight per day is sufficient. The specific dosage used, however, can vary or may be adjusted as considered appropriate by those of ordinary skill in the art. For example, the dosage can depend on a number of factors including the requirements of the patient, the severity of the condition being treated and the pharmacological activity of the compound being used. The determination of optimum dosages for a particular patient is well known to those skilled in the art.

In one aspect, a method of the invention comprises administration of a detectable quantity of a probe to a patient. For example, a probe may be derived from a compound of the invention such as those described herein. A probe may be administered to a patient as a pharmaceutical composition or a pharmaceutically acceptable salt, preferably, water-soluble, thereof.

"Pharmaceutically acceptable salt" can refer to an acid or base salt of a compound or probe of the invention, which possesses the desired pharmacological activity and is neither biologically nor otherwise undesirable. Pharmaceutically acceptable salt can also refer to those carboxylate salts or acid addition salts of the compounds or probes of the invention, which are suitable for use in contact with the tissues of patients without undue toxicity, irritation, allergic response and the like. The salt can refer to the relatively nontoxic, inorganic and organic acid addition salts of compounds or probes of the present invention and may be formed with acids that include, without limitation, acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride hydrobromide, hydroiodide, 2-hydroxyethane-sulfonate, lactate, maleate, methanesulfonate, 2-naphthalenesulfonate, nicotinate, oxalate, thiocyanate, tosylate and undecanoate. Examples of a base salt include, without limitation, ammonium salts, alkali metal salts such as sodium and potassium salts, alkaline earth metal salts such as calcium and magnesium salts, salts with organic bases such as dicyclohexylamine salts, N-methyl-D-glucamine and salts with amino acids such as arginine and lysine. Also included are those salts derived from non-toxic organic acids such as aliphatic mono and dicarboxylic acids, phenyl-substituted alkanoic acids, hydroxy alkanoic and alkanedioic acids, aromatic acids and aliphatic and aromatic sulfonic acids. These salts can be prepared in situ during the final isolation and purification of the compounds or by separately reacting the purified compound in its free base form with a suitable organic or inorganic acid and isolating the salt thus formed. Further representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactiobionate and laurylsulphonate salts, propionate, pivalate, cyclamate, isethionate and the like. These may include cations based on the alkali and alkaline earth metals such as sodium, lithium, potassium, calcium, magnesium and the like as well as nontoxic ammonium, quaternary ammonium and amine cations including, for example, ammonium, tetramethylammonium, tetraethylammonium, methylamine, dimethylamine, trimethylamine, triethylamine, ethylamine and the like. Berge S. M., et al., Pharmaceutical Salts, J. Pharm. Sci., 66: 1 (1977).

In one aspect, a probe of the invention is administered to a patient in an effective amount or dosage suitable for in vivo imaging. For example, a probe may also comprise one or more compounds of the invention and at least one detectable marker such as, for example, a radionuclide, radioisotope or isotope. The selection of detectable markers for a probe of the invention can vary depending on the particular modality chosen for in vivo imaging. Generally, a unit dosage comprising a probe of the invention will also vary depending on patient considerations. Such considerations include, for example, age, condition, sex, extent of disease, contraindications, concomitant therapies and the like. An exemplary unit dosage based on these considerations can also be adjusted or modified by a physician skilled in the art. For example, a unit dosage for a patient comprising a probe can vary from 1× $10^{-15}$ g/kg to 10 g/kg, preferably, 1×$10^{-15}$ g/kg to 1.0 g/kg. Moreover, a unit dosage comprising a probe can also be from 1 µCi/kg to 10 mCi/kg and, preferably, 0.1 mCi/kg.

Administration of a compound or probe of the invention to a subject may be local or systemic and accomplished intravenously, intraarterially, intrathecally (via the spinal fluid) or the like. Administration may also be intradermal or intracavitary, depending upon the body site under examination. In one aspect, after a sufficient time has elapsed for a probe of the invention to bind with a receptor, for example, 5 minutes to 48 hours, the area of the subject under investigation is examined by routine imaging techniques or modalities such as magnetic resonance spectroscopy (MRS), magnetic resonance spectroscopy imaging (MRI), positron emission tomography (PET), single-photon emission computed tomography (SPECT), planar scintillation imaging or combinations thereof as well as any emerging imaging modalities. The exact protocol will necessarily vary depending upon factors specific to the patient and depending upon the body site under examination, method of administration and type of probe or detectable marker used, although the determination of specific procedures would be routine to the skilled artisan.

For tissue imaging, preferably, the amount (total or specific binding) of a bound probe of the invention (such as a probe that is radioactively labeled with a detectable marker) can be measured and, optionally, compared (as a ratio) as understood by those of ordinary skill in the art. This ratio can also then be compared to the same ratio in one or more age-matched normal tissues. Preferably, a probe of the invention is administered intravenously to a patient in an amount or dosage appropriate for in vivo imaging. The compounds and probes of the invention can also be administered via a pharmaceutically acceptable carrier. For example, a compound or probe of the invention can be included in a composition comprising a pharmaceutically acceptable carrier. An exemplary composition contains human serum albumin and a compound or probe of the invention.

The compounds or probes of the invention can also be administered in the form of injectable compositions, but may also be formulated into well known drug delivery systems such as, for example, oral, rectal, parenteral (intravenous, intramuscular, or subcutaneous), intracisternal, intravaginal, intraperitoneal, local (powders, ointments or drops) or as a buccal or nasal spray. The compounds or probes of the invention can also be administered as part of a drug delivery system comprising emulsions, liposomes, targeted liposomes, micelles, targeted micelles, nanoparticles and the like. As described, administration of a compound or probe of the invention may also be local or systemic and accomplished intravenously, intraarterially, intrathecally (via the spinal fluid) or the like. A typical composition for administration can comprise a pharmaceutically acceptable carrier for the compound or probe of the invention. A pharmaceutically acceptable carrier includes such carriers as, for example, aqueous solutions, non-toxic excipients including salts, preservatives, buffers and the like, which are described in Remington's Pharmaceutical Sciences, 15th Ed. Easton: Mack Publishing Co., pp. 1405-1412 and 1461-1487 (1975) and The National Formulary XIV., 14th Ed. Washington: American Pharmaceutical Association (1975).

Exemplary pharmaceutically acceptable carriers for a compound or probe of the invention can also include non-aqueous solvents such as propylene glycol, polyethylene glycol and vegetable oil or injectable organic esters such as ethyl oleate. An aqueous carrier can also include, without limitation, water, alcoholic/aqueous solutions, saline solutions and parenteral vehicles such as sodium chloride or Ringer's dextrose. Intravenous carriers for administration of a compound or probe of the invention include, for example, fluid and nutrient replenishers. Preservatives for a compound or probe of the invention also may include antimicrobial solutions, anti-oxidants, chelating agents and inert gases. The pH and exact concentration of the various components for a pharmaceutical composition can also be adjusted according to routine skills in the art. Goodman and Gilman's The Pharmacological Basis for Therapeutics (7th Edition).

The invention employs probes which, in conjunction with noninvasive imaging techniques or modalities such as MRS, MRI, PET or SPECT, are used to quantify in vivo characteristics. The methods of the invention also involve imaging a patient to establish a baseline. The term "baseline" can refer to the amount and distribution of a patient's receptors prior to initiation of a therapy. An exemplary method of the invention comprises at least one imaging session of a patient following administration of a therapy. In one aspect, a method of the invention may involve imaging a patient before and after treatment. For example, treatment of the patient can comprise administration of an effective amount of a compound of the invention. In vivo imaging may also be performed at any time during the treatment.

In vivo imaging generally can refer to any method that permits the detection of a probe of the invention or labeled compound. For gamma-based imaging, the radiation emitted from the organ or area being examined can be measured and expressed either as total binding or as a ratio in which total binding in one tissue is normalized to (for example, divided by) the total binding in another tissue of the same subject during the same in vivo imaging procedure. Total binding in vivo is defined as the entire signal detected in a tissue by an in vivo imaging technique without the need for correction by a second administration of an identical quantity of a probe or labeled compound along with a large excess of unlabeled, but otherwise chemically identical, compound.

For purposes of in vivo imaging, the type of detection instrument available is a major factor in selecting a given detectable marker. For example, radioactive isotopes and $^{18}F$ or $^{123}I$ are particularly suitable for in vivo imaging in the methods of the invention. The type of instrument used will also guide the selection of a radionuclide or stable isotope. In one aspect, the radionuclide chosen must have a type of decay detectable by a given type of instrument. Moreover, other considerations such as the half-life of the radionuclide are taken into account when selecting a detectable marker for in vivo imaging.

The half-life of a detectable marker should be long enough so that the marker is still detectable at the time of maximum uptake by the target, but short enough so that the subject does not sustain deleterious radiation. The probes of the invention can be detected using gamma imaging in which emitted gamma irradiation of the appropriate wavelength is detected. Conventional methods of gamma imaging include, but are not limited to, SPECT and PET. Preferably, for SPECT detection, the chosen detectable marker will lack a particulate emission, but will produce a large number of photons in a 140-300 keV range. For PET detection, the detectable marker will be a positron-emitting radionuclide such as $^{18}F$, which will annihilate to form two 511 keV gamma rays that can then be detected by a PET camera. A probe can be administered to a subject in whom a disease state is anticipated or suspected, for example, patients clinically diagnosed with a disease state.

In one aspect, compounds or probes of the invention, which are useful for in vivo imaging and quantification are administered to a patient. These compounds or probes are to be used in conjunction with non-invasive techniques such as MRS, MRI, PET, SPECT and combinations thereof. Preferably, a compound of the invention may be labeled with $^{19}F$ or $^{13}C$ to yield a probe for MRS/MRI using general organic chemistry techniques known to the art. March, J., Advanced Organic Chemistry: I Reactions, Mechanisms, and Structure (3rd Ed., 1985); Morrison and Boyd, Organic Chemistry (6th Ed., 1992). The compounds of the invention also may be radiolabeled with $^{18}F$, $^{11}C$, $^{75}Br$ or $^{76}Br$ for PET by techniques well known in the art and described by Fowler, J. and Wolf, A. in Positron Emission Tomography and Autoradiography (Phelps, M., Mazziota, J., and Schelbert, H., eds.) pp. 391-450 (Raven Press, NY 1986). The compounds of the invention also may be radiolabeled with $^{123}I$ for SPECT by any of several techniques known to the art. Kulkarni, Int. J. Rad. Appl. & Inst., (Part B) 18: 647 (1991).

In addition, the compounds of the invention may be labeled with any suitable radioactive iodine isotope such as, but not limited to, $^{131}I$, $^{125}I$ or $^{123}I$. For example, a stable form or derivative of a compound of the invention can be reacted with a halogenating agent containing $^{131}I$, $^{125}I$, $^{123}I$, $^{75}Br$, $^{76}Br$ or $^{18}F$. Thus, the stable form or derivative of a compound of the invention and analogs, salts, pharmaceutical compositions, derivatives, prodrugs, racemic mixtures or tautomeric forms thereof are precursors useful for the synthesis of many of the probes of the invention.

The compounds of the invention also may be radiolabeled with known metal detectable markers such as Technetium-99m ($^{99m}$Tc). Modification of the substituents to a compound of the invention in order to introduce ligands that bind such metal ions can be effected without undue experimentation by one of ordinary skill in the art. The metal radiolabeled compound of the invention can then be used as a probe for in vivo imaging. Preparing probes comprising a detectable marker such as, for example, $^{99m}$Tc is well known within the art. Zhuang et al., *Nuclear Medicine & Biology*, 26(2): 217 (1999); Oya et al., *Nuclear Medicine & Biology*, 25(2): 135 (1998); Hom et al., *Nuclear Medicine & Biology*, 24(6): 485 (1997).

In one aspect, a method of the invention may use isotopes detectable by nuclear magnetic resonance (NMR) spectroscopy for purposes of in vivo imaging and spectroscopy. Elements particularly useful in magnetic resonance spectroscopy include $^3$F, $^{19}$F and $^{13}$C. Suitable detectable markers for preparing a probe of the invention also include beta-emitters, gamma-emitters, positron-emitters and x-ray emitters. Moreover, exemplary detectable markers include $^{131}$I, $^{124}$I, $^{123}$I, $^{18}$F, $^{19}$F $^{11}$C, $^{75}$Br, $^{11}$C, $^{13}$N, $^{15}$O and $^{76}$Br. Suitable stable isotopes for use in MRI or MRS, according to the invention, include $^{19}$F and $^{13}$C. In another aspect, suitable radioisotopes for in vitro quantification in biopsied or post-mortem tissue include $^{125}$I, $^{14}$C and $^3$H. Preferably, a probe of the invention comprises $^{11}$C, $^{124}$I or $^{18}$F for use in PET in vivo imaging, $^{123}$I for use in SPECT imaging, $^{19}$F for MRS/MRI and $^3$H or $^{14}$C for in vitro studies. Nonetheless, any conventional method or detectable markers for visualizing probes can be used in accordance with the invention and may be appreciated by those of ordinary skill in the art.

In one aspect of the invention relating to imaging of biopsied tissues, a method is provided that involves incubating tissues (such as, for example, formalin-fixed tissues) with a solution of a labeled compound or probe of the invention. Preferably, the solution is 5-100% ethanol (with the remainder being water) saturated with a labeled compound or probe of the invention. For example, upon incubation, the compound or probe stains or labels specific receptors in the tissue, which can be detected or visualized by any standard method. Such detection can include, for example, microscopic techniques such as bright-field, fluorescence, laser-confocal and cross-polarization microscopy. Alternatively, a solution comprising 5-20% ethanol (with the remainder being 0.9% saline) may be used for detection or quantitation in non-biopsied tissues.

Preferably, a detectable marker for a probe of the invention is a radiolabel, although other labels such as enzymes, chemiluminescent and immunofluorescent labels are well known to skilled artisans. In one aspect, a detectable marker such as $^{125}$I, $^{14}$C or $^3$H can be used to label a compound of the invention to yield a probe for detection or imaging type applications.

When the compounds of the invention are modified to be used as probes, they may be labeled with suitable radioactive halogen isotopes. Although $^{125}$I isotopes are useful for laboratory testing, they will generally not be useful as a detectable marker for actual diagnostic purposes given the relatively long half-life (60 days) and low gamma-emission (30-65 Kev) of $^{125}$I. The isotope $^{123}$I has a half-life of thirteen hours and a gamma energy of 159 KeV such that probes comprising this detectable marker can be readily used for diagnostic purposes. Other isotopes which may be used for in vivo imaging include $^{131}$I (half-life of 8.3 days). Suitable bromine isotopes for a probe of the invention also include $^{77}$Br, $^{75}$Br and $^{76}$Br.

The compounds and probes of the invention lend themselves easily to formation from materials that could be provided to users in kits. For example, kits for forming the probes can contain, without limitation, a vial containing a physiologically suitable solution of an intermediate of a compound of the invention in a concentration and at a pH suitable for optimal complexing conditions. In one aspect, the user would add to the vial an appropriate quantity of a detectable marker, for example, Na$^{123}$I and an oxidant such as hydrogen peroxide. The resulting probe may then be administered intravenously to a patient for imaging by a means for measuring the gamma rays or photo emissions from the probe.

In another aspect, a method for detecting or quantitating a disease or disease state is provided by the invention. For example, the method comprises administering to a patient an effective amount of a probe of the invention. For example, the method can comprise a patient suffering from or believed to be at risk of suffering from a disease such as those identified herein. The method may also comprise administering to the patient an effective amount of a probe of the invention and, optionally, imaging the probe in vivo. Exemplary can mean for imaging of a probe of the invention in vivo include, without limitation, MRS, MRI, PET, SPECT or combinations thereof.

In one aspect, a pharmaceutical composition comprising a probe can also be prepared easily and simply by a user with a kit. For example, the invention provides a kit comprising as materials therefor a non-labeled compound of the invention. Optionally, the compound can be in a dry condition and, also optionally, one or more inert, pharmaceutically acceptable carriers and/or auxiliary substances may be added thereto. A kit of the invention can also include materials such as a reducing agent and, optionally, a chelator. These materials may also be combined. Moreover, the kit can comprise instructions for carrying out a method that involves reacting the materials with a detectable marker including, without limitation, $^{123}$I, $^{125}$I, $^{124}$I, $^{131}$I, $^{18}$F, $^{19}$F, $^{75}$Br, $^{76}$Br or $^{99m}$Tc. An exemplary $^{99m}$Tc detectable marker can be in the form of a pertechnetate solution that is, optionally, included with a kit of the invention. Similarly, the detectable marker can also be included with the kit. The kit can also include instructions for performing an in vivo imaging protocol with a probe prepared therefrom.

When desired, a probe of the invention or pharmaceutical composition thereof may contain any additive such as pH controlling agents (for example, acids, bases, buffers), stabilizers (for example, ascorbic acid) or isotonizing agents (for example, sodium chloride). It will also be appreciated that the methods of the invention can be performed in conjunction with other in vivo techniques such as, for example, PET or SPECT imaging for evaluating one or more additional characteristics of the subject.

In another aspect, a probe of the invention is introduced into a patient in a detectable quantity and after sufficient time has passed for the compound to become associated with one or more receptors, the probe is detected noninvasively inside the patient. Alternatively, a probe of the invention is introduced into a patient, sufficient time is allowed for the probe to become associated with one or more receptors, and then a sample of tissue from the patient is removed and the probe in the tissue is detected apart from the patient. A tissue sample can also be removed from a patient and a probe introduced to the tissue sample. After a sufficient amount of time has passed, the probe is detected by a suitable imaging modality.

The administration of a probe to a patient can be by a general or local administration route. For example, the probe may be administered to the patient such that it is delivered throughout the body. Alternatively, the probe can be administered to a specific organ or tissue of interest.

A tissue can be part of a patient's body. Examples of tissues include the brain, heart, liver, blood vessels and arteries. A detectable or imaging effective quantity is a quantity of a probe or labeled compound of the invention necessary to be detected by the detection method chosen. For example, a detectable quantity can be an administered amount sufficient to enable detection of binding of the probe to one or more receptors. The amount of a probe to be introduced into a patient in order to provide for detection can readily be determined by those skilled in the art. For example, increasing amounts of the probe can be given to a patient until the probe is detected by the detection method of choice. A detectable marker is introduced to the compounds of the invention to provide for a probe that can be detected by suitable imaging modalities.

Those skilled in the art are also familiar with determining the amount of time sufficient for a compound or probe to become associated with one or more receptors. The amount of time necessary can easily be determined by introducing a detectable amount of a probe of the invention into a patient and then detecting the probe at various times after administration.

The term "associated" can mean a chemical interaction between the probe and one or more receptors. Examples of associations include covalent bonds, ionic bonds, hydrophilic-hydrophilic interactions, hydrophobic-hydrophobic interactions and complexes.

Those skilled in the art are familiar with the various ways to detect labeled compounds or probes. For example, MRI, PET or SPECT can be used to detect probes of the invention. The label that is introduced to a compound of the invention to yield a probe can depend on the detection method desired. As indicated, if PET is selected as a detection method, the probe must possess a positron-emitting atom such as $^{11}$C. or $^{18}$F.

In one aspect, the probe should also have sufficient radioactivity and radioactivity concentration to assure reliable diagnosis. Imaging can also be carried out quantitatively. In one aspect, probes for imaging include a radioisotope such as $^{123}$I, $^{125}$I, $^{124}$I, $^{131}$I, $^{18}$F, $^{75}$Br or $^{76}$Br.

In one aspect, agents such as gold nanorods, rhenium tricarbonyl and iron or gadolinium nanoparticles can be used as or comprise exemplary detectable marker substituents to any position of a compound or probe thereof of the invention. These substituents can also be substituents to any of the exemplary groups disclosed herein such as, for example, aryl, heteroaryl, fused aryl, —CO-aryl, CO-fused aryl, —CO-heteroaryl, —CO-fused heteroaryl, biaryl, CO-biaryl, ether-linked aryls, ether-linked heteroaryls, amine-linked aryls, amine-linked heteroaryls, aminoalkoxy arene hybrid, detectable marker, or peptidyl hybrid.

Exemplary compounds, which can, for example, be used as receptor (e.g., androgen receptor or androgen-like receptor) targeted MRI contrast probes, and exemplary syntheses thereof include

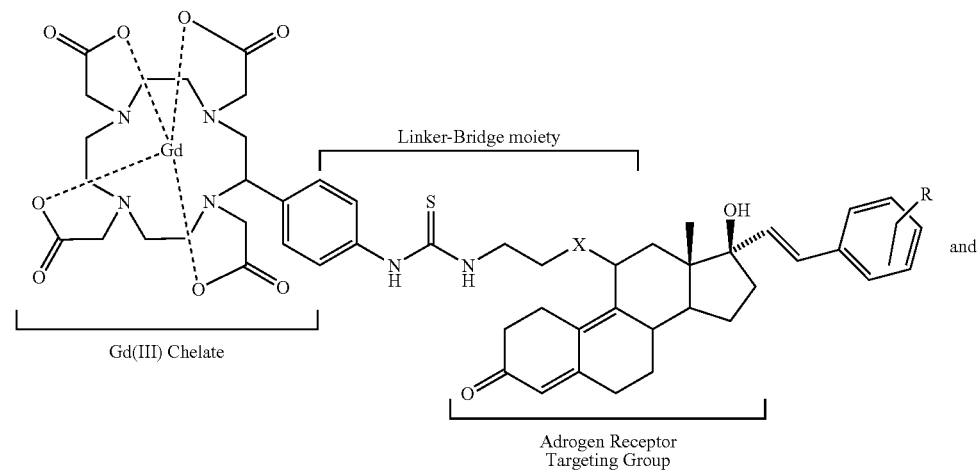

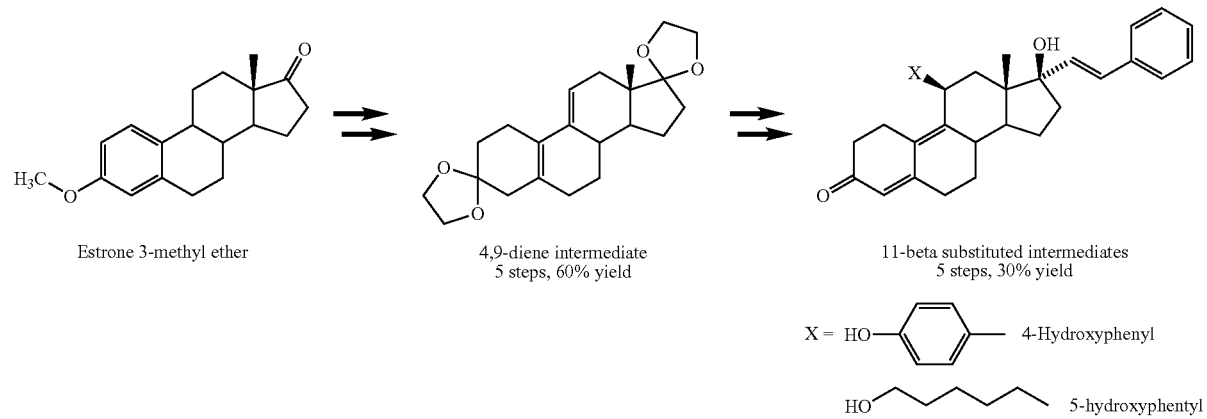

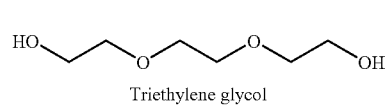

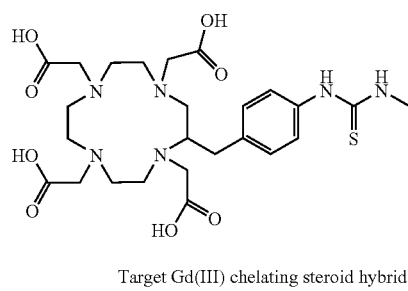

Similar strategies to that above for compounds or probes of the invention and their synthesis will be appreciated by those of ordinary skill in the art for a variety of other imaging modalities in addition to MRI. For example, different groups can be used to yield gold nanoparticles, near IR (NIR) fluorophores or fluorescent fluorophores.

In one aspect, the invention provides a method for in vivo imaging comprising administering to a subject an effective amount of a compound or probe. Preferably, the method can comprise administering a compound or probe of the invention comprising a detectable marker to a subject orally, rectally, parenterally, intravenously, intramuscularly, subcutaneously, intracisternally, intravaginally, intraperitoneally, intravesically, locally or via powders, ointments, drops or as a buccal or nasal spray. The method also comprises detecting the compound or probe. Preferably, the detectable marker can comprise $^{18}F$, $^{11}I$, $^{75}Br$, $^{76}Br$, $^{77}Br$, $^{123}I$, $^{124}I$, $^{131}I$, $^{19}F$, $^{20}F$ $^{15}O$ or $^{99m}Tc$.

For example, the compound or probe can be detected in vivo with conventional or emerging imaging modalities. Conventional imaging modalities include, without limitation, PET, SPECT, planar scintillation imaging or combinations thereof. An exemplary imaging modality can be capable of locating, diagnosing, identifying, evaluating, detecting or quantitating a compound or probe of the invention comprising a detectable marker in vivo.

A method for in vivo imaging can also comprise detecting radioactivity of a compound or probe of the invention comprising a detectable marker. Preferably, the radioactivity of a compound or probe can be measured in vivo. Without limitation, the radioactivity of a compound or probe of the invention comprising a detectable marker can be measured qualitatively or quantitatively. In one aspect, a compound or probe of a method of the invention can be associated with at least one receptor in vivo. For example, a method for in vivo imaging can comprise administering to a subject an effective amount of a compound or probe of the invention comprising a detectable marker. The method can also comprise allowing a sufficient time for the compound or probe to be associated with at least one receptor and then detecting the compound or probe such as with conventional or emerging imaging modalities.

Furthermore, a method for in vivo imaging can comprise administering to a subject an effective amount of a compound or probe of the invention comprising a detectable marker and imaging the subject. In one aspect, the subject can be imaged to detect a distribution of at least one receptor. For example, the distribution of receptors can be within the tissues of the subject. Preferably, a method for in vivo imaging can comprise administering to a subject suffering from or believed to be at risk of suffering from a disorder an effective amount of a compound or probe of the invention comprising a detectable marker. Without limitation, the method can also comprise imaging the subject to obtain data, which may optionally be analyzed to locate, diagnose, identify, evaluate, detect or quantitate the disorder. For example, the disorder can be an estrogen or androgen mediated disorder. The compound or probe can be imaged in vivo with conventional or emerging imaging modalities including PET, SPECT, planar scintillation imaging or combinations thereof.

The data obtained from imaging during a method of the invention can be stored or analyzed by conventional protocols, means, devices, apparatuses or systems known to those of ordinary skill in the art. The invention also provides a method for tissue imaging. In one aspect, the method includes contacting a tissue comprising at least one receptor with the compound or probe of the invention comprising a detectable marker. For example, the at least one receptor can be an estrogen or androgen receptor. Moreover, the method comprises detecting the compound or probe, which can be performed in vitro or in vivo. Preferably, the tissue of a method of the invention can comprise tissues rich in estrogen or androgen receptors. Such tissues can be obtained from the subject by conventional techniques known to those of ordinary skill in the art.

In one aspect, a method for in vivo imaging can comprise administering to a subject suffering from or believed to be at risk of suffering from a disorder an effective amount of a compound or probe of the invention comprising a detectable marker and imaging the subject. The method can also comprise administering to the subject in need thereof a therapeutic agent. Without limitation, the therapeutic agent can be a conventional or emerging agent for treating the disorder or comprise a compound of the invention. Subsequently, the method can comprise administering to the subject an effective amount of the compound or probe comprising a detectable marker and imaging the subject. The method can then provide for a comparison of the extent of the disorder in the subject before and after administering the therapeutic agent. For example, comparing the extent of the disorder in a method of the invention can be performed qualitatively or quantitatively. An exemplary comparison can also be performed by conventional protocols, means, devices, apparatuses or systems known to those of ordinary skill in the art.

The invention also provides a method of assessing, evaluating or determining whether a conventional or emerging therapeutic agent for estrogen or androgen mediated disorders can be selective for at least one receptor. For example, the method can be used to determine at which dosage concentration the agent should be administered to a subject in order to treat the disorder. Exemplary disorders or disease states include, but are not limited to, osteoporosis, endometriosis, breast cancer, benign breast cancer, uterine cancer, ovarian cancer, polycystic ovarian disease, prostate cancer, benign prostatic hyperplasia (BPH), cardiac diseases, coronary artery disease, acne, seborrhea, alopecia, hirsutism, male pattern baldness, and infertility.

In one aspect, the method comprises administering an effective amount of a compound or probe of the invention comprising a detectable marker to a subject not suffering from or believed to be at risk of suffering from a disorder and imaging the subject. Subsequently, the conventional or emerging agent can be administered to the subject at a first dosage concentration. The subject can then be imaged using a compound or probe of the invention comprising a detectable marker. The method also comprises administering the conventional or emerging agent to the subject at a second dosage concentration, followed by imaging the subject with the compound or probe.

EXAMPLES

The following examples are presented to illustrate the advantages of the present invention and to assist one of ordinary skill in making and using the same. These examples are not intended in any way to otherwise limit the scope of the disclosure.

Preferred antiestrogens/antiandrogens for the prevention or treatment of its corresponding hormone-related disorder acting to inhibit estrogen/androgen action may be prepared accordingly as follows:

Example I

Synthesis and evaluation of steroidal antiestrogens at the 17α-Position of Estradiol Solid Phase Synthesis of 17α-substituted Phenylvinyl Estradiols:
Materials Reagents and solvents were obtained from commercial sources (Aldrich and Sigma) and were used without further purification. Wang resins and carboxylated polystyrene resins were obtained from Novabiochem. The loading capacities of the resins, 0.75 mmol $g^{-1}$ for the Wang resin and 2.47 mmol $g^{-1}$ for the polystyrene resin, were determined by the manufacturer.

General Methods

A specially designed flask which had a glass frit, through which the reaction mixture could be filtered by applying pressure, was used for the solid phase synthesis. Purifications for the intermediates were done by rinsing resins three times with the following solvents: $CH_2Cl_2$, THF, DMF, MeOH, $CH_2Cl_2$. The cleaved products were purified via silica gel column chromatography using the appropriate solvents and were characterized by melting point, NMR, IR and electrical analysis. Melting points were determined in open capillary on an Electrothermal Melting Point Apparatus and were uncorrected. IR spectra were recorded on a Perkin-Elmer Model 1600 FT-IR spectrometer. $^1H$ and $^{13}C$ NMR spectra were obtained with a Varian XL-300 NMR spectrometer at 300 MHz in $CDCl_3$, acetone-$d_6$, or DMSO-$d_6$ as a solvent. Elemental analyses were performed by Atlantic Microlab, Inc. (Norcross, Ga.). On-resin reaction monitoring methods, color tests and FT-IR methods were also used. Bromocresol green (0.5% in ethanol, pH=8) was used to assay for free carboxylic acids. The color of the stock solution was dark blue and changed to yellow in the presence of free carboxy groups. Antimony (III) chloride solution (25% in $CCl_4$) was also used to determine whether the steroid (17α-ethynyl estradiol) was coupled to the resin and a positive test result for the presence of estradiol was indicated by the color purple (Carr, 1926; Blatz, 1972; Jork, 1990). In addition, a spectroscopic method (FT-IR) was facilitated to detect chromophore change by reaction.

Preparation of the Carboxylated Resin (Method A). The Wang resins (1 g, 0.75 mmol) were swelled in the $CH_2Cl_2$ overnight and rinsed twice with THF, $CH_3OH$, $CH_2Cl_2$ and acetone. Acetone (5 mL) was added to the swelled resins. To the slurry was added 1 mL of Jones reagent (Bowden, 1946) in a dropwise manner. The mixture was allowed to stand at room temperature for 24 h. The resin mixture was rinsed twice with water-acetone (1:1), $CH_3OH$, DMF, DMSO and $CH_2Cl_2$ and dried in vacuo. The loading capacity after the carboxylation reaction was 0.4-0.6 mmol $g^{-1}$, which was determined with the coupling of 17α-ethynyl estradiol to the resin. The aliquot of the resins was characterized by FT-IR. FT-IR (KBr) v: 3000-3500 (OH, broad), 1690 (C=O, broad), 1603, 1492, 1452 (aromatic ring), 1279 (C—O).

(Method B). The carboxylation of a polystyrene resin was accomplished using the method described by Farrall et al. (Farrall, 1976). FT-IR (KBr) v: 3420 (OH, broad), 1630 (C=O, broad), 1200-1400 (C—O, broad). Loading capacity: 1.5-1.9 mmol Coupling 17α-ethynyl estradiol to the Resins The carboxylated Wang resin (2.3 g) or polystyrene resin (2.5 g) was placed in the reactor equipped with a magnetic stirrer. The resin was swelled in the $CH_2Cl_2$ for 5 h and washed sequentially with THF, DMF, $CH_3OH$, THF and $CH_2CL_2$. To the resin was added 0.23 g (1.1 mmol) of dicyclohexylcarbodiimide (DDC) and 5 ml of $CH_2CL_2$ and the mixture was mildly stirred for 10 min. To the slurry was added 0.75 g (2.6 mmol) of 17α-ethynyl estradiol dissolved in 10 ml of $CH_2CL_2$-DMF (9:1) solvent and a catalytic amount of 4-dimethylaminopyridine (DMAP). The reaction mixture was stirred for 5 min and then allowed to stand at room temperature for 24 h. The resin was washed three times with $CH_2CL_2$ $CH_3OH$, IPA (60° C.), THF and DMF (60° C.) (Morales, 1998). The rinsed resin was dried under vacuum for 5 h. The actual loading of the resin was determined by quantitative measurement of the material by cleavage from known weight of resin using 5 N—NaOH in CH$_3$OH-dioxane (1:3). The resin-bound steroids were characterized by FT-IR and the cleaved compounds by 1H and $^{13}$C NMR before proceeding to the next step. The loading capacity of each resin was shown in Method A and B; FT-IR (KBr) v; 3437 (17β-OH), 3301 (17α-C≡C—H), 1735 (C=O), 1607, 1493, 1452 (aromatic ring), 1216(C—O).

Hydrostannylation (Method A). The 17α-ethynyl estradiol coupled to the resin (0.49 g, 0.57 mmol g$^{-1}$) was placed in a dry 25 mL reaction flask equipped with a reflux condenser and a magnetic stirrer and was swelled in THF for 1 h. To the slurry in the dry THF were added treated triethylborane (0.7 mL) and tributyltin hydride (1 mL) (Nozaki, 1989). The mixture was allowed to stand at 60-70° C. for 48 h under a nitrogen atmosphere. The reaction mixture was washed three times each with CH$_2$Cl$_2$, CH$_3$OH, DMF, CH$_2$Cl$_2$ and ethyl acetate and the resultant resin was dried in vacuo. An aliquot of the resins was cleaved with 5 N NaOH in CH$_3$OH—CH$_2$Cl$_2$ (1:2) to afford a mixture of E- and Z-isomers. The mixture was separated by chromatography on the silica gel to give a 23% (0.13 mmol g$^{-1}$) yield of products, consisting of 21% (0.12 mmol g$^{-1}$) of the E-isomer and 2% (0.01 mmol g$^{-1}$) of the Z-isomer. R$_f$(Z-isomer)=0.58 (hexane-ethyl acetate, 4:1); R$_f$(E-isomer)=0.44 (hexane-ethyl acetate, 4:1); Amorphous; $^1$H NMR (CDCl$_3$, 300 MHz, δ), 0.88 (s, 3H, C$_{18}$-methyl-H), 1.2-2.4 (m, steroid envelope and tributylstannyl-H), 2.7-2.9 (m, 2H, C$_6$—H), 6.06 (d, 1H, J=19.4 Hz, C$_{21}$ vinyl-H), 6.22 (d, 1H, J=19.4 Hz, C$_{20}$ vinyl-H), 6.79 (d, 1H, J=2.4 Hz, C$_4$—H), 6.84 (dd, 1H, J=2.6, 8.4 Hz, C$_2$—H), 7.28 (d, 1H, J=8.8 Hz, C$_1$—H); $^{13}$C NMR (CDCl$_3$), 9.6 (C$_{22}$, 4C), 13.7 (C$_{24}$, 4C), 14.2 (C$_{18}$), 23.4 (C$_{15}$), 26.4 (C$_{11}$), 27.3 (C$_{25}$, 4C), 27.4 (C$_7$), 29.2 (C$_{23}$, 4C), 29.6 (C$_6$), 32.4 (C$_{12}$), 35.9 (C$_{16}$), 39.4 (C$_8$), 43.8 (C$_9$), 46.7 (C$_{13}$), 49.0 (C$_{14}$), 85.6 (C$_{17}$), 112.6 (C$_2$), 115.2 (C$_4$), 124.6 (C$_{21}$), 126.5 (C$_1$), 132.7 (C$_{10}$), 138.3 (C$_5$), 152.4 (C$_{20}$), 153.3 (C$_3$), FT-IR (KBr) v: 3445 (17β-OH, broad, 1719 (C=O), 1653 (C=C), 1607, 1493, 1451 (aromatic ring), 1217 (C—O).

(Method B). The 17α-ethynyl estradiol (3 g, 10 mmol) was dissolved in THF and treated with triethylborane (2 mL, 17 mmol) and tributyltin hydride (3 g, 11 mmol). The mixture was stirred with a magnetic stirrer at 60° C. for 16 h. The crude mixture (7.73 g) was evaporated to dryness, redissolved in the CH$_2$Cl$_2$, and transferred to the swelled resin (5 g) in CH$_2$Cl$_2$ in the presence of DCC. A catalytic amount of DMAP was added to the mixture, which was allowed to stand for 24 h. The resultant functionalized resin was treated as previously described. The total loading for both E- and Z-isomers was 0.59 mmol g–1 with 0.56 mmol g$^{-1}$ of E-isomer and 0.03 mmol g$^{-1}$ of Z-isomer, however, by the dry weight difference between pre- and post-reaction, the loading for both E- and Z-isomers was 1.55 mmol g$^{-1}$.

Electrophilic Destannylation on the Resin

The Stille reaction was used to couple the anchored E- and Z-stannylvinyl estradiol to aryl halides. The resin was added to the reaction flask, swelled in the CH$_2$Cl$_2$, and subsequently treated with 10 mL of anhydrous toluene. To the resultant slurry was added a 3-4 fold excess of the functionalized aryl halide, 1-2 crystals of 3.5-di-t-butyl-4-hydroxytoulene (BHT), and Pd(PPh$_3$)$_4$ (Bowden, 1946; Farrall, 1976). The reaction was allowed to proceed at 90-100° C. for 24 h. After cooling, the resin was washed as previously described, dried in vacuo and weighed.

Cleavage

The resin was swelled in CH$_2$Cl$_2$ (10 mL) containing 3 mL of 5 N—NaOH in CH$_3$OH-Dioxane (1:3) and stirred for 1 h. This cleavage step was repeated three times. Most of the product was collected from the first attempt, a small amount by second hydrolysis, and almost none from the third trial. The fractions were combined, evaporated to dryness, and partitioned between ethyl acetate and water. Acetic acid (1 mL, 5%) was added. The organic phase was washed with 10% aqueous NaHCO$_3$ to remove the residual acetic acid, dried over MgSO$_4$, filtered and evaporated to dryness. The crude product was purified by silica gel column chromatography or by recrystallization from the appropriate solvent.

17α-20E-21-(2-Trifluoromethylphenyl)-19-norpregna-1,3,5 (10),20-tetraene-3,17β-diol (17α-E-(2-trifluoromethylphenyl)-vinyl estradiol) (4a). Yield=38%; R$_f$=0.19 (hexane-ethyl acetate, 4:1); mp 224-225° C.; $^1$H NMR (300 MHz, Acetone-d$_6$, δ) 1.02 (s, 3H, C$_{18}$ methyl-H), 1.2-2.4 (m, steroid envelope), 2.7-2.9 (m, 2H, C$_6$—H), 3.98 (s, 1H, 17β hydroxyl-H), 6.53 (d, 1H, J=2.3 Hz, C$_4$—H), 6.58 (dd, 1H, J=2.6, 8.5 Hz, C$_2$—H), 6.64 (d, 1H, J=15.7 Hz, C$_{20}$ vinyl-H), 7.0 (dd, 1H, J=2.5, 15.8 Hz, C$_{21}$ vinyl-H), 7.07 (d, 1H, J=8.7 Hz, C$_1$—H), 7.42 (t, 1H, J=7.8 Hz, C$_{26}$—H), 7.60 (t, 1H, J=7.3 Hz, C$_{25}$—H), 7.69 (d, 1H, J=7.8 Hz, C$_{27}$—H), 7.81 (d, 1H, J=8.3 Hz, C$_{24}$—H), 7.98 (S, C$_3$ hydroxy-H); $^{13}$C NMR (75.4 MHz, Acetone-d$_6$, δ) 14.7 (C$_{18}$), 24.1 (C$_{15}$) 27.2 (C$_{11}$), 28.3 (C$_7$), (C$_6$), 33.4 (C$_{12}$), 37.5 (C$_{16}$), 40.7 (C$_8$), 44.6 (C$_9$), 48.4 (C$_{13}$), 50.0 (C$_{14}$), 84.3 (C$_{17}$), 113.5 (C$_2$), 115.9 (C$_4$), 123.4 (C$_{21}$), 125.6 (q, J=273.2 Hz, C$_{28}$:CF$_3$), 126.4 (q, J=5.8 Hz, C$_{24}$), 127.0 (C$_1$), 127.4 (q, J=29.4 Hz, C$_{23}$), 127.8 (C$_{26}$), 128.6 (C$_{27}$), 132.0 (C$_{25}$), 133.2 (C$_{10}$), 137.9 (C$_{22}$), 139.1 (C$_5$), 142.4 (C$_{20}$), 155.9 (C$_3$); Anal. Calcd for C$_{27}$H$_{29}$O$_2$F$_3$: C, 73.30; H, 6.56. Found: C, 73.04; H, 6.68.

17α-20E-21-(3-Trifluoromethylphenyl)-19-norpregna-1,3,5 (10),20-tetraene-3,17β-diol (17α-E-(3-trifluoro methyl phenyl)-vinyl estradiol) (5a). Yield=33%; R$_f$ (E-isomer)= 0.19 (hexane-ethyl acetate, 4:1); mp 244-246° C.; $^1$H NMR (300 MHz, Acetone-d$_6$, δ), 1.01 (s, 3H, C$_{18}$-methyl), 1.2-2.4 (m, steroid envelope), 2.7-2.9 (m, 2H, C$_6$—H), 3.98 (s, 1H, 17βhydroxyl-H), 6.53 (d, 1H, J=2.6 Hz, C$_4$—H), 6.58 (dd, 1H, J=2.6, 8.3 Hz, C$_2$—H), 6.74 (d, 1H, J=16 Hz, C$_{21}$ vinyl-H), 6.84 (d, 1H, J=16 Hz, C$_{20}$ vinyl-H), 7.06 (d, 1H, J=8.3 Hz, C$_1$—H), 7.54-7.56 (m, 2H, C$_{25}$, C$_{27}$—H), 7.75-7.79 (m, 2H, C$_{23}$, C$_{26}$—H), 7.93 (s, C$_3$-hydroxy-H); $^{13}$C NMR (75.4 MHz, Acetone-d$_6$, δ), 14.7 (C$_{18}$), 24.1 (C$_{15}$), 27.3 (C$_{11}$), 28.3 (C$_7$), (C$_6$), 33.5 (C$_{12}$), 37.5 (C$_{16}$), 40.7 (C$_8$), 44.6 (C$_9$), 48.4 (C$_{13}$), 50.1 (C$_{14}$), 84.2 (C$_{17}$), 113.5 (C$_2$), 115.9 (C$_4$), 123.6 (q, J=5.6 Hz, C$_{25}$), 124.1 (q, J=3.7 Hz, C$_{23}$), 125.4 (q, J=271 Hz, C$_{28}$:CF$_3$), 126.0 (C$_{26}$), 127.0 (C$_1$), 130.2 (C$_{21}$), 130.7 (C$_{27}$), 131.2 (q, J=32 Hz, C$_{24}$), 132.0 (C$_{10}$), 138.4 (C$_5$), 139.7 (C$_{20}$), 139.9 (C$_{22}$), 155.9 (C$_3$); Anal. Calcd for C$_{27}$H$_{29}$O$_2$F$_3$: C, 73.30; H, 6.56. Found: C, 73.42; H, 6.68.

17α-20E-21-(4-Trifluoromethylphenyl)-19-norpregna-1,3,5 (10),20-tetraene-3,17β-diol (17α-E-(4-trifluoro methylphenyl)-vinyl estradiol) (6a). Yield=49%; R$_f$=0.15 (hexane-ethyl acetate, 4:1); mp 215-217° C.; $^1$H NMR (Acetone-d$_6$, 300 MHz, δ), 1.02 (s, 3H, C$_{18}$ methyl-H), 1.2-2.4 (m, steroid envelope), 2.7-2.9 (m, 2H, C$_6$—H), 3.90 (s, 1H, 17βhydroxyl-H), 6.53 (d, 1H, J=2.6 Hz, C$_4$—H), 6.58 (dd, 1H, J=2.6, 8.4 Hz, C$_2$—H), 6.73 (d, 1H, J=16 Hz, C$_{21}$ vinyl-H), 6.85 (d, 1H, J=16 Hz, C$_{20}$ vinyl-H, 7.07 (d, 1H, J=8.3 Hz, C$_1$—H), 7.64 (d, 2H, J=8.7 Hz, C$_{23}$, C$_{27}$—H), 7.70 (d, 2H, J=8.6 Hz, C$_{24}$, C$_{26}$—H), 8.0 (s, C$_3$-hydroxy-H); $^{13}$C NMR (75.4 MHz, Acetone-d$_6$, δ) 14.7 (C$_{18}$), 24.1 (C$_{15}$), 27.3 (C$_{11}$), 28.3 (C$_7$), (C$_6$), 33.5 (C$_{12}$), 37.6 (C$_{16}$), 40.7 (C$_8$), 44.6 (C$_9$), 48.5 (C$_{13}$), 50.2 (C$_{14}$), 84.2 (C$_{17}$), 113.5 (C$_2$), 115.9 (C$_4$), 125.4 (q, J=270.6 Hz, C$_{28}$:CF$_3$), 126.0 (C$_{21}$), 126.2 (q, J=3.5 Hz, C$_{26}$), 126.2 (q, J=3.5 Hz, $C_{24}$), 127.0 ($C_1$), 127.6 ($C_{23}$, $C_{27}$), 128.9 (q, J=32 Hz, $C_{25}$), 132.0 ($C_{10}$), 138.4 ($C_5$), 140.6 ($C_{20}$), 142.7 $C_{22}$), 155.9 (C3);
Anal. Calcd for $C_{27}H_{29}O_2F_3$: C, 73.30; H, 6.56. Found: C, 73.36; H, 6.79.

17α-20Z-21-(4-Trifluoromethylphenyl)-19-norpregna-1,3,5 (10),20-tetraene-3,17β-diol (17α-Z-(4-trifluoro methylphenyl)-vinyl estradiol) (6b). Yield=17%; $R_f$=0.29 (hexane-ethyl acetate, 4:1); $^1$H NMR (300 MHz, Acetone-$d_6$, δ) 0.97 (s, 3H, $C_{18}$ methyl-H), 1.2-2.4 (m, steroid envelope), 2.7-2.9 (m, 2H, $C_6$—H), 3.89 (s, 1H, 17β hydroxyl-H), 6.12 (d, 1H, J=12.9 Hz, $C_{21}$ vinyl-H), 6.48-6.62 (m, 3H, $C_2$, $C_4$, $C_{20}$ vinyl-H), 7.11 (d, 1H, J=8.1 Hz, $C_1$—H) 7.59 (d, 2H, J=8.4 Hz, $C_{23}$, $C_{27}$—H), 7.80 (d, 2H, J=8.4 Hz, $C_{24}$, $C_{26}$—H), 7.95 (s, $C_3$ hydroxy-H).

17α-20E-21-(2-Methylphenyl)-19-norpregna-1,3,5(10),20-tetraene-3,17β-diol (17α-E-(2-methylphenyl)-vinyl estradiol) (7a). Yield=38%; $R_f$=0.18 (hexane-acetone, 4:1); mp 199-200° C.; $^1$H NMR (Acetone-$d_6$, 300 MHz, δ), 1.01 (s, 3H, $C_{18}$ methyl-H), 1.2-2.4 (steroid envelope), 2.34 (s, 3H, $C_{2-8}$ methyl-H), 2.7-2.9 (m, 2H, $C_6$—H), 3.84 (s, 1H, 17β hydroxyl-H), 6.44 (d, 1H, J=16 Hz, $C_{21}$ vinyl-H), 6.52-6.63 (m, 2H, $C_2$, $C_4$—H), 6.83 (d, 1H, J=16 Hz, $C_{20}$ vinyl-H), 7.07 (d, 1H, J=8.3 Hz, $C_1$—H), 7.10-7.15 (m, 3H, $C_{24}$, $C_{25}$, $C_{26}$—H), 7.48 (d, 1H, J=6.8 Hz, $C_{27}$—H), 7.97 (3, $C_3$ hydroxy-H); $^{13}$C NMR (75.4 MHz, Acetone-$d_6$, δ) 14.7 ($C_{18}$), 19.9 ($C_{28}$, methyl), 24.1 ($C_{15}$), 27.3 ($C_{11}$), 28.3 ($C_7$), ($C_6$), 33.5 ($C_{12}$), 37.5 ($C_{16}$), 40.7 ($C_8$), 44.7 ($C_9$), 48.2 ($C_{13}$), 50.1 ($C_{14}$), 84.2 ($C_{17}$), 113.5 ($C_2$), 115.9 ($C_4$), 125.4 ($C_{26}$), 126.5 ($C_{25}$), 126.9 ($C_{24}$), 127.0 ($C_1$), 127.7 ($C_{21}$), 130.8 ($C_{27}$), 132.0 ($C_{10}$), 135.9 ($C_{20}$), 137.9 ($C_{22}$), 138.4 ($C_5$), 138.8 ($C_{23}$), 155.9 ($C_3$); Anal. Calcd for $C_{27}H_{32}O_2$: C, 83.51; H, 8.25. Found: C, 83.79; H, 8.65.

17α-20E-21-(3-Methylphenyl)-19-nonpregna-1,3,5(10),20-tetraene-3,17β-diol (17α-E-(3-methylphenyl)-vinyl estradiol) (8a). Yield=75%; $R_f$=0.17 (hexane-acetone, 4:1); mp 204-205° C.; $^1$H NMR (300 MHz, Acetone-$d_6$, δ), 1.00 (s, 3H, $C_{18}$ methyl-H), 1.2-2.4 (m, steroid envelope), 2.31 (s, 3H, $C_{28}$ methyl-H), 2.7-2.9 (m, 2H, $C_6$—H), 3.74 (s, 1H, 17βhydroxyl-H), 6.52-6.63 (m, 4H, $C_4$, $C_2$, $C_{21}$ vinyl, $C_{20}$ vinyl-H), 7.03 (d, 1H, J=7.3 Hz, $C_{25}$—H), 7.07 (d, 1H, J=8.7 Hz, $C_1$—H), 7.16-7.31 (m, 3H, J=7.4 Hz, $C_{23}$, $C_{26}$, $C_{27}$—H), 7.93 (s, 1H, $C_3$ hydroxy-H); $^{13}$C NMR (75.4 MHz, Acetone-$d_6$, δ) 14.8 ($C_{18}$), 21.4 ($C_{28}$; methyl), 24.1 ($C_{15}$), 27.3 ($C_{11}$), 28.4 ($C_7$), ($C_6$), 33.5 ($C_{12}$), 37.4 ($C_{16}$), 40.8 ($C_8$), 44.7 ($C_9$), 48.3 ($C_{13}$), 50.2 ($C_{14}$), 84.2 ($C_{17}$), 113.6 ($C_2$), 116.0 ($C_4$), 124.4 ($C_{27}$), 127.0 ($C_1$), 127.7 ($C_{25}$), 127.8 ($C_{26}$), 128.5 ($C_{21}$), 129.2 ($C_{23}$), 132.2 ($C_{10}$), 137.0 ($C_{20}$), 138.4 ($C_5$), 138.7 ($C_{22}$, $C_{24}$), 155.9 ($C_3$); Anal. Calcd for $C_{27}H_{32}O_2$: C, 83.51; H, 8.25. Found: C, 83.23; H, 8.42.

17α-20Z-21-(3-Methylphenyl)-19-norpregna-1,3,5(10),20-tetraene-3,17β-diol (17α-Z-(3-methylphenyl)-vinyl estradiol) (8b). Yield=54% (0.01 g); $R_f$=0.25 (hexane-acetone, 4:1); $^1$H NMR (300 MHz, Acetone-$d_6$, δ) 0.95 (s, 3H, $C_{18}$ methyl-H), 1.2-2.4 (m, steroid envelope), 2.31 (s, 3H, $C_{28}$ methyl-H), 2.7-2.9 (m, 2H, $C_6$—H), 3.27 (s, 1H, 17β hydroxyl-H), 5.96 (d, 1H, J=13.1 Hz, $C_{21}$ vinyl-H), 6.44 (d, 1H, J=13.1 Hz, $C_{20}$ vinyl-H), 6.53 (d, 1H, J=2.6 Hz $C_4$—H), 6.60 (dd, 1H, J=2.6, 8.3 Hz, $C_2$—H), 7.03 (d, 1H, J=7.3 Hz, $C_{25}$—H), 7.11 (d, 1H, J=8.3 Hz, $C_1$—H), 7.17 (t, 1H, J=7.6 Hz, $C_{26}$—H), 7.38-7.43 (m, 2H, $C_{23}$, $C_{27}$—H), 7.95 (s, 1H, $C_3$ hydroxy-H); $^{13}$C NMR (75.4 MHz, Acetone-$d_6$, δ) 14.58 ($C_{18}$), 21.42 ($C_{28}$: methyl). 23.85 ($C_{15}$), 27.40 ($C_{11}$), 28.30 ($C_7$), (C6), 32.97 ($C_{12}$), 38.4 ($C_{16}$), 40.9 ($C_8$), 44.7 ($C_9$), 48.8 ($C_{13}$), 50.1 ($C_{14}$), 84.3 ($C_{17}$), 113.6 ($C_2$), 116.0 ($C_4$), 127.1 ($C_1$), 127.8 ($C_{27}$), 128.1 ($C_{25}$), 128.3 ($C_{26}$), 129.7 ($C_{21}$), 131.4 ($C_{23}$), 132.0 ($C_{10}$), 137.1 ($C_{20}$), 137.6 ($C_{24}$), 138.45 ($C_5$), 138.5 ($C_{22}$), 155.9 ($C_3$); Anal. Calcd for $C_{29}H_{36}O_3$: C, 80.55; H, 8.33. Found: C, 80.00; H, 8.41

17α-20E-21(4-Methoxyphenyl)-19-norpregna-1,3,5, (10),20-tetraene-3,170-diol (17α-E-(4-methoxyphenyl)-vinyl estradiol) (9a). Yield=36%; $R_f$=0.23 (CHCl$_3$—CH$_3$OH, 99:1); $^1$H NMR (300 MHz, Acetone-$d_6$, δ) 0.99 (s, 3H, $C_{18}$ methyl-H), 3.68 (s, 1H, 17β hydroxy-H), 3.78 (s, 3H, $C_{28}$ methoxy-H), 6.46 (d, 1H, J=16.1 Hz, $C_2$, —H), 6.51-6.59 (m, 3H, $C_2$, $C_4$, $C_{20}$—H), 6.88 (d, 2H, J=8.8 Hz, $C_{24}$, $C_{26}$—H); 7.07 (d, 1H, J=8.3 Hz, $C_1$—H); 7.39 (d, 2H, J=8.8 Hz, $C_{23}$, $C_{27}$—H), 7.95 (s, 1H, $C_3$ hydroxy-H); $^{13}$C NMR (75.4 MHz, Acetone-$d_6$, δ) 14.7 ($C_{18}$), 24.1 ($C_{15}$), 27.3 ($C_{11}$), 28.3 ($C_7$), ($C_6$), 33.4 ($C_{12}$), 37.3 ($C_{16}$), 40.7 ($C_8$), 44.7 ($C_9$), 48.2 ($C_{13}$), 50.0 ($C_{14}$), 55.5 ($C_{28}$:methoxy), 84.1 ($C_{17}$), 113.5 ($C_2$), 114.7 ($C_{24}$, $C_{26}$), 115.9 ($C_4$), 127.0 ($C_1$), 127.0 ($C_{21}$), 128.3 ($C_{23}$, $C_{27}$), 131.4 ($C_{22}$), 132.1 ($C_{10}$), 134.9 ($C_{20}$), 138.4 ($C_5$), 155.9 ($C_3$), 159.9 ($C_{25}$)

In the above procedures, the Solid Phase Synthesis methodology was applied using carboxylated resins to generate a series of novel ER-LBD ligands, or estradiol derivatives. The purification steps were simplified and simultaneously produced both the E- and Z-isomers. Yield may be improved by modifications in both the coupling and cleavage steps for a chemically more sensitive Z-isomer.

One of the key elements of the synthetic scheme was the selection of a linker that could be both formed and cleaved under mild conditions. 17α-substituted estradiols were unstable under strongly acidic conditions such as those frequently used to release products from the resins. Therefore the resin of choice was carboxylated polystyrene which could be esterified under neutral conditions and ultimately cleaved with a mild base. Compound 8a was prepared using the carboxylated resin obtained either by oxidation of a Wang resin using Jones reagent (Bowden, 1946) or by carboxylation of a polystyrene resin via lithiation with n-butyl lithium (Farrall, 1976). The reactions for both methods were easily monitored by the appearance of the 1700 cm$^{-1}$ absorption in the FT-IR spectrum. The loading capacity of the carboxylated resins was determined by coupling 17α-ethynyl estradiol onto the resins using DCC in the presence of a catalytic amount of DMAP and measuring its subsequently cleaved estradiol derivatives from the aliquot of the resins. The loading (the loading capacities for the functionalized resins were expressed in mmol g$^{-1}$ and for the following steps were expressed in % or mmol g$^{-1}$) of oxidized Wang resin was 0.4-0.6 mmol g$^{-1}$ and that of carboxylated polystyrene was 1.5-1.9 mmol g$^1$. Once the utility of coupling through the ester linkage using carboxy polystyrene resin was confirmed, the commercially available carboxy polystyrene was used for the remainder of the work. The loading yield of the reaction using the resins with already known loading capacity (2.47 mmol g$^{-1}$) was 82%. The yield was determined by 'cleave and characterize' methods.

Figure 1:
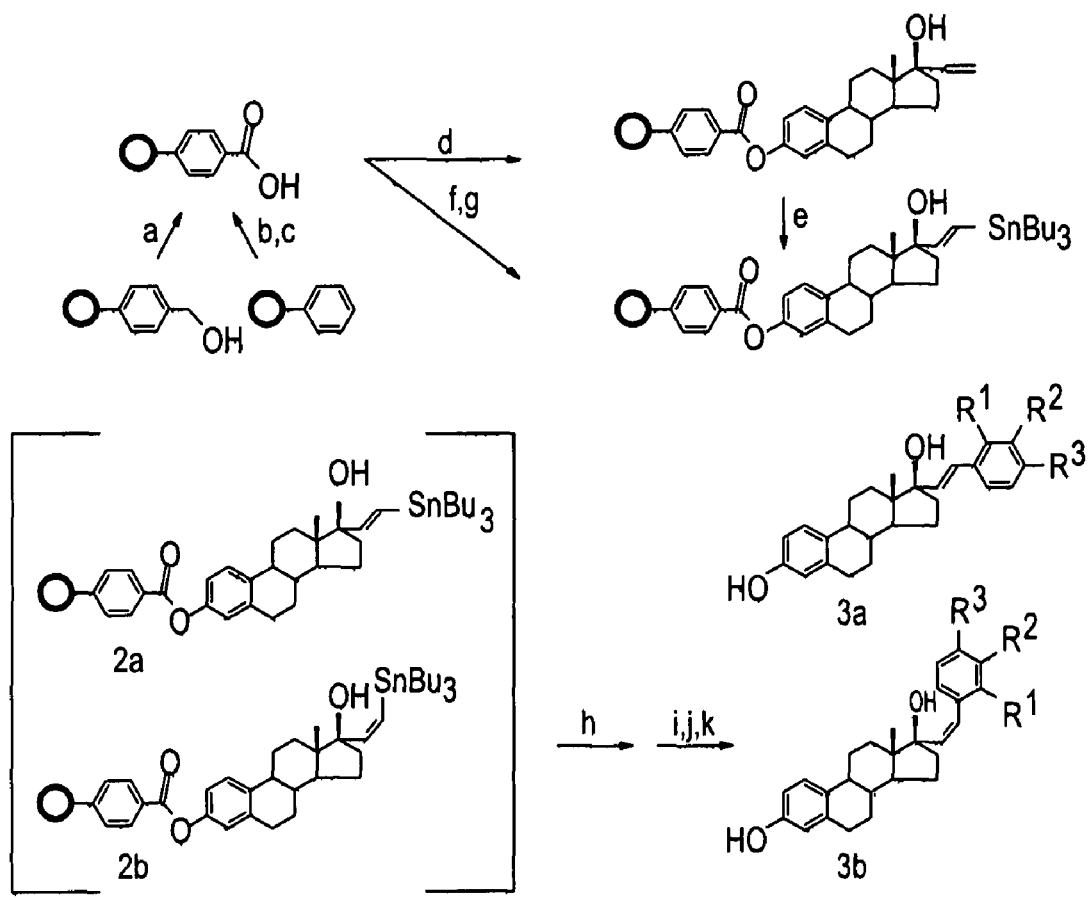
FIG. 1 depicts the synthesis of the estradiol analogs according to the invention by coupling the 3-phenolic group of 17α-ethynyl estradiol to the carboxy polystyrene resin. The reagents and conditions used were as follows.

As shown in FIG. 1, the synthesis of the analogs was initiated by coupling the 3-phenolic group of 17α-ethynyl estradiol to the carboxy polystyrene resin. The steroids on the resins were confirmed by an antimony (III) chloride assay (Carr, 1926; Blatz, 1972; Jork, 1990). Due to the absence of color change with bromocresol green, no free carboxylic acid groups remained on the resin (Gordon, 1972). The appearance of a peak at 3301 cm$^{-1}$ in the IR spectrum, corresponding to the C—H stretch of the ethynyl group, further confirmed that the reaction and a shift of carbonyl absorption to higher frequency (from 1690-1734 cm$^{-1}$) was also observed.

The subsequent hydrostannylation step incorporated either the use of hydrostannylation of bound ethynyl estradiol (Method A) or hydrostannylation of ethynyl estradiol in solution phase synthesis followed by coupling to the resin (Method B). The resin-bound 17α-ethynyl estradiol was hydrostannylated with tributyltin hydride using triethylborane as a radical initiator (Nozaki, 1989) to afford a mixture of the 17α-E/Z-tri-n-butylstannylvinyl estradiol in 20-30% (0.12 mmol g$^{-1}$ of E, 0.01 mmol g$^{-1}$ of Z) loading yields. Varying the reaction conditions, e.g. different solvents, temperatures, or reaction times, did not improve the yields. Therefore, a direct coupling of 17α-E/Z-tri-n-butylstannylvinyl estradiols was used to overcome the low efficiency of this step. 17α-Ethynyl estradiol was hydrostannylated to 60° C. and the crude mixture was directly transferred to the resin slurry in CH$_2$Cl$_2$. The mixture was treated with a 2-3 fold excess of DCC and a catalytic amount of DMAP was added. The loading yield for the coupling reaction was 0.59 mmol g$^{-1}$ with a Z/E ratio=1:20. The low loading yield was due to the use of the acetic acid for the protonation of phenoxide ion after cleavage, subjecting the products to protiodestannylation and reducing the expected loading yield. Because the cleavage after hydrostannylation did not provide a precise loading yield, the dry weight difference between pre- and post-reaction was subsequently used to determine the loading yield. Using the dry weight difference method, the yield for the hydrostannylation reaction was 1.55 mmol g$^{-1}$ for both E- and Z-isomers. Because hydrostannylation on the resin did not afford satisfactory yields, Method B was the method of choice. The ratio of E and Z isomers is a function of the reaction temperature, time and stoichiometric ratio of tributyltin hydride to alkyne. At 60° C. the reaction generated greater than a 20:1 (E/Z) ratio bound to the solid phase. To increase the ratio of the Z-isomer, triethylborane was used as a radical initiator and the reaction was run at low temperature. The proportion of the Z-isomer (Z/E=1:10) was increased. However, the reaction required a longer time and the loading yield for the hydrostannylation was slightly lower than at higher temperature (1.44 mmol g$^{-1}$ by the dry weight difference method) because of more unreacted 17α-ethynyl estradiol in the reaction mixture.

The resin-bound hydrostannnylated estradiol was subjected to the Stille coupling reaction (Stille, 1985) using a variety of substituted aryl halides to generate the target compounds (see Table 2). As shown in FIG. 1, Pd(PPh$_3$)$_4$ was used as the catalyst for the reaction and 3,5-di-t-butyl-4-hydroxytoluene (BHT) was added as a scavenger. The use of Pd(PPh$_3$)$_4$ generated an insoluble by-product that caused coloration of the resin, however, it was easily removed by rinsing it through the built-in filter (50-70 µm). After completion of all the reaction steps, the product was cleaved from the resin by saponification with 5 N NaOH dissolved in CH$_3$OH-Dioxane (1:3).

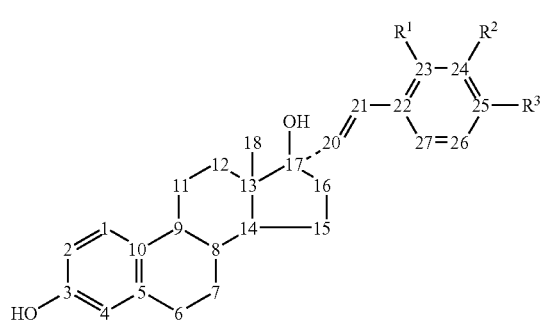

| Compound | R$^1$ (ortho) | R$^2$ (meta) | R$^3$ (para) | Yield (%) |
|---|---|---|---|---|
| 4a: E | CF$_3$ | H | H | 38 |
| 5a: E | H | CF$_3$ | H | 33 |
| 6a: E | H | H | CF$_3$ | 49 |

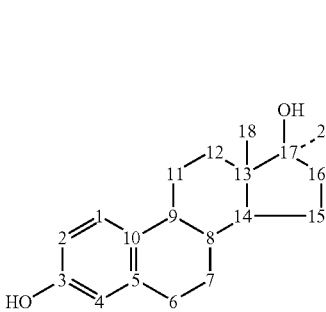

| Compound | R$^1$ (ortho) | R$^2$ (meta) | R$^3$ (para) | Yield (%) |
|---|---|---|---|---|
| 6b: Z | H | H | CF$_3$ | 17 |
| 7a: E | CH$_3$ | H | H | 38 |
| 8a: E | H | CH$_3$ | H | 75 |
| 8b: Z | H | CH$_3$ | H | 54 |
| 9a: E | H | H | OCH$_3$ | 36 |

As shown in Table 2, the unoptimized yields of the Stille reactions on solid phase ranged from 17-75%, comparable to those observed for solution phase synthesis. Compounds 5a (para-trifluoromethylphenyl, E-isomer) and 5b (para-trifluoromethylphenyl, Z-isomer) were isolated from the Stille reaction in a ratio of 98:2. Compounds 7a (meta-methylphenyl, E-isomer)- and 7b (meta-methylphenyl, Z-isomer) were also obtained in a ratio of 96:4. Although the Z-tri-n-butylstannyl vinyl estradiol was initially present on the resin, no Z-isomers of compounds 3a, 4a, 6a, or 8a were isolated from the Stille coupling, instead, 17α-vinyl estradiol, resulting from protiodestannylation was recovered as a side product. Because an excess of reagent was used to drive the reaction to completion, unreacted hydrostannylated 17α-E/Z-(tri-n-butylstannyl)-vinyl estradiol was not detected after the Stille reaction. It is possible that the Z-isomers either isomerized to thermodynamically more stable E-isomers under the conditions required for the Stille reaction or underwent protiodestannylation. As previously observed, the Z-isomer is much more susceptible to protiodestannylation than the E-isomer and the appearance of the side product under either solid phase or solution phase synthesis was approximately the same.

The isolated products were characterized by standard spectroscopic methods (FT-IR, $^1$H and $^{13}$C NMR) and analytical methods. The data were consistent with the proposed structures. Stereochemical assignments for compounds 5a and 5b were based on the C$_{20}$, C$_{21}$ olefinic proton coupling constants for which E=16 Hz and Z-12.9 Hz, respectively. For compounds 7a and 7b, the observed coupling constants were 18.2 Hz of the C$_{20}$ E-vinyl proton and 13.1 Hz of the C$_{20}$ Z-vinyl proton. In $^{13}$C NMR, long range couplings were observed for the compounds 3a-5a and 5b containing the trifluoromethyl group. Coupling with strongly electronegative fluorine was found at the carbon directly attached to the fluorine ($^1$J$_{C-F}$) and one ($^2$J$_{C-F}$) and two carbons distant ($^3$J$_{C-F}$). The carbons appeared as quartets and the coupling constants were approximately $^1$J$_{C-F}$=270 Hz; $^2$J$_{C-F}$=32 Hz; $^3$J$_{C-F}$=3-5 Hz, respectively.

Variability of Ortho, Meta, Para-Substitutions

Ortho, meta, and para (trifluoromethyl)phenylvinyl estradiol isomers were evaluated for estrogen receptor-ligand binding domain (ER-LBD) affinity. The properties of the aryl substituent and its position on the ring (ortho/meta/para) affect receptor binding.

Trifluoromethyl group was introduced onto phenylvinyl estradiol either at the ortho, meta, or para positions. These compounds were examined for their ability to stimulate or inhibit estrogen responses in two assay systems. The initial system evaluated the ability of the ligand to stimulate the proliferation of MCF-7 cells and as the results in FIG. 11 indicate, the ortho-isomer produced a full agonist response comparable to that of estradiol. When the ligand was added to the cells in the presence of 1 nM estradiol, there was neither an enhancement nor a diminution of the proliferative response. The meta- and para-isomers gave substantially different profiles. The meta-isomer demonstrated a weak proliferative effect at doses greater than 1 nM and antagonized the effects of estradiol at the same doses. The para-isomer, however, did not elicit a proliferative response until a 10 nM dose was employed and decreases in the estradiol effects were observed below 1 nM. Therefore, the position of the trifluoromethyl group exerted a significant effect on the efficacy of the ligand.

These trifluoromethyl substituted compounds were also studied with an immature female rat uterotrophic growth assay; the results are shown in FIGS. 12, 13, and 14. In the estrogenic assay, the ortho-isomer produced an effect comparable to estradiol at a 3 nM level and substantial estrogenic effects at 10 and 100 nM. The meta- and para-isomers, however, demonstrated little or no estrogenic effects, even at 10 and 100 nM. Therefore, the agonist responses observed in the in vitro cell proliferation assay were carried over to the intact animal as well. The antiestrogen assay evaluated the ability of the isomers to block the uterotrophic effect induced by 1 nM estradiol. Under these conditions, the ortho isomer produced an enhancement of the estrogenic response at both 10 and 100 nM. The meta-isomer demonstrated no significant effect on the estradiol response at either dose, however, the para-isomer reduced the estrogenic response at the 100 nM level. Therefore, in both estrogen responsive cells and tissues these new ligands are producing differential responses in affinity and efficacy related to the site of trifluoromethyl substitution on the phenyl ring.

Example II

Development of Antiandrogens

The cellular target for antiandrogen therapy, the androgen receptor (AR), is a member of the nuclear receptor superfamily which has been studied extensively over the past decade (Tsai, 1994). Members of this receptor bear a strong structural similarity (homology) and utilize similar signaling pathways to express their biological actions. At the molecular level, the AR, like the other steroid hormone receptors, is composed of discrete domains that are responsible for specific functions. The hormone binding domain (HBD), the sequence of amino acids near the N-terminus of the AR, recognizes and binds testosterone with high affinity but not other hormones or small endogenous molecules (Weatherman, 1999; Simons, 1998). This region of the receptor has been examined using X-ray crystallography to elucidate the amino acid residues responsible for the recognition of specific hormones. The hormone binding domains on the estrogen receptor (ER), progesterone receptor (PgR) and retinoic acid receptor (RAR) provide a common fold for the endogenous hormone, which also strongly suggest the types of conformational changes that occur upon ligand binding (Brzozowski, 1997; Tannenbaum, 1998; Shiau, 1998; Williams, 1998; Renaud, 1995; Klaholz, 1998). The conformational changes, particularly those associated with helix-12, assist in the recruitment of specific coactivator proteins that appear to initiate the action of the general transcription apparatus (Resche-Rigon, 1998; McKenna, 1999; Klinge, 2000).

In accordance with the present invention, the steroidal nucleus is the address component, which directs the molecule to the HBD where, for agonists, the D-ring substituents direct helix-12 into a conformation that exposes the Activation Function-2 (AF-2) or message component. For known ER and PgR antagonists, the steroid nucleus present in most drugs provides the appropriate address. However, the incorporation of an additional functional group interferes with the movement of helix-12, and produces a full or partial antagonist response (message). Most of the antihormones known in the art incorporate that additional functional group at either the 11β- or 7α-position of the steroid (see FIG. 7). The present invention shows that antagonism can be generated through introduction of an appropriate 17α-substituent.

Significant research efforts have focused on the synthesis and evaluation of compounds designed to either mimic or block the effects of the endogenous androgen, testosterone. While many steroidal compounds can mimic testosterone, relatively few were able to block its effects in target tissues and virtually none were effective in treating hormone responsive prostate cancer (Teutsch, 1995). Nonsteroidal agents, however, such as (hydroxy)flutamide, nilutamide, and bicalutamide (Sciarra, 1990; Tucker, 1988, 1990), have demonstrated clinical efficacy for the treatment of prostatic carcinoma, even though their affinity for the AR is relatively low when compared to testosterone (Kokontis, 1999; Battmann, 1998). Recent publications have disclosed another class of nonsteroidal antiandrogens which have potential as clinically useful agents (Hamann, 1998; Edwards, 1999; Higuchi, 1999; Kong, 2000). Analogs of these compounds also demonstrate agonist/antagonist responses at other nuclear receptors (Pooley, 1998; Zhi, 1998, 1999, 2000). Because the non-steroidal antiandrogens do not correspond to any current steroid hormone pharmacophore, it is possible that they may primarily effect only the message region (helix-12) of the AR-HBD. A potent interaction at that site would still compete with agonist ligand binding for the address region, not entirely unlike the situation for the dopamine transporter inhibitors where structurally diverse families of ligands not only inhibit dopamine and cocaine binding but also, by associating with overlapping sites, inhibit the binding of each other. Thus, the present invention combines features from both the steroid nucleus (address component) and the nonsteroidal antagonist pharmacophore (message component) (see FIG. 8).

Synthesis and Evaluation of Steroidal Antiandrogens at the 17α-Position of Testosterone
Synthesis of the Message Components, Characterization, and Conformational Analysis A combination of organotin chemistry and palladium catalyzed coupling reactions is used for the synthesis of the message components (see FIG. 10). The 1-ethynyl-1-aminoperhydroindanes which would incorporate the C- and D-rings of the steroid nucleus is prepared from the corresponding 1-ethynyl-1-acetoxy analogs using a Cu(I)-assisted aminolysis. The ethynyl cycloalkyl alcohols or amines readily undergo hydrostannation to give the corresponding E- and Z-stannylvinyl intermediates which can be coupled with the requisite mono- or di-substituted aryl iodide under Stille coupling conditions (Farina, 1995; Casado, 1998). Three 3'- or 4'-substituted, three 3'-, 4'-disubstituted, and three 3'-, 5'-disubstituted phenyl iodides are used to generate a total of 18 compounds. While there are no obvious choices for the optimal substituents, the structure activity relationships (SAR) for antiandrogens suggest that electron withdrawing groups (e.g., —$NO_2$, $CF_3$) enhance potency. Therefore, these groups are used with one electron releasing group in the first series (Tucker, 1988). Suzuki coupling reaction is used with vinylboronic acid (Suzuki, 1999). The E-vinylboronic acid is accessed directly by hydroboration of the alkyne with catecholborane followed by hydrolysis. The Z-isomer is obtained from the Z-vinylstannane via iododestannylation, followed by coupling with bispinacolatodiboron, and hydrolysis.

For the synthesis of the spirocyclic ether or amine message components, the coupling partner for the Z-vinylstannane (or boronic acid) requires an orthoiodo(bromo)phenol derivative. Halogenation of the commercially available 3'- or 4'-substituted phenol gives the intermediate which is initially protected as the silyl ether. The Z-vinyl arene is made by the standard Stille or Suzuki coupling methods. The conditions developed by Buchwald and Hartwig to effect the intramolecular aryl amine/ether formation may be used (Wolfe, 1998, 1999; Yang, 1999; Hartwig, 1998a,b). Deprotection of the phenol, conversion to the triflate, and coupling with an appropriate Pd catalyst, such as $Pd_2(dba)_3$, and an activating ligand, such as BINAP, will effect the cyclization. The final product is provided by the deprotection of the amine.

Each new compound synthesized is characterized by the standard spectrometric methods—high resolution mass spectrometry (HRMS) and H-1/C-13-nuclear magnetic resonance spectrometry (NMR) to confirm the proposed molecular structures. Solution conformations are determined by using 1D- and 2D-NMR techniques, methods of which are described above. Through use of both conformational analysis and computational methods, more probable solution conformations are identified, which provides information with regard to key structural features and how they influence molecular conformations.

Screening for Androgen Receptor Affinity, Efficacy and Selectivity

Compounds prepared containing the message components may be screened by a bioevaluation protocol already established through a commercially available company (e.g., MDS-Panlabs, located in Bothell, Washington) to determine their AR affinity, efficacy and selectivity. Receptors from rat ventral prostate tissue may be used to determine the IC50 and Ki values. [H-3] mibolerone may be used as the radioligand. Synthesized hydroxyflutamide, nilutamide, bicalutamide and LG 120907 are evaluated as standard AR ligands. Those new compounds that demonstrate AR affinities >10% that of bicalutamide or LG 120907 will be evaluated for their affinities for the other nuclear receptors. Other sources for receptors and their radioligands include ERα-human recombinant from insect St9 cells, [H-3] estradiol, GR-human Jerkat cells, [H-3] dexamethasone, and PgR-bovine, [H-3] R-5020. Compounds that express a significant selectivity for AR (>10:1) are tested for their efficacy in the rat agonism/antagonism model. An in vitro efficacy model for testing the compounds for antagonism is the use of cotransfection and whole cell receptor binding (Hamann, 1998).

Preliminary SARs is determined from the IC50 and Ki data from the screening of the new compounds. E- vs. Z-stereochemistry of the acyclic series of compounds is studied as well as the effects of mono- vs. di-substitution and 3- vs. 4-substitution. The cyclized compounds are compared with the acyclic series to identify particular substituent trends. The QSAR-COMFA module of SYBIL is used to clarify the individual parameters (Gantchev, 1994). The physicochemical parameters developed by Hansch may also be used to evaluate the data (Gantchev, 1994). The most potent ligands are analyzed for the lowest energy conformations using QUANTA-CHARMM/mm3 force fields (Wurtz, 1998) and compared with those from the NMR conformational studies to rationalize the initial SAR. This allows for better determination of which substituents are most effective in contributing to AR affinity, selectivity and antihormonal response. Subsequently, the selected substituents are used for incorporation into the address-message composite.

Synthesis of (Nor)Testosterone Derivatives with the Message Component At 17α-Position 17α-ethynyl-(19nor)testosterone and its dihydroderivative (address component) is used as the starting material. The message components may be obtained from commercially available (or readily synthesized) mono- and disubstituted iodophenols. The same message components as with the estrogen study are used—the nilutamide/bicalutamide family of nonsteroidal antagonists and the more potent Ligand Pharmaceutical antagonists. For the message components analogous to flutamide and bicalutamide, the ethylene group is selected as an isosteric substitution for the amide bond (Luthman, 1996). The method for synthesis of the (nor)testosterone derivatives with the message component at the 17α-position is similar to the steps used for the synthesis of antiestrogens described herein. The antiandrogens of the present invention will include the steroid nucleus (A-D rings) and will provide functionality in the A-ring (3C=O/—OH; 4,5-C=C). In one aspect, these groups are prepared to protect them as ketals, esters or silyl/enol ethers (Hoyte, 1993; van den Bos, 1998).

Synthesis of 17α-E-(2-trifluoromethyl-5[F-18]fluoromethylphenyl) vinyl estradiol, an Exemplary Probe of the Invention

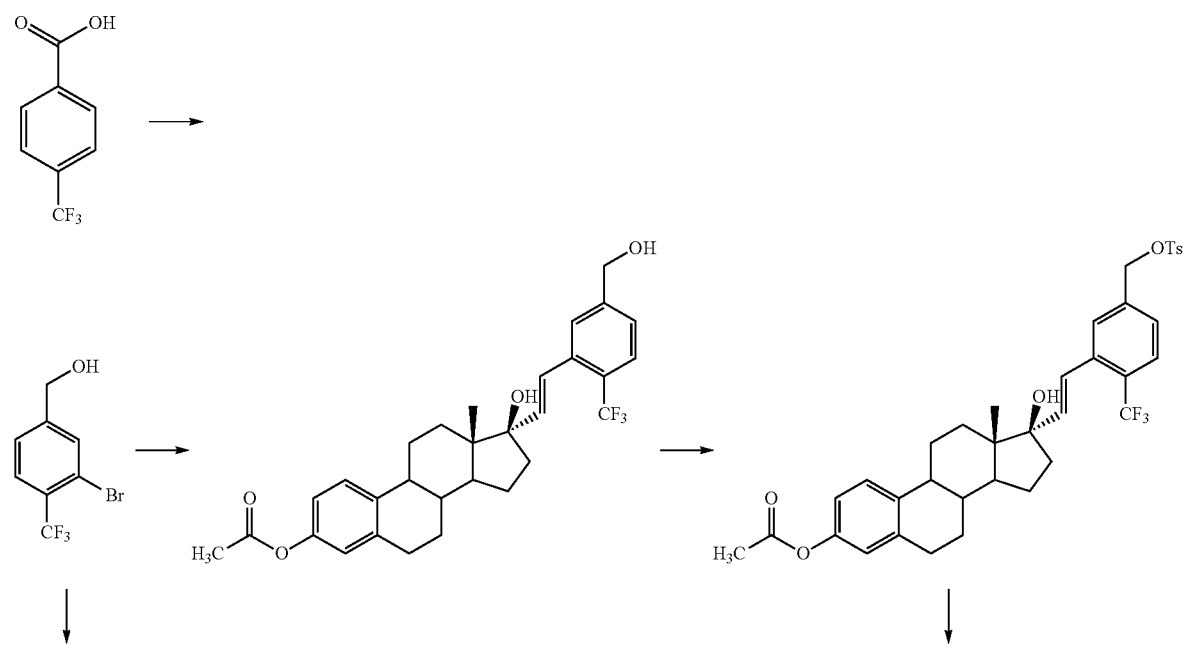

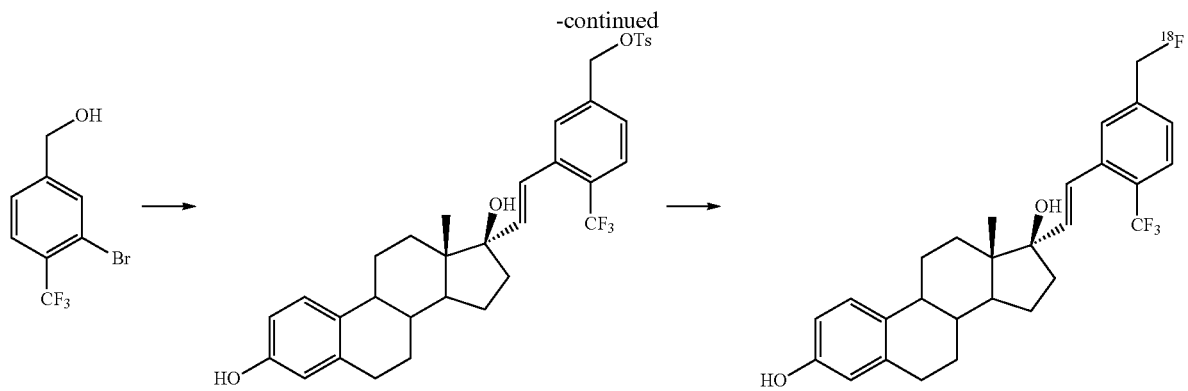

The intermediate, 3-bromo-4-(trifluoromethyl)phenylmethanol is prepared according to the procedure described by Carroll, et al., (J. Med. Chem. 47: pp. 3163-3179, 2004) starting from 4-trifluoromethyl-benzoic acid. The intermediate is then coupled with 17α-E-tri-n-butylstannylvinyl estradiol 3-acetate using our standard conditions, i.e., tetrakis(tri-tert butylphosphine) palladium(0) catalyst, cesium fluoride, toluene, nitrogen atmosphere and heating at 90-100° C. for 2-4 h. The reaction is cooled and the product is isolated by flash chromatography. The resultant product which has the free —CH2OH group on the phenyl ring is then reacted with tosyl chloride and triethylamine in dichloromethane.

Purification by flash chromatography yields the tosyloxy precursor for radiofluorination. Radiofluorination is achieved by nucleophilic displacement of the tosyloxy group with tetrabutylammonium[F-18]fluoride, followed by base hydrolysis of all acyl/tosyl groups and HPLC purification and isolation of the 17α-E-(2-trifluoromethyl-5[F-18]fluoromethylphenyl)vinyl estradiol.

An alternate procedure to the exemplary synthesis described above involves the conversion of 3-bromo-4-(trifluoromethyl)phenylmethanol to the corresponding tosylate derivative initially. Coupling under our standard conditions yields the precursor lacking the 3-acetyl protecting group. Radiofluorination followed by isolation without the deprotection step yields the product.

REFERENCES

Battmann, T, Branche, C, Bouchoux, F, Crede, E, Philibert, D, Goubet, F, Teutsch, G, Gaillard-Kelly, M, Pharmacological profile of RU58642, a potent systemic antiandrogen for the treatment of androgen-dependent disorders. *J. Steroid Biochem. Molec. Biol.* (1998) 64: 103-111;

Beatson G T, On the treatment of inoperable cases of carcinoma of the mamma: suggestions for a new method of treatment with illustrative cases. *Lancet*. (1896) ii: 104-107;

Bhatnagar A S, Miller W R, Pharmacology of inhibitors of estrogen biosynthesis, in "Estrogens and Antiestrogens." *Handbook of Experimental Pharmacology.* 136, Vol. II, Oettel M, Schillinger E, Eds., Springer-Verlag, New York (1999), 223-230;

Blatz, P E., Estrada, A. *Anal. Chem.* (1972) 44: 570-573;

Bowden, K, Heilbron, I M, Jones, E R H, Weedon, BCL, *J. Chem. Soc.* (1946) 39-45;

Boyd, S, On oophorectomy in cancer of the breast. *Br. Med. J.* (1900) ii: 1161-1167;

Brzozowski, A M, Pike, A C W, Dauter, Z, Hubbard, R E, Bonn, T, Engstrom, O, Öhman, L, Greene, G L, Gustafson, J A, Carlquist, M, Molecular basis of agonism and antagonism in the estrogen receptor. *Nature* (1997) 389: 753-758;

Carroll, et al., J. Med. Chem. 47: pp. 3163-3179, 2004;

Carr, F H, Price, E A *Biochem. J.* (1926) 20: 497-501;

Casado, A L, Espinet, P, Mechanism of the Stille reaction, 1. The transmetalation step. Coupling of RI and R2SnBu3 catalyzed by trans-[PdR1L2] (R1=C6C12F3; R2=vinyl, 4-methoxyphenyl; L=AsPh3). *J. Am. Chem. Soc.* (1998) 120: 8978-8985;

Cole M P, Jones C T A, Todd I D H. A new antiestrogenic agent in late breast cancer. An early appraisal of ICI 46,474. *Br J Cancer* 25:270-275 (1971);

Early Breast Cancer Trialists' Collaborative Group. Tamoxifen for early breast cancer: an overview of the randomized trials. *Lancet* 351:1451-1467 (1998);

Edwards, J. P., Higuchi, R. I., Winn, D. T., Pooley, C. L. Fr., Caferro, T. R., Hamann, L. G., Zhi, L., Marschke, K. B., Goldman, M. E., Jones, T. K. Nonsteroidal androgen agonists based on 4-(trifluoromethyl)-2H-pyrano[3,2-g] quinoline. *Bioorg. Med. Chem. Lett*. (1999) 9:1003-1008;

Farina V, Krishnamurthy V, Scott W J. The Stille reaction. *Org Reactions* 50:1-651 (1995);

Farrall, M. J., Frechet J. M. J. *J. Org. Chem*. (1976) 41:3877-3882;

Fowler, J. and Wolf, A. in POSITRON EMISSION TOMOGRAPHY AND AUTORADIOGRAPHY (Phelps, M., Mazziota, J., and Schelbert, H. eds.) 391-450 (Raven Press, NY 1986);

Galbraith, S. M., Duchesne, G. M. Androgens and prostate cancer: Biology, pathology and hormonal therapy. *Eur. J. cancer* (1997) 33: 545-554;

Gantchev, T. G., Ali, H., van Lier, J. E. Quantitative structure-activity relationships/comparative molecular field analysis (QSAR/CoMFA) for receptor-binding properties of halogenated estradiol derivatives. *J. Med. Chem*. (1994) 37:4164-4176;

Gordon, A. J., Ford, R. A. *The Chemist's Companion—A Handbook of Practical Data, Techniques and References*, Wiley: New York, (1972) p 378;

Greenlee, R T et al., (2000) Cancer Statistics 2000, C A, *Cancer J. Clin.,* 50:7-33;

Grese T A, Dodge J A. Selective estrogen receptor modulators (SERMS). *Curr Pharm Design* 4:71-92;

Haas, G. P., Sake W. A. Epidemiology of prostate cancer. *CA-Cancer J. Clin.* (1997) 47:273-287;

Hamann, L. G., Higuchi, R. I., Zhi, L., Edwards, J. P., Wang, X.-N., Marschke, K. B., Kong, J. W., Farmer, L. J., Jones, T. K. Synthesis and biological activity of a novel series of nonsteroidal, peripherally selective androgen receptor antagonists derived from 1,2-dihydrophyridono[5,5-g]quinoline. *J. Med. Chem.* (1998) 41:623-639;

Hartwig, J. F., Transition metal catalyzed synthesis of arylamines and aryl ethers from aryl halides and triflates: Scope and mechanism. *Angew. Chem. Int. Ed.* (1998b) 37:2046-2067;

Hartwig, J. F. Carbon-heteroatom bond-forming reductive eliminations of amines, ethers and sulfides. *Acc. Chem. Res.* (1998a) 31:852-860;

Higuchi, R. I., Edwards, J. P., Caferro, T. R., Ringgenberg, J/D., Kong, J. W., Hamann, L. G., Arienti, K. L., Marschke, K. B., Davis, R. L., Farmer, L. J., Jones, T. K. 4-Alkyl- and 3,4-dialkyl-1,2,3,4-tetrahydro-8-pyridono[5,6-g]quinolines: Potent nonsteroidal androgen receptor agonists. *Bioorg. Med. Chem. Lett.* (1999) 9:1335-1340;

Hom et al., "Technetium 99m-labeled receptor-specific small-molecule radiopharmaceuticals: recent developments and encouraging results" Nuclear Medicine & Biology 24(6):485-98, (1997);

Hoyte, R. B., Brown, T. J., MacLusky, N. J., Hochberg, R. B. 7a-Methyl-17a-(E-2'-[I-125]iodovinyl)-19-nortestosterone: a new radioligand for the detection of the androgen receptor. *Steroids* (1993) 58:13-23;

Jork, H., Funk, W., Fischer, W., Wimmer, H., *Thin-Layer Chromatography, Reagent and Detection Method*, VCH: New York, (1990) Vol. 1a;

Klaholz, B. P., Renaud, J.-P., Mitschler, A., Zusi, C., Chambon, P., Gronemeyer, H., Moras, D. Conformational adaptation of agonist to the human nuclear receptor RARγ. *Nature Struct. Biol.* (1998) 5:199-202;

Klinge, C. M. Estrogen receptor interaction with co-activators and co-repressors. *Steroids* (2000) 65:227-251;

Kokontis, J. M., Liao, S. Molecular action of androgen in the normal and neoplastic prostate. *Vitamins and Hormones* (1999) 55:219-307;

Kong, J. W., Hamann, L. G., Ruppar, D. A., Edwards, J. P., Marschke, K. B., Jones, T. K. Effects of isosteric pyridone replacements in androgen receptor antagonists based on 1,2-dihydro- and 1,2,3,4-tetrahydro-2-2-dimethyl-6-trifluoromethylp8-pyridono[5,6-g]quinoline. *Bioorg. Med. Chem. Lett.* (2000) 10:411-414;

Landis, S. H., Murray, T., Bolden, S., Wingo, P. A. Cancer statistics-1999. *CA-Cancer J. Clin.* (1999) 49:8-31;

Levenson A S, Jordan V C. Selective oestrogen receptor modulation: Molecular pharmacology for the millennium. *Eur J Cancer* 35:1628-1639 (1999);

Luthman K. Hacksell, U. Peptides and peptidomimetics. In "*A textbook of Drug Design and Development, 2$^{nd}$ ed.*" Krogsgaard-Larsen, P., Liljefors, T., Madsen, U., eds. Harwood, Amsterdam (1996) pp. 386-406;

March, J. ADVANCED ORGANIC CHEMISTRY: I REACTIONS, MECHANISMS, AND STRUCTURE (3rd Edition, 1985);

McCammon et al., (1993), *Mol. Cell. Endocrinology*, 91:177-183;

McKenna, N. J., Lanz, R. B., O'Malley, B. W. Nuclear receptor coregulators: Cellular and molecular biology. *Endocr. Rev.* (1999) 20:321-344;

Mettlin, C. Recent developments in the epidemiology of prostate cancer. Eur. *J. Cancer* (1997) 33:340-347;

Morales, G. A., Corbett, J. W., Degrado, W. F. *J. Org. Chem.* (1998) 63:1172-1177;

Nozaki, K., Oshima, K., Utimoto, K. *Tetrahedron* (1989) 45:923-933;

Ornstein, D. K., Dahut, D. L., Liotta, L. A., Emmert-Buck, M. R. Review of AACR meeting: New research approaches in the prevention and cure of prostate cancer, 26 Dec. 1998, Indian Wells, Calif. *Biochem. Biophys. Acta* (1999) 1424: R11-R19;

Kulkarni, Int. J. Rad. Appl. & Inst. (Part B) 18: 647 (1991);

Pooley, C. L. F., Edwards J. P., Goldman, M. E., Wang, M.-W., Marschke, K. B., Crombie, D. L., Jones, T. K. Discovery and preliminary SAR studies of a novel, nonsteroidal progesterone receptor antagonist pharmacophore. *J. Med. Chem.* (1998) 41:3461-3466;

REMINGTON'S PHARMACEUTICAL SCIENCES, 15th Ed. Easton: Mack Publishing Co. pp. 1405-1412 and 1461-1487 (1975) and THE NATIONAL FORMULARY XIV., 14th Ed. Washington: American Pharmaceutical Association (1975);

Renaud, J. P., Rochel, N., Ruff, M., Vivat, V., Chambon, P., Gronemeyer, H., Moras, D. Crystal structure of the RAR-γ ligand binding domain bound to all-trans retinoic acid. *Nature* (1995) 378:681-689;

Resche-Rigon, M., Gronemeyer, H. Therapeutic potential of selective modulators of nuclear receptor action. Curr. Opin. Chem. Biol. (1998) 2: 501-507;

Roach, M., III. Current status of androgen suppression and radiotherapy for patients with prostate cancer, *J. Ster. Biochem. Molec. Biol.* (1999) 69:239-245;

Sciarra, F., Toscano, G., Concolino, G., DiSilverio, F. Antiandrogens: Clinical applications. J. Steroid Biochem. Molec. Biol. (1990) 37:349-362;

Scott, J A et al., (1991) *New Molecular Markers of Prognosis in Breast Cancer*, Raven Press, New York, pp. 179-196;

Shiau A K, Barstad D, Loria P M, Cheng L, Kushner P J, Agard D A, Greene G L. The structural basis of estrogen receptor/coactivator recognition and the antagonism of this interaction by tamoxifen. *Cell* 95:927-937 (1998);

Oya et al., "Small and neutral Tc(v)O BAT, bisaminoethanethiol (N2S2) complexes for developing new brain imaging agents" Nuclear Medicine & Biology 25(2):135-40, (1998);

Simons, S. S. Jr. Structure and function of the steroid and nuclear receptor ligand binding domain. In "*Molecular Biology of Steroid and Nuclear Hormone Receptors*," Freeman, L., ed. Birkhauser, Boston, (1998) pp. 35-104;

Stille, J. K. Pure Appl. Chem. (1985) 57:1771-1780; Suzuki, A. Recent advances in the cross-coupling reactions of organoboron derivatives with organic electrophiles, 1995-1998. *J. Organomet. Chem.* (1999) 576:147-168;

Tannenbaum, D. M., Wang, Y., Williams, S. P., Sigler, P. B. Crystallographic comparison of the estrogen and progesterone receptor's ligand binding domains. *Proc. Nat. Acad. Sci.* (1998) 95: 5998-6003;

Teutsch, G., Nique F., Lemoine, G., Bouchoux, F., Ce're'de, E., Gofflo, D., Philibert, D. General structure-activity correlations of antihormones. *Ann. N.Y. Acad. Sci.* (1995) 761:5-28;

Tsai, M. J., O'Malley, B. W. Molecular mechanisms of action of the steroid/thyroid receptor superfamily members. *Ann. Rev. Biochem.* (1994) 63:451-486;

Tucker, H. Nonsteroidal antiandrogens in the treatment of prostate cancer. *Drugs Future* (1990) 15(3):225-265;

Tucker, H., Crook, J. W., Chesterson, G. J., Nonsteroidal anti-androgens. Synthesis and structure-activity relationships of 3-substituted derivatives of 2-hydroxypropionanilides. *J. Med. Chem.* (1988) 31:954-959;

Van Den Bos, J. C., Rijks, L. J. M., van Doremalen, P. A. P. M., de Bruin, K., Janssen, A. G. M., van Royen, E. A. New iodinated progestins as potential ligands for progesterone receptor imaging in breast cancer. Part 1: Synthesis and in vitro pharmacological characterization. *Nucl. Med. Biol.* (1998) 25:781-789;

Weatherman, R. V., Fletterick, R. J., Scanlon, T. S. Nuclear receptor ligands and ligand binding domains. *Ann. Rev. Biochem.* (1999) 68:559-581;

Williams, S. P., Sigler, P. B. Atomic structure of progesterone complexed with its receptor. *Nature* (1998) 393:392-396;

Wolfe, J. P., Singh, R. A., Yang, B. H., Buchwald, S. L. Highly reactive palladium catalysts for Suzuki coupling reactions. *J. Amer. Chem. Soc.* (1999) 121: 9550-9561;

Wolfe, J. P., Wagaw, S., Marcoux, J. F., Buchwald, S. L. Rational development of practical catalysts for aromatic carbon-nitrogen bond formation. *Acc. Chem. Res.* (1998) 31:805-818;

Wurtz, J. M., Egner, U., Heinrich, N., Moras, Mueller-Fahrnow, A. Three-dimensional models of estrogen receptor ligand binding domain complexes, based on related crystal structures and mutational and structure-activity data. *J. Med. Chem.* (1998) 41:1803-1814;

Yang, B. H., Buchwald, S. L. Palladium-catalyzed amination of aryl halides and sulfonates. *J. Organomet. Chem.* (1999) 576:125-146;

Zhi, L., Tegley, C. M., Pio, B., West, S. J., Marschke, K. B., Mais, D. E., Jones, T. K. Nonsteroidal progesterone antagonists based on the 6-thiophenehydroquinolines. *Bioorg. Med. Chem. Lett.* (2000) 10:415-418;

Zhi, L., Tegley, C. M., Edwards, J. P. West, S. J., Marschke, K. B., Gottardis, M. M., Mais, D. E. Jones, T. K. 5-Alkyl-1,2-dihydrochromeno[3,4-f]quinolines: A novel class of nonsteroidal progesterone receptor modulators. *Bioorg. Med. Chem. Lett.* (1998) 8:3365-3370;

Zhi, L., Tegley, C. M., Marschke, K. B., Mais, D. E., Jones, T. K. 5-Aryl-1,2,3,4-tetrahydrochromeno[3,4-f]quinolin-3-ones as a novel class of progesterone agonist: Effect of A-ring modification. *J. Med. Chem.* (1999) 42: 1466-1472; and Zhuang et al., "Neutral and stereospecific Tc-99m complexes: [99mTc]N-i benzyl-3,4-di-(N-2-mercaptoethyl)-amino-pyrrolidines (P-BAT)" *Nuclear Medicine & Biology* 26(2):217-24, (1999).

The disclosures of each and every patent, patent application and publication (for example, journals, articles and/or textbooks) cited herein are hereby incorporated herein by reference in their entirety. Also, as used herein and in the appended claims, singular articles such as "a", "an" and "one" are intended to refer to singular or plural. While the present invention has been described herein in conjunction with a preferred aspect, a person with ordinary skill in the art, after reading the foregoing specification, can effect changes, substitutions of equivalents and other types of alterations to the compounds and probes of the invention or salts, pharmaceutical compositions, derivatives, prodrugs or racemic mixtures thereof as set forth herein. Each aspect described above can also have included or incorporated therewith such variations or aspects as disclosed in regard to any or all of the other aspects. The present invention is also not to be limited in terms of the particular aspects described herein, which are intended as single illustrations of individual aspects of the invention. Many modifications and variations of this invention can be made without departing from its spirit and scope, as will be apparent to those skilled in the art. Functionally equivalent methods within the scope of the invention, in addition to those enumerated herein, will be apparent to those skilled in the art from the foregoing descriptions. It is to be understood that this invention is not limited to particular methods, reagents, compounds, compositions, probes or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the invention indicated only by the appended claims, definitions therein and any equivalents thereof.

What is claimed is:

1. A composition, comprising a compound which is 17α-E-(2-trifluoromethyl-5-[$^{18}$F]fluoro)phenylvinyl estradiol.

* * * * *